US007479493B2

(12) United States Patent
Allison et al.

(10) Patent No.: US 7,479,493 B2
(45) Date of Patent: Jan. 20, 2009

(54) SUBSTITUTED BENZYL AMINE COMPOUNDS

(75) Inventors: Brett Allison, Del Mar, CA (US); Michael P. Curtis, Brighton, MI (US); Cheryl A. Grice, Carlsbad, CA (US); John M. Keith, San Diego, CA (US); Michael A. Letavic, San Diego, CA (US); Jennifer M. B. Miller, Kenmore, WA (US); Emily M. Stocking, Encinitas, CA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 11/766,172

(22) Filed: Jun. 21, 2007

(65) Prior Publication Data

US 2008/0045509 A1    Feb. 21, 2008

Related U.S. Application Data

(60) Provisional application No. 60/806,169, filed on Jun. 29, 2006.

(51) Int. Cl.
*A61K 31/4965* (2006.01)
*C07D 241/04* (2006.01)
*C07D 295/00* (2006.01)

(52) U.S. Cl. .................. 514/255.01; 544/391; 544/384; 514/23

(58) Field of Classification Search ............ 514/255.01; 544/391, 384
See application file for complete search history.

(56) References Cited

U.S. PATENT DOCUMENTS

| 2002/0107244 A1 | 8/2002 | Howard, Jr. |
| 2002/0143003 A1 | 10/2002 | Howard, Jr. et al. |
| 2006/0194837 A1 | 8/2006 | Carruthers et al. |
| 2006/0287292 A1 | 12/2006 | Carruthers et al. |
| 2006/0293316 A1 | 12/2006 | Apodaca et al. |

FOREIGN PATENT DOCUMENTS

| WO | WO 01/72687 | * | 4/2001 |
| WO | WO 0127068 A1 | | 4/2001 |
| WO | WO 0172687 A1 | | 10/2001 |
| WO | WO 0218333 A1 | | 3/2002 |
| WO | WO 2005040144 A1 | | 5/2005 |

OTHER PUBLICATIONS

Bagshawe, K.D.: "Antibody-Directed Enzyme Prodrug Therapy: A Review"; Drug Devel. Research (1995) 34: 220-230.
Barbier, A.J. et al.: Acute wake-promoting actions of JNJ-5207852, a novel, diamine-based H3 antagonist; British J. of Pharmacology (2004) 143: 649-661.
Barnes, J.C. et al. The Selective Histamine H3 Receptor Antagonist Thioperamide Improves Cognition and Enhances Hippocampal Acetylcholine Release In Vivo. Soc. Neurosci. Abstr. (1993) 19: 1813.
Berge, S.M. et al.: "Pharmaceutical Salts"; J. of Pharmaceutical Sciences (1977) 66(1): 1-19.
Bertolini, G. et al.: "A New Rational Hypothesis for the Pharmacophore of the Active Metabolite of Leflunomide, A Potent Immunosuppressive Drug"; J. Med. Chem. (1997) 40: 2011-2016.
Bodor, N.: Novel Approaches to the Design of Safer Drugs: Soft Drugs and Site-Specific Chemical Delivery Systems; Advances in Drug Research (1984) 13: 255-331.
Chen, Z.: "Effect of histamine $H_3$-receptor antagonst clobenpropit on spatial memory of radial maze performance in rats"; Acta Pharmacol Sin (2000) 21(10): 905-910.
Fleisher, D. et al.; "Improved oral drug delivery: solubility limitations overcome by the use of prodrugs"; Adv. Drug Del. Rev. (1996) 19: 115-130.
Fox, G.B. et al.: "Effects of histamine $H_3$ receptor ligands GT-2331 and ciproxifan in a repeated acquisition avoidance response in the spontaneously hypertensive rat pup"; Behavioural Brain Research 131 (2002): 151-161.
Hill, S.J. et al.: International Union of Pharmacology. XIII. Classification of Histamine Receptors. *Pharmacol. Rev.* 1997, 49(3), 253-278.
Lamberti, C. et al.: "Antidepressant-like effects of endogenous histamine and of two histamine $H_1$ receptor agonists in the mouse forced swim test"; British J. of Pharmacology (1998) 123: 1331-1336.
Leurs, R. et al.: The Medicinal Chemistry and Therapeutic Potentials of Ligands of the Histamine H3 Receptor. Prog. Drug Res. (1995) 45:107-165.
Machidori, H. et al.: Zucker Obese Rats: Defect in Brain Histamine Control of Feeding. Brain Res. (1992) 590: 180-186.
Miyazaki, S. et al.: "Effects of Thioperamide on the Cholinergic System and the Step-Through Passive Avoidance Test in Mice"; Meth Find Exp Clin Pharmacol (1995) 17(10): 653-658.
Miyazaki, S. et al.: "Effects of Thioperamide, a Histamine $H_3$-receptor Antagonist, on a Scopolamine-induced Learning Deficit Using an Elevated Plus-maze Test in Mice"; Life Sciences, (1995) 57(23): 2137-2144.
Morisset, S. et al.: High Constitutive Activity of Native H3 Receptors Regulates Histamine Neurons in Brain. Nature (Dec. 2000) 408: 860-864.
Orsetti, M. et al.: "Histamine $H_3$-receptor antagonism improves memory retention and reverses the cognitive deficit induced by scopolamine in a two-trial place recognition task"; Elsevier Behavioural Brain Research 124 (2001): 235-242.
Panula, P. et al.: Significant Changes in the Human Brain Histaminergic System in Alzheimer's Disease. Soc. Neurosci. Abstr. (1995) 21: 1977.
Perez-Garcia, C. et al.: "Effects of histamine $H_3$ receptor ligands in experimental models of anxiety and depression"; Psychopharmacology (1999) 142: 215-220.

(Continued)

*Primary Examiner*—James O. Wilson
*Assistant Examiner*—Erich A Leeser

(57) ABSTRACT

Certain substituted benzyl amine compounds are histamine $H_3$ receptor and/or serotonin transporter modulators useful in the treatment of histamine $H_3$ receptor- and/or serotonin-mediated diseases.

31 Claims, No Drawings

OTHER PUBLICATIONS

Robinson, R.P. et al.: "Discovery of the Hemifumarate and (α-L-Alanyloxy)methyl Ether as Prodrugs of an Antirheumatic Oxindole: Prodrugs for the Enolic OH Group"; J. Med. Chem. (1996) 39: 10-18.

Schlicker, E. et al.: The Moderate Affinity of Clozapine at H3 Receptors Is Not Shared by Its Two Major Metabolites and by Structurally Related and Unrelated Atypical Neuroleptics. Naunyn-Schmiedeberg's Arch. Pharmacol. (1996) 353:290-294.

Shan, D. et al.: "Prodrug Strategies Based on Intramolecular Cyclization Reactions"; J. of Pharm. Sciences (Jul. 1997) 86(7): 765-767.

Stark, H. et al. Developments of Histamine H3-Receptor Antagonists. Drugs Future (1996) 21(5): 507-520.

Yokoyama, H. et al.: Effect of Thioperamide, a Histamine $H_3$ Receptor Antagonist, on Electrically Induced Convulsions in Mice. Eur. J. Pharmacol. (1993) 234: 129-133.

PCT International Search Report for International Application No. PCT/US2007/071742 dated May 8, 2008.

* cited by examiner

SUBSTITUTED BENZYL AMINE COMPOUNDS

CROSS-REFERENCE TO RELATED APPLICATIONS

This application claims the benefit of U.S. Provisional Application 60/806,169, filed Jun. 29, 2006, which is hereby incorporated by reference in its entirety.

FIELD OF THE INVENTION

The present invention relates to certain benzyl amine compounds, pharmaceutical compositions containing them, and methods of using them for the treatment of disease states, disorders, and conditions mediated by the histamine $H_3$ receptor and/or the serotonin transporter.

BACKGROUND OF THE INVENTION

The histamine $H_3$ receptor is primarily expressed in the mammalian central nervous system (CNS), with some minimal expression in peripheral tissues such as vascular smooth muscle. Several indications for histamine $H_3$ antagonists and inverse agonists have been proposed based on animal pharmacology and other experiments with known histamine $H_3$ antagonists (e.g. thioperamide). (See: "The Histamine $H_3$ Receptor-A Target for New Drugs", Leurs, R. and Timmerman, H., (Eds.), Elsevier, 1998; Morisset, S. et al., Nature 2000, 408, 860-864.) These include conditions such as cognitive disorders, sleep disorders, psychiatric disorders, and other disorders.

Compounds that possess histamine $H_3$ receptor activity and serotonin transporter (SERT) activity may be useful in the treatment of SERT-mediated disorders such as substance abuse disorders and sexual dysfunction (including premature ejaculation), and particularly beneficial in the treatment of depression. Activation of the $H_3$ receptor on neurons by histamine or an agonist decreases the release of several neurotransmitters including noradrenaline and serotonin, key neurotransmitters involved in depression (Hill, S. J. et al. *Pharmacol. Rev.* 1997, 49(3), 253-278). Although $H_3$ receptor antagonists alone may not be capable of increasing serotonin levels in vivo to those required for antidepressant effects, concomitant blockade of the SERT will simultaneously decrease the neuronal reuptake of these neurotransmitter molecules, leading to enhanced concentrations of serotonin in the synaptic cleft and an enhanced therapeutic effect and a potentially reduced side effect profile as compared to a compound with SERT activity alone.

Histamine $H_3$ antagonists have been shown to have pharmacological activity relevant to several key symptoms of depression, including sleep disorders (e.g. sleep disturbances, fatigue, and lethargy) and cognitive difficulties (e.g. memory and concentration impairment), as described above. Therefore, a combined $H_3$/SERT modulating compound would provide symptomatic relief for the sleep disorders, fatigue, and cognitive problems during the first weeks of treatment, before the mood-elevating effect of the SERT modulation is noticed.

Compounds that have $H_3$ receptor activity and SERT activity have been disclosed in U.S. Pat. Publ. US 2006/0194837 A1 (published Aug. 31, 2006; based on U.S. patent application Ser. No. 11/300,880), U.S. Pat. Publ. US 2006/0293316 A1 (published Dec. 28, 2006; based on U.S. patent application Ser. No. 11/424,734), and U.S. Pat. Publ. US 2006/0287292 A1 (published Dec. 21, 2006; based on U.S. patent application Ser. No. 11/424,751), each of which is hereby incorporated by reference.

Aminomethyl phenyl ethers have been described by Pfizer, in Intl. Patent Appl. Publ. No. WO 01/72687, WO 02/18333, and U.S. Patent Appl. Publ. No. US 2002/0143003. Heteratom-linked aryl benzamides have been described by Glaxo SmithKline, in Intl. Patent Appl. Publ. No. WO 05/040144.

However, there remains a need for potent histamine $H_3$ receptor and/or serotonin transporter modulators with desirable pharmaceutical properties.

SUMMARY OF THE INVENTION

Certain benzyl amine derivatives have now been found to have histamine $H_3$ receptor and/or serotonin transporter modulating activity. Thus, the invention is directed to the general and preferred embodiments defined, respectively, by the independent and dependent claims appended hereto, which are incorporated by reference herein.

In one general aspect the invention relates to a compound of the following Formula (I):

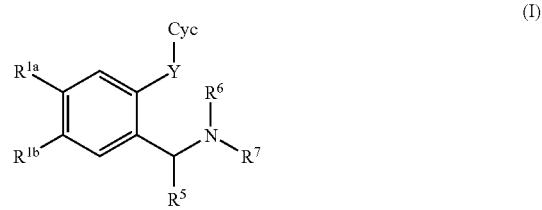

(I)

wherein
one of $R^{1a}$ and $R^{1b}$ is

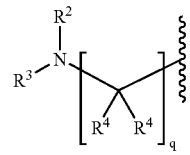

and the other is —H;

$R^2$ and $R^3$ are each independently selected from the group consisting of: —H; a —$C_{1-6}$alkyl group unsubstituted or substituted with —OH, —$OC_{1-4}$alkyl, —$NH_2$, —$N(R^a)R^b$, or —F; —$CO_2C_{1-4}$alkyl; and a monocyclic cycloalkyl group unsubstituted or substituted with —$C_{1-4}$alkyl, —OH, halo, or —$CF_3$;

where $R^a$ and $R^b$ are each independently —H, —$C_{1-6}$alkyl, or monocyclic cycloalkyl, or $R^a$ and $R^b$ taken together with their nitrogen of attachment form a monocyclic heterocycloalkyl group;

provided that $R^2$ and $R^3$ are not both H;

or, alternatively, $R^2$ and $R^3$ taken together with the nitrogen to which they are attached form a saturated monocyclic heterocycloalkyl group unsubstituted or substituted on a carbon ring member with one, two, or three $R^d$ moieties and substituted on a nitrogen ring member with an $R^e$ moiety;

where each $R^d$ moiety is independently selected from the group consisting of: —$C_{1-6}$alkyl; —$C_{1-4}$alkyl-OH; halo; —OH; —$OC_{1-6}$alkyl; ipso-substituted —$OC_{2-3}$ alkylO—; —CN; —NO$_2$; —N(R$^g$)R$^h$; —C(O)N(R$^g$)R$^h$; —N(R$^g$)SO$_2$C$_{1-6}$alkyl; —C(O)C$_{1-6}$alkyl; —S(O)$_{0-2}$—C$_{1-6}$alkyl; —SO$_2$N(R$^g$)R$^h$; —SCF$_3$; —CF$_3$; —OCF$_3$; —CO$_2$H; and —CO$_2$C$_{1-6}$alkyl;

where R$^g$ and R$^h$ are each independently —H or —C$_{1-6}$ alkyl, or R$^g$ and R$^h$ taken together with their nitrogen of attachment form a monocyclic heterocycloalkyl group; and where R$^e$ is selected from the group consisting of: —H; a —C$_{1-6}$alkyl or —C(O)C$_{1-6}$alkyl group unsubstituted or substituted with halo, —CN, —OH, —OC$_{1-4}$alkyl, or —CF$_3$; —C(O)CF$_3$; —S(O)$_{0-2}$—C$_{1-6}$alkyl; —CO$_2$C$_{1-6}$ alkyl; and a phenyl, monocyclic carbon-linked heteroaryl, monocyclic cycloalkyl, or monocyclic carbon-linked heterocycloalkyl group, each unsubstituted or substituted with —C$_{1-4}$alkyl, halo, —CN, —OH, —OC$_{1-4}$alkyl, or —CF$_3$;

q is 0 or 1;

each R$^4$ is independently —H or methyl, or both R$^4$ substituents taken together form a carbonyl;

Y is —O—, —OCH$_2$—, —S—, —SO—, or —SO$_2$—;

R$^5$ is —H or —C$_{1-6}$alkyl;

R$^6$ is —H; or —C$_{1-6}$alkyl, —C$_{3-6}$alkenyl, —C$_{3-6}$alkynyl, monocyclic cycloalkyl, or —C$_{1-6}$alkyl-(monocyclic cycloalkyl), each unsubstituted or substituted with —C$_{1-4}$ alkyl, —OH, —OC$_{1-4}$alkyl, halo, —NH$_2$, —NH(C$_{1-4}$ alkyl), —N(C$_{1-4}$alkyl)$_2$, —CN, —CO$_2$H, or —CO$_2$C$_{1-4}$ alkyl;

R$^7$ is —H; or —C$_{1-6}$alkyl, —C$_{3-6}$alkenyl, —C$_{3-6}$alkynyl, monocyclic cycloalkyl, or —C$_{1-6}$alkyl-(monocyclic cycloalkyl), each unsubstituted or substituted with —C$_{1-4}$ alkyl, —OH, —OC$_{1-4}$alkyl, halo, —NH$_2$, —NH(C$_{1-4}$ alkyl), —N(C$_{1-4}$alkyl)$_2$, —CN, —CO$_2$H, or —CO$_2$C$_{1-4}$ alkyl;

or R$^6$ and R$^7$ taken together with their nitrogen of attachment form a saturated monocyclic heterocycloalkyl group unsubstituted or substituted with —C$_{1-4}$alkyl, —OC$_{1-4}$ alkyl, or halo; and Cyc is a phenyl or monocyclic carbon-linked heteroaryl group, unsubstituted or substituted with one, two, or three R$^k$ moieties;

where each R$^k$ moiety is independently selected from the group consisting of: —C$_{1-6}$alkyl, —CHF$_2$, —CF$_3$, —C$_{2-6}$alkenyl, —C$_{2-6}$alkynyl, —OH, —OC$_{1-6}$alkyl, —OCHF$_2$, —OCF$_3$, —OC$_{3-6}$alkenyl, —OC$_{3-6}$alkynyl, —CN, —NO$_2$, —N(R$^l$)R$^m$, —N(R$^l$)C(O)R$^m$, —N(R$^l$)SO$_2$C$_{1-6}$alkyl, —C(O)C$_{1-6}$alkyl, —S(O)$_{0-2}$—C$_{1-6}$alkyl, —C(O)N(R$^l$)R$^m$, —SO$_2$N(R$^l$)R$^m$, —SCF$_3$, halo, —CO$_2$H, and —CO$_2$C$_{1-6}$alkyl; or two R$^k$ moieties on adjacent carbon atoms of attachment together are —OC$_{1-4}$alkyleneO— to form a cyclic ring which is unsubstituted or substituted with one or two fluoro substituents;

where R$^l$ and R$^m$ are each independently —H or —C$_{1-6}$ alkyl;

provided that when both R$^4$ substituents taken together form a carbonyl, then R$^2$ and R$^3$ taken together are not diazepanyl;

or a pharmaceutically acceptable salt, pharmaceutically acceptable prodrug, or pharmaceutically active metabolite of such compound.

In a further general aspect, the invention relates to pharmaceutical compositions each comprising: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

In another general aspect, the invention is directed to a method of treating a subject suffering from or diagnosed with a disease, disorder, or medical condition mediated by histamine H$_3$ receptor and/or serotonin transporter activity, comprising administering to the subject in need of such treatment an effective amount of a compound of Formula (I), or a pharmaceutically acceptable salt, pharmaceutically acceptable prodrug, or pharmaceutically active metabolite thereof.

In certain preferred embodiments of the inventive method, the disease, disorder, or medical condition is selected from: cognitive disorders, sleep disorders, psychiatric disorders, and other disorders.

Additional embodiments, features, and advantages of the invention will be apparent from the following detailed description and through practice of the invention.

DETAILED DESCRIPTION

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by /), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkylene" refers to a straight- or branched-chain alkyl group having from 1 to 12 carbon atoms in the chain, where two hydrogen atoms are removed to for a diradical. Examples of alkylene groups include methylene (—CH$_2$—), ethylene, n-propylene, isopropylene, butylene, and groups that in light of the ordinary skill in the art and the teachings provided herein would be considered equivalent to any one of the foregoing examples.

The term "alkenyl" refers to a straight- or branched-chain alkenyl group having from 2 to 12 carbon atoms in the chain. (The double bond of the alkenyl group is formed by two sp$^2$ hybridized carbon atoms.) Illustrative alkenyl groups include prop-2-enyl, but-2-enyl, but-3-enyl, 2-methylprop-2-enyl, hex-2-enyl, and groups that in light of the ordinary skill in the art and the teachings provided herein would be considered equivalent to any one of the foregoing examples.

The term "alkynyl" refers to a straight- or branched-chain alkynyl group having from 2 to 12 carbon atoms in the chain. (The triple bond of the alkynyl group is formed by two sp hybridized carbon atoms.) Illustrative alkynyl groups include ethynyl, propynyl, butynyl, hexynyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

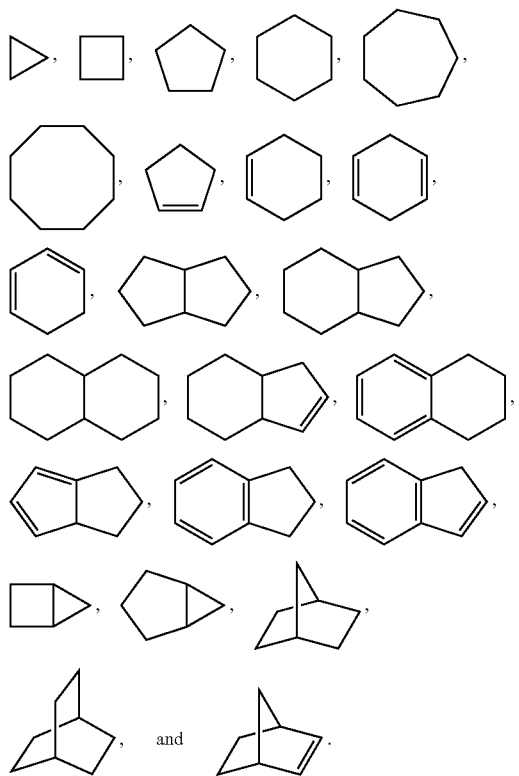

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

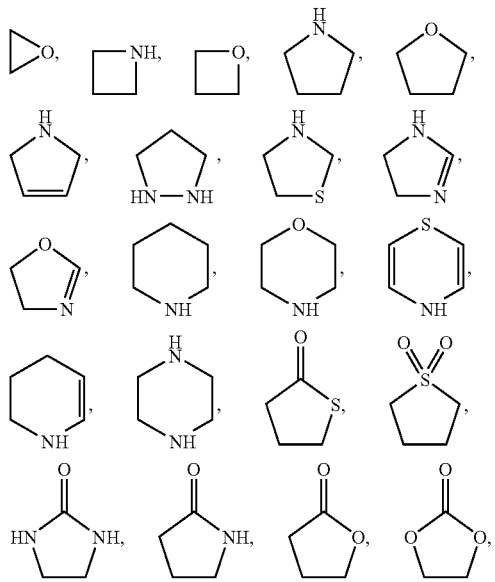

-continued

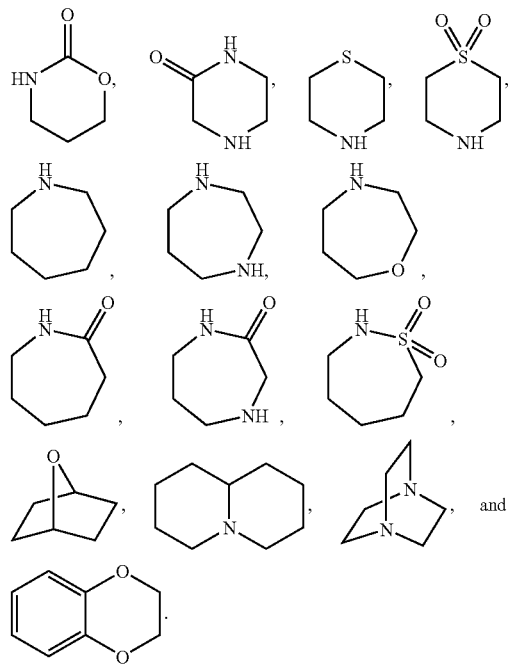

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

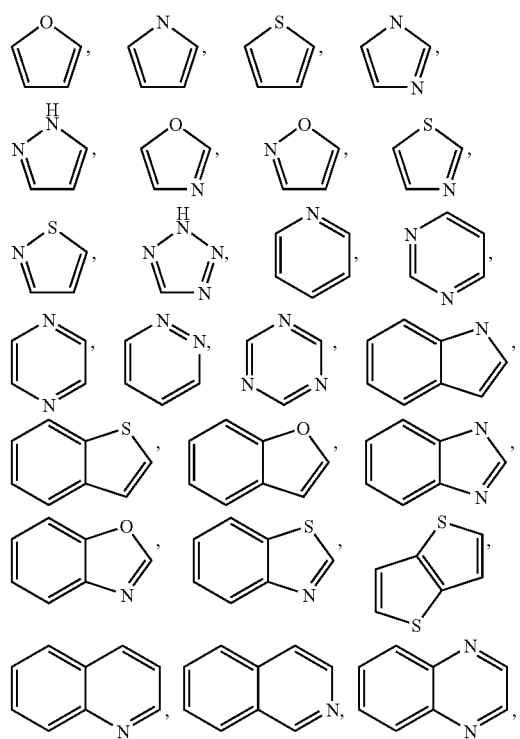

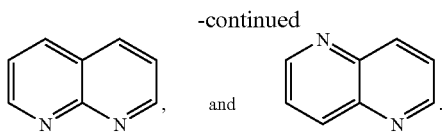

Those skilled in the art will recognize that the species of heteroaryl, cycloalkyl, and heterocycloalkyl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

In preferred embodiments of Formula (I), $R^{1b}$ is

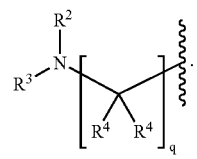

In preferred embodiments, $R^2$ and $R^3$ are each independently —H; or methyl, ethyl, propyl, isopropyl, sec-butyl, 2-methylpropyl, cyclopropyl, cyclobutyl, or cyclopentyl, each unsubstituted or substituted as previously described. In further preferred embodiments, $R^2$ and $R^3$ are each independently —H, methyl, ethyl, propyl, isopropyl, sec-butyl, 2-hydroxyethyl, 2-methoxyethyl, 2-methylaminoethyl, 2-dimethylaminoethyl, 2-(cyclopropyl-methyl-amino)-ethyl, 2-pyrrolidin-1-yl-ethyl, 2-hydroxy-2-methylpropyl, 3-dimethylaminopropyl, cyclopropyl, cyclobutyl, or cyclopentyl. In still further preferred embodiments, $R^2$ and $R^3$ are each independently —H, methyl, cyclopropyl, dimethylaminoethyl, or dimethylaminopropyl.

In preferred embodiments, $R^a$ and $R^b$ are each independently —H, methyl, or cyclopropyl, or $R^a$ and $R^b$ taken together form pyrrolidinyl.

In alternative embodiments, $R^2$ and $R^3$ taken together with the nitrogen to which they are attached form azetidinyl, pyrrolidinyl, piperidinyl, piperazinyl, morpholinyl, thiomorpholinyl, 1,1-dioxo-1λ$^6$-thiomorpholin-4-yl, homopiperidinyl, diazepanyl, piperazinonyl, or diazepanonyl, each unsubstituted or substituted as previously described. In certain preferred embodiments, $R^2$ and $R^3$ taken together with the nitrogen to which they are attached form azetidinyl, 3,3-difluoroazetidinyl, pyrrolidinyl, 2-methylpyrrolidinyl, 3-hydroxypyrrolidinyl, 3-dimethylaminopyrrolidinyl, 2,5-dimethylpyrrolidinyl, 2-trifluoromethylpyrrolidinyl, 2-hydroxymethylpyrrolidinyl, 3,3-difluoropyrrolidinyl, piperidinyl, 3-fluoropiperidinyl, 4-fluoropiperidinyl, 3,3-difluoropiperidinyl, 4,4-difluoropiperidinyl, 3-trifluoromethylpiperidinyl, 4-trifluoromethylpiperidinyl, 1,4-dioxa-8-aza-spiro [4.5]dec-8-yl, 4-cyanopiperidinyl, 4-carboethoxypiperidinyl, 3-hydroxypiperidinyl, 4-hydroxypiperidinyl, 2-hydroxymethylpiperidinyl, 3-hydroxymethylpiperidinyl, 4-hydroxymethylpiperidinyl, 3-hydroxyethylpiperidinyl, 4-hydroxyethylpiperidinyl, 4-dimethylaminopiperidinyl, 4-morpholin-4-yl-piperidin-1-yl, morpholinyl, 2-methylmorpholin-4-yl, 3-methylmorpholin-4-yl, 2,6-dimethylmorpholin-4-yl, 3-hydroxymethylmorpholin-4-yl, 2-hydroxymethylmorpholin-4-yl, piperazinyl, 4-methyl-piperazin-1-yl, 4-ethyl-piperazin-1-yl, 4-(2-fluoroethyl)-piperazin-1-yl, 4-isopropyl-piperazin-1-yl, 4-cyclopropyl-piperazin-1-yl, 4-cyclobutyl-piperazin-1-yl, 4-cyclopentyl-piperazin-1-yl, 4-(2-hydroxyethyl)piperazin-1-yl, 4-(2-methoxyethyl)-piperazin-1-yl, 4-(tert-butoxycarbonyl)

piperazin-1-yl, 4-phenylpiperazin-1-yl, 4-(2-hydroxyphenyl)piperazinyl, 4-(4-trifluoromethyl-phenyl)-piperazin-1-yl, 4-thiazol-2-yl-piperazin-1-yl, 4-(2-thiophenyl) piperazinyl, 4-pyridin-4-yl-piperazin-1-yl, 4-acetylpiperazin-1-yl, 4-isobutyryl-piperazin-1-yl, 4-piperazin-2-onyl, 1-isopropyl-4-piperazin-2-onyl, 4-isopropyl-1-piperazin-2-onyl, 1-cyclopropyl-4-piperazin-2-onyl, thiomorpholinyl, 1,1-dioxo-1$\lambda^6$-thiomorpholin-4-yl, 4-isopropyl-[1,4]diazepan-1-yl, 4-cyclopropyl-[1,4]diazepan-1-yl, 1-cyclobutyl-4-diazepan-5-onyl, 4-isopropyl-1-diazepan-5-onyl, 1-isopropyl-4-diazepan-5-onyl, or 1-cyclopropyl-4-diazepan-5-onyl. In further preferred embodiments, $R^2$ and $R^3$ taken together with the nitrogen to which they are attached form pyrrolidinyl, 3-dimethylaminopyrrolidinyl, piperidinyl, 4-fluoropiperidinyl, 4-dimethylaminopiperidinyl, 4-morpholin-4-yl-piperidin-1-yl, morpholinyl, thiomorpholinyl, piperazinyl, 4-methyl-piperazin-1-yl, 4-isopropyl-piperazin-1-yl, 4-(2-fluoroethyl)-piperazin-1-yl, 4-cyclopropyl-piperazin-1-yl, 4-cyclobutyl-piperazin-1-yl, 4-cyclopentyl-piperazin-1-yl, 4-pyridin-4-yl-piperazin-1-yl, 4-piperazin-2-onyl, 1-isopropyl-4-piperazin-2-onyl, 4-isopropyl-[1,4]diazepan-1-yl, or 1-isopropyl-4-diazepan-5-onyl.

In preferred embodiments, each $R^d$ moiety is independently selected from the group consisting of: methyl, ethyl, isopropyl, hydroxyethyl, fluoro, methoxy, dimethylamino, piperidinyl, morpholinyl, acetyl, trifluoromethyl, —$CO_2H$, and —$CO_2$-methyl.

In preferred embodiments, $R^g$ and $R^h$ are each independently —H, methyl, ethyl, or isopropyl, or $R^g$ and $R^h$ taken together with their nitrogen of attachment form pyrrolidinyl, piperidinyl, morpolinyl, or thiomorpholinyl.

In preferred embodiments, $R^e$ is selected from the group consisting of: —H, methyl, ethyl, isopropyl, 2-fluoroethyl, hydroxyethyl, methoxypropyl, acetyl, tert-butoxycarbonyl, phenyl, 4-pyridyl, cyclopropyl, cyclobutyl, cyclopentyl, and piperidinyl. In further preferred embodiments, $R^e$ is selected from the group consisting of: —H, isopropyl, and cyclopropyl.

In preferred embodiments, q is 1 and both $R^4$ substituents taken together form a carbonyl. In other preferred embodiments, q is 0. In still other preferred embodiments, q is 1 and each $R^4$ is —H.

In preferred embodiments, Y is —O— or —S—.

In preferred embodiments, Cyc is a phenyl or pyridyl group unsubstituted or substituted with one, two, or three $R^k$ moieties. In further preferred embodiments, Cyc is a thiophenyl, oxazolyl, thiazolyl, pyrazolyl, pyridinyl, or pyrazinyl group unsubstituted or substituted with one, two, or three $R^k$ moieties.

In further preferred embodiments, Cyc is phenyl, 2-hydroxyphenyl, 3-hydroxyphenyl, 4-hydroxyphenyl, 4-hydroxy-2-methylphenyl, 4-hydroxy-3-fluorophenyl, 3,4-dihydroxyphenyl, 2-methoxyphenyl, 3-methoxyphenyl, 4-methoxyphenyl, 4-ethoxyphenyl, 2,4-dimethoxyphenyl, 2,5-dimethoxyphenyl, 3,4-dimethoxyphenyl, 3,5-dimethoxyphenyl, 3,4,5-trimethoxyphenyl, 2-methylphenyl, 3-methylphenyl, 4-methylphenyl, 4-ethylphenyl, 3-ethynylphenyl, 4-ethynylphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 3-iodophenyl, 4-iodophenyl, 2,3-difluorophenyl, 2,4-difluorophenyl, 3,4-difluorophenyl, 2,3-dichlorophenyl, 2,4-dichlorophenyl, 2,5-dichlorophenyl, 3,4-dichlorophenyl, 3,5-dichlorophenyl, 2-fluoro-3-chlorophenyl, 2-fluoro-4-chlorophenyl, 2-chloro-4-fluorophenyl, 3-fluoro-4-chlorophenyl, 3-chloro-4-fluorophenyl, 4-fluoro-3-methylphenyl, 3-chloro-4-methoxyphenyl, 2-fluoro-4-methoxyphenyl, 3-fluoro-4-methoxyphenyl, 3-chloro-4-difluoromethoxyphenyl, 4-chloro-3-trifluoromethylphenyl, 2-trifluoromethylphenyl, 3-trifluoromethylphenyl, 4-trifluoromethylphenyl, 3-trifluoromethoxyphenyl, 4-trifluoromethoxyphenyl, 4-difluoromethoxyphenyl, 2-cyanophenyl, 3-cyanophenyl, 4-cyanophenyl, 3-acetylphenyl, 4-acetylphenyl, 3-nitrophenyl, 4-nitrophenyl, 4-aminophenyl, 4-dimethylaminophenyl, 4-carbamoylphenyl, 4-methanesulfanylphenyl, 4-methanesulfinylphenyl, 4-methanesulfonylphenyl, 4-trifluoromethanesulfanylphenyl, 3-methyl-4-methylsulfanylphenyl, benzo[1,3]dioxol-4-yl, benzo[1,3]dioxol-5-yl, thiophen-2-yl, thiophen-3-yl, oxazol-5-yl, thiazol-5-yl, thiazol-2-yl, 2H-pyrazol-3-yl, 2-pyridinyl, 3-pyridinyl, 4-pyridinyl, 4-trifluoromethyl-pyridin-2-yl, 2,6-dimethyl-pyridin-3-yl, 6-methyl-pyridin-3-yl, 2-chloro-5-pyridinyl, 2-dimethylamino-5-pyridinyl, 6-methoxy-pyridin-3-yl, 6-methylsulfanyl-pyridin-3-yl, 2-hydroxy-5-pyridinyl, 6-bromo-pyridin-3-yl, or pyrazin-2-yl.

In certain particular embodiments, Cyc is phenyl, 3-methoxyphenyl, 3-fluorophenyl, 4-fluorophenyl, 3-chlorophenyl, 4-chlorophenyl, 3,4-dichlorophenyl, 3-chloro-2-fluorophenyl, 4-chloro-2-fluorophenyl, 3-chloro-4-fluorophenyl, 4-trifluoromethylphenyl, 4-methanesulfanylphenyl, 3-methyl-4-methanesulfanylphenyl, 2-pyridinyl, 3-pyridinyl, or 6-methyl-3-pyridinyl.

In preferred embodiments, each $R^k$ moiety is independently selected from the group consisting of: methyl, methoxy, fluoro, chloro, trifluoromethyl, methanesulfanyl, trifluoromethanesulfanyl, cyano, and trifluoromethoxy.

In preferred embodiments, $R^l$ and $R^m$ are each independently —H or methyl.

In preferred embodiments, $R^5$ is —H or methyl. In further preferred embodiments, $R^5$ is —H.

In preferred embodiments, $R^6$ is —H, methyl, ethyl, isopropyl, sec-butyl, cyclopropyl, cyclobutyl, or cyclopentyl, each unsubstituted or substituted as previously described. In further preferred embodiments, $R^6$ is —H or methyl.

In preferred embodiments, $R^7$ is —H, methyl, ethyl, propyl, isopropyl, sec-butyl, cyclopropyl, cyclobutyl, cyclopentyl, cyclohexyl, cyclopropylmethyl, cyclobutylmethyl, or cyclopentylmethyl, each unsubstituted or substituted as previously described. In further preferred embodiments, $R^7$ is methyl, ethyl, isopropyl, sec-butyl, cyclopropyl, cyclobutyl, or cyclopentyl. In still further preferred embodiments, $R^7$ is methyl, ethyl, isopropyl, or cyclopropyl.

In alternative embodiments, $R^6$ and $R^7$ taken together with their nitrogen of attachment form azetidinyl, pyrrolidinyl, piperidinyl, piperazinyl, morpholinyl, thiomorpholinyl, 1,1-dioxo-1$\lambda^6$-thiomorpholin-4-yl, homopiperidinyl, diazepanyl, or homomorpholinyl, each unsubstituted or substituted as previously described. In further preferred embodiments, $R^6$ and $R^7$ taken together with their nitrogen of attachment form piperidinyl, pyrrolidinyl, morpholinyl, 4-isopropyl-piperazin-1-yl, or homomorpholinyl.

In certain preferred embodiments, the compound of Formula (I) is selected from the group consisting of:

| Ex. | Compound Name |
|---|---|
| 1 | [4-(3,4-Dichloro-phenoxy)-3-methylaminomethyl-phenyl]-(4-isopropyl-piperazin-1-yl)-methanone; |
| 2 | (4-Cyclopropyl-piperazin-1-yl)-[3-methylaminomethyl-4-(4-methylsulfanyl-phenoxy)-phenyl]-methanone; |

-continued

| Ex. | Compound Name |
|---|---|
| 3 | (4-Isopropyl-piperazin-1-yl)-[3-methylaminomethyl-4-(4-methylsulfanyl-phenoxy)-phenyl]-methanone; |
| 4 | (4-Isopropyl-piperazin-1-yl)-[3-methylaminomethyl-4-(3-methyl-4-methylsulfanyl-phenoxy)-phenyl]-methanone; |
| 5 | (4-Cyclopropyl-piperazin-1-yl)-[4-(3,4-dichloro-phenoxy)-3-methylaminomethyl-phenyl]-methanone; |
| 6 | (4-Isopropyl-piperazin-1-yl)-[4-(3-methoxy-phenoxy)-3-methylaminomethyl-phenyl]-methanone; |
| 7 | [4-(4-Chloro-phenoxy)-3-methylaminomethyl-phenyl]-(4-isopropyl-piperazin-1-yl)-methanone; |
| 8 | [4-(4-Chloro-phenoxy)-3-cyclopropylaminomethyl-phenyl]-(4-isopropyl-piperazin-1-yl)-methanone; |
| 9 | (4-Isopropyl-piperazin-1-yl)-[3-methylaminomethyl-4-(pyridin-3-yloxy)-phenyl]-methanone; |
| 10 | (4-Cyclopropyl-piperazin-1-yl)-[3-methylaminomethyl-4-(pyridin-3-yloxy)-phenyl]-methanone; |
| 11 | [4-(3-Chloro-phenoxy)-3-methylaminomethyl-phenyl]-(4-cyclopropyl-piperazin-1-yl)-methanone; |
| 12 | (4-Cyclopropyl-piperazin-1-yl)-(3-methylaminomethyl-4-phenoxy-phenyl)-methanone; |
| 13 | (4-Cyclopropyl-piperazin-1-yl)-[4-(3-fluoro-phenoxy)-3-methylaminomethyl-phenyl]-methanone; |
| 14 | (4-Cyclopropyl-piperazin-1-yl)-[3-methylaminomethyl-4-(4-trifluoromethyl-phenoxy)-phenyl]-methanone; |
| 15 | [3-Cyclopropylaminomethyl-4-(pyridin-3-yloxy)-phenyl]-(4-cyclopropyl-piperazin-1-yl)-methanone; |
| 16 | (4-Cyclopropyl-piperazin-1-yl)-[3-methylaminomethyl-4-(3-methyl-4-methylsulfanyl-phenoxy)-phenyl]-methanone; |
| 17 | [3-Cyclopropylaminomethyl-4-(pyridin-3-yloxy)-phenyl]-(4-isopropyl-piperazin-1-yl)-methanone; |
| 18 | [4-(4-Chloro-phenoxy)-3-methylaminomethyl-phenyl]-(4-cyclopropyl-piperazin-1-yl)-methanone; |
| 19 | (4-Cyclopropyl-piperazin-1-yl)-[4-(4-fluoro-phenoxy)-3-methylaminomethyl-phenyl]-methanone; |
| 20 | (4-Cyclopropyl-piperazin-1-yl)-[3-methylaminomethyl-4-(6-methyl-pyridin-3-yloxy)-phenyl]-methanone; |
| 21 | [4-(3-Chloro-4-fluoro-phenoxy)-3-methylaminomethyl-phenyl]-(4-cyclopropyl-piperazin-1-yl)-methanone; |
| 22 | [4-(3-Chloro-2-fluoro-phenoxy)-3-methylaminomethyl-phenyl]-(4-cyclopropyl-piperazin-1-yl)-methanone; |
| 23 | [3-Methylaminomethyl-4-(4-methylsulfanyl-phenoxy)-phenyl]-(4-morpholin-4-yl-piperidin-1-yl)-methanone; |
| 24 | [4-(3-Chloro-2-fluoro-phenoxy)-3-methylaminomethyl-phenyl]-(4-cyclopropyl-piperazin-1-yl)-methanone; |
| 25 | (S)-3-Dimethylamino-pyrrolidin-1-yl)-[3-methylaminomethyl-4-(4-methylsulfanyl-phenoxy)-phenyl]-methanone; |
| 26 | 4-(3-Chloro-phenoxy)-N-(2-dimethylamino-ethyl)-3-methylaminomethyl-benzamide; |
| 27 | 4-(3-Chloro-phenoxy)-N-(3-dimethylamino-propyl)-3-methylaminomethyl-benzamide; |
| 28 | [4-(4-Chloro-phenylsulfanyl)-3-methylaminomethyl-phenyl]-(4-cyclopropyl-piperazin-1-yl)-methanone; |
| 29 | (4-Cyclopropyl-piperazin-1-yl)-[3-methylaminomethyl-4-(pyridin-2-ylsulfanyl)-phenyl]-methanone; |
| 30 | [4-Cyclopropylaminomethyl-3-(pyridin-3-yloxy)-phenyl]-(4-isopropyl-piperazin-1-yl)-methanone; |
| 31 | [4-Cyclopropylaminomethyl-3-(pyridin-3-yloxy)-phenyl]-(4-cyclopropyl-piperazin-1-yl)-methanone; |
| 32 | [4-Cyclopropylaminomethyl-3-(pyridin-3-yloxy)-phenyl]-(3-dimethylamino-pyrrolidin-1-yl)-methanone; |
| 33 | (4-Isopropyl-piperazin-1-yl)-[4-piperidin-1-ylmethyl-3-(pyridin-3-yloxy)-phenyl]-methanone; |
| 34 | (4-Cyclopropyl-piperazin-1-yl)-[4-piperidin-1-ylmethyl-3-(pyridin-3-yloxy)-phenyl]-methanone; |
| 35 | (3-Dimethylamino-pyrrolidin-1-yl)-[4-piperidin-1-ylmethyl-3-(pyridin-3-yloxy)-phenyl]-methanone; |
| 36 | [3-(4-Chloro-phenoxy)-4-methylaminomethyl-phenyl]-(4-isopropyl-piperazin-1-yl)-methanone; |
| 37 | [3-(3,4-Dichloro-phenoxy)-4-methylaminomethyl-phenyl]-(4-isopropyl-piperazin-1-yl)-methanone; |
| 38 | [3-(3-Chloro-phenoxy)-4-methylaminomethyl-phenyl]-(4-isopropyl-piperazin-1-yl)-methanone; |
| 39 | (4-Cyclopropyl-piperazin-1-yl)-[3-(3,4-dichloro-phenoxy)-4-methylaminomethyl-phenyl]-methanone |
| 40 | [5-(4-Isopropyl-piperazin-1-yl)-2-(4-methylsulfanyl-phenoxy)-benzyl]-methyl-amine; |
| 41 | Methyl-[5-(4-methyl-piperazin-1-yl)-2-(4-methylsulfanyl-phenoxy)-benzyl]-amine; |
| 42 | [5-(4-Cyclobutyl-piperazin-1-yl)-2-(4-methylsulfanyl-phenoxy)-benzyl]-methyl-amine; |
| 43 | Methyl-[2-(4-methylsulfanyl-phenoxy)-5-(4-pyridin-4-yl-piperazin-1-yl)-benzyl]-amine; |
| 44 | [5-[4-(2-Fluoro-ethyl)-piperazin-1-yl]-2-(4-methylsulfanyl-phenoxy)-benzyl]-methyl-amine; |
| 45 | [5-(4-Cyclopropyl-piperazin-1-yl)-2-(4-methylsulfanyl-phenoxy)-benzyl]-methyl-amine |
| 46 | [5-(4-Cyclopropyl-piperazin-1-yl)-2-(3,4-dichloro-phenoxy)-benzyl]-methyl-amine; |
| 47 | [2-(3,4-Dichloro-phenoxy)-5-(4-isopropyl-piperazin-1-yl)-benzyl]-methyl-amine; |
| 48 | 1-[3-Methylaminomethyl-4-(4-methylsulfanyl-phenoxy)-phenyl]-piperazin-2-one; |
| 49 | 4-Isopropyl-1-[3-methylaminomethyl-4-(4-methylsulfanyl-phenoxy)-phenyl]-piperazin-2-one; |
| 50 | 1-[4-(3,4-Dichloro-phenoxy)-3-methylaminomethyl-phenyl]-4-isopropyl-piperazin-2-one; |
| 51 | Methyl-[2-(4-methylsulfanyl-phenoxy)-5-(4-morpholin-4-yl-piperidin-1-yl)-benzyl]-amine; |
| 52 | [5-(4-Isopropyl-[1,4]diazepan-1-yl)-2-(4-methylsulfanyl-phenoxy)-benzyl]-methyl-amine; |
| 53 | [5-(4-Cyclopropyl-[1,4]diazepan-1-yl)-2-(4-methylsulfanyl-phenoxy)-benzyl]-methyl-amine; |
| 54 | 1-Isopropyl-4-[3-methylaminomethyl-4-(4-methylsulfanyl-phenoxy)-phenyl]-[1,4]diazepan-5-one; |
| 55 | [2-(3,4-Dichloro-phenoxy)-5-(4-isopropyl-[1,4]diazepan-1-yl)-benzyl]-methyl-amine; |
| 56 | [5-(4-Cyclopropyl-[1,4]diazepan-1-yl)-2-(3,4-dichloro-phenoxy)-benzyl]-methyl-amine; |
| 57 | 1-Cyclopropyl-4-[3-methylaminomethyl-4-(4-methylsulfanyl-phenoxy)-phenyl]-[1,4]diazepan-5-one; |
| 58 | (S)-Dimethyl-{1-[3-methylaminomethyl-4-(4-methylsulfanyl-phenoxy)-phenyl]-pyrrolidin-3-yl}-amine; |
| 59 | (4-Cyclopropyl-piperazin-1-yl)-[4-(3,4-dichloro-benzyloxy)-3-methylaminomethyl-phenyl]-methanone; |
| 60 | Cyclopropyl-[5-(4-isopropyl-piperazin-1-ylmethyl)-2-(4-methylsulfanyl-phenoxy)-benzyl]-amine; |
| 61 | [5-(4-Isopropyl-piperazin-1-ylmethyl)-2-(4-methylsulfanyl-phenoxy)-benzyl]-methyl-amine; |
| 62 | [5-(4-Isopropyl-piperazin-1-ylmethyl)-2-(4-methylsulfanyl-phenoxy)-benzyl]-dimethyl-amine; |
| 63 | Ethyl-[5-(4-isopropyl-piperazin-1-ylmethyl)-2-(4-methylsulfanyl-phenoxy)-benzyl]-amine; |
| 64 | Isopropyl-[5-(4-isopropyl-piperazin-1-ylmethyl)-2-(4-methylsulfanyl-phenoxy)-benzyl]-amine; |
| 65 | 5-(4-Isopropyl-piperazin-1-ylmethyl)-2-(4-methylsulfanyl-phenoxy)-benzylamine; |
| 66 | 4-[4-(3,4-Dichloro-phenoxy)-3-methylaminomethyl-benzyl]-1-isopropyl-piperazin-2-one; |
| 67 | 1-[4-(3,4-Dichloro-phenoxy)-3-methylaminomethyl-benzyl]-4-isopropyl-piperazin-2-one; |
| 68 | 1-[4-(3,4-Dichloro-phenoxy)-3-methylaminomethyl-benzyl]-4-isopropyl-[1,4]diazepan-5-one; |
| 69 | 4-[4-(3,4-Dichloro-phenoxy)-3-methylaminomethyl-benzyl]-1-isopropyl-[1,4]diazepan-5-one; |
| 70 | 1-Cyclobutyl-4-[4-(3,4-dichloro-phenoxy)-3-methylaminomethyl-benzyl]-[1,4]diazepan-5-one; |
| 71 | 4-(3-Chloro-phenoxy)-3-methylaminomethyl-N-(2-pyrrolidin-1-yl-ethyl)-benzamide; |
| 72 | [4-(3-Chloro-phenoxy)-3-methylaminomethyl-phenyl]-(4-cyclobutyl-piperazin-1-yl)-methanone; |
| 73 | 4-[4-(3,4-Dichloro-phenoxy)-3-methylaminomethyl-phenyl]-1-isopropyl-[1,4]diazepan-5-one; |
| 74 | (4-Cyclobutyl-piperazin-1-yl)-[4-(3,4-dichloro-phenoxy)-3-methylaminomethyl-phenyl]-methanone; |
| 75 | (4-Cyclopentyl-piperazin-1-yl)-[4-(3,4-dichloro-phenoxy)-3-methylaminomethyl-phenyl]-methanone; |
| 76 | [4-(3-Chloro-phenoxy)-3-methylaminomethyl-phenyl]-(4-cyclopentyl-piperazin-1-yl)-methanone; |
| 77 | [4-(4-Chloro-phenoxy)-3-methylaminomethyl-phenyl]-(4-cyclobutyl-piperazin-1-yl)-methanone; |
| 78 | [4-(4-Chloro-phenoxy)-3-methylaminomethyl-phenyl]-(4-cyclopentyl-piperazin-1-yl)-methanone; |

-continued

| Ex. | Compound Name |
|---|---|
| 79 | (4-Isopropyl-piperazin-1-yl)-[3-methylaminomethyl-4-(4-trifluoromethyl-pyridin-2-ylsulfanyl)-phenyl]-methanone; |
| 80 | (4-Cyclopropyl-piperazin-1-yl)-[4-dimethylaminomethyl-3-(2,6-dimethyl-pyridin-3-yloxy)-phenyl]-methanone; |
| 81 | (3-Benzyloxy-4-dimethylaminomethyl-phenyl)-(4-cyclopropyl-piperazin-1-yl)-methanone; |
| 82 | [4-{[Bis-(2-methoxy-ethyl)-amino]-methyl}-3-(2,6-dimethyl-pyridin-3-yloxy)-phenyl]-(4-cyclopropyl-piperazin-1-yl)-methanone; |
| 83 | [3-(2,6-Dimethyl-pyridin-3-yloxy)-4-morpholin-4-ylmethyl-phenyl]-(4-isopropyl-piperazin-1-yl)-methanone; |
| 84 | (4-Dimethylaminomethyl-3-phenoxy-phenyl)-piperidin-1-yl-methanone; |
| 85 | (4-{[Bis-(2-methoxy-ethyl)-amino]-methyl}-3-phenoxy-phenyl)-(4-isopropyl-piperazin-1-yl)-methanone; |
| 86 | [4-{[Bis-(2-methoxy-ethyl)-amino]-methyl}-3-(pyridin-3-yloxy)-phenyl]-(4-dimethylamino-piperidin-1-yl)-methanone; |
| 87 | [4-(4-Isopropyl-piperazin-1-ylmethyl)-3-phenoxy-phenyl]-piperidin-1-yl-methanone; |
| 88 | [4-(4-Isopropyl-piperazin-1-ylmethyl)-3-(pyridin-3-yloxy)-phenyl]-piperidin-1-yl-methanone; |
| 89 | 4-Dimethylaminomethyl-N-(2-methylamino-ethyl)-3-(pyridin-3-yloxy)-benzamide; |
| 90 | N-[2-(Cyclopropyl-methyl-amino)-ethyl]-4-dimethylaminomethyl-3-(pyridin-3-yloxy)-benzamide; and |
| 91 | [5-(4-Isopropyl-piperazine-1-carbonyl)-2-(3-methoxy-phenoxy)-benzyl]-methyl-carbamic acid tert-butyl ester; | and pharmaceutically acceptable salts thereof.

The invention includes also pharmaceutically acceptable salts of the compounds represented by Formula (I), preferably of those described above and of the specific compounds exemplified herein, and methods of treatment using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and Handbook of Pharmaceutical Salts, Properties, Selection, and Use, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$ alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19,115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to pharmaceutically active metabolites of compounds of Formula (I), and uses of such metabolites in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al. *J. Med. Chem.* 1997, 40, 2011-2016; Shan, et al. *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites of the present invention are useful as modulators of the histamine $H_3$ receptor and/or the serotonin transporter in the methods of the invention. Accordingly, the invention relates to methods of using the compounds of the invention to treat subjects diagnosed with or suffering from a disease, disorder, or condition mediated by histamine $H_3$ receptor and/or serotonin transporter activity, such as those described herein.

The term "treat" or "treating" as used herein is intended to refer to administration of a compound or composition of the invention to a subject for the purpose of effecting a therapeutic or prophylactic benefit through modulation of histamine $H_3$ receptor and/or the serotonin transporter activity. Treating includes reversing, ameliorating, alleviating, inhibiting the progress of, lessening the severity of, or preventing a disease, disorder, or condition, or one or more symptoms of such disease, disorder or condition mediated through modulation of histamine $H_3$ receptor and/or the serotonin transporter activity. The term "subject" refers to a mammalian patient in need of such treatment, such as a human. "Modulators" include both inhibitors and activators, where "inhibitors" refer to compounds that decrease, prevent, inactivate, desensitize or down-regulate histamine $H_3$ receptor and/or the serotonin transporter expression or activity, and "activators" are compounds that increase, activate, facilitate, sensitize, or up-regulate histamine $H_3$ receptor and/or the serotonin transporter expression or activity.

Accordingly, the invention relates to methods of using the compounds described herein to treat subjects diagnosed with or suffering from a disease, disorder, or condition mediated by histamine $H_3$ receptor and/or the serotonin transporter activity, such as: cognitive disorders, sleep disorders, psychiatric disorders, and other disorders. Symptoms or disease states are intended to be included within the scope of "medical conditions, disorders, or diseases."

Cognitive disorders include, for example, dementia, Alzheimer's disease (Panula, P. et al., Soc. Neurosci. Abstr. 1995, 21, 1977), cognitive dysfunction, mild cognitive impairment (pre-dementia), attention deficit hyperactivity disorders (ADHD), attention-deficit disorders, and learning and memory disorders (Barnes, J. C. et al., Soc. Neurosci. Abstr. 1993, 19, 1813). Learning and memory disorders include, for example, learning impairment, memory impairment, age-related cognitive decline, and memory loss. $H_3$ antagonists have been shown to improve memory in a variety of memory tests, including the elevated plus maze in mice (Miyazaki, S. et al. *Life Sci.* 1995, 57(23), 2137-2144), a two-trial place recognition task (Orsetti, M. et al. *Behav. Brain Res.* 2001, 124(2), 235-242), the passive avoidance test in mice (Miyazaki, S. et al. *Meth. Find. Exp. Clin. Pharmacol.* 1995, 17(10), 653-658) and the radial maze in rats (Chen, Z. *Acta Pharmacol. Sin.* 2000, 21(10), 905-910). Also, in the spontaneously hypertensive rat, an animal model for the learning impairments in attention-deficit disorders, $H_3$ antagonists were shown to improve memory (Fox, G. B. et al. *Behav. Brain Res.* 2002, 131(1-2), 151-161).

Sleep disorders include, for example, insomnia, disturbed sleep, narcolepsy (with or without associated cataplexy), cataplexy, disorders of sleep/wake homeostasis, idiopathic somnolence, excessive daytime sleepiness (EDS), circadian rhythm disorders, fatigue, lethargy, jet lag, and REM-behavioral disorder. Fatigue and/or sleep impairment may be caused by or associated with various sources, such as, for example, sleep apnea, perimenopausal hormonal shifts, Parkinson's disease, multiple sclerosis (MS), depression, chemotherapy, or shift work schedules.

Psychiatric disorders include, for example, schizophrenia (Schlicker, E. and Marr, I., Naunyn-Schmiedeberg's Arch. Pharmacol. 1996, 353, 290-294), bipolar disorders, manic disorders, depression (Lamberti, C. et al. *Br. J. Pharmacol.* 1998, 123(7), 1331-1336; Perez-Garcia, C. et al. *Psychopharmacology* 1999, 142(2), 215-220) (Also see: Stark, H. et al., Drugs Future 1996, 21(5), 507-520; and Leurs, R. et al., Prog. Drug Res. 1995, 45, 107-165 and references cited therein), obsessive-compulsive disorder, and post-traumatic stress disorder.

Other disorders include, for example, motion sickness, vertigo (e.g. vertigo or benign postural vertigo), epilepsy (Yokoyama, H. et al., Eur. J. Pharmacol. 1993, 234, 129-133), migraine, neurogenic inflammation, eating disorders (Machidori, H. et al., Brain Res. 1992, 590, 180-186), obesity, substance abuse disorders, tinnitus, movement disorders (e.g. restless leg syndrome), eye-related disorders (e.g. macular degeneration and retinitis pigmentosis), and sexual dysfunction (including premature ejaculation).

Particularly, as modulators of the histamine $H_3$ receptor and/or the serotonin transporter, the compounds of the present invention are useful in the treatment or prevention of depression, disturbed sleep, narcolepsy, fatigue, lethargy, cognitive impairment, memory impairment, memory loss, learning impairment, attention-deficit disorders, and eating disorders.

In a treatment method according to the invention, an effective amount of a compound according to the invention is administered to a subject suffering from or diagnosed as having such a disease, disorder, or condition. An "effective amount" means an amount or dose sufficient to generally bring about the desired therapeutic or prophylactic benefit in patients in need of such treatment.

Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.001 to about 200 mg of compound per kg of subject's body weight per day, preferably about 0.05 to 100 mg/kg/day, or about 1 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. In an exemplary embodiment, additional active ingredients are those that are known or discovered to be effective in the treatment of conditions, disorders, or diseases mediated by histamine $H_3$ receptor and/or the serotonin transporter activity or that are active against another target associated with the particular condition, disorder, or disease, such as $H_1$ receptor antagonists, $H_2$ receptor antagonists, $H_3$ receptor antagonists, topiramate (Topamax™), and neurotransmitter modulators such as serotonin-norepinephrine reuptake inhibitors, selective serotonin reuptake inhibitors (SSRIs), noradrenergic reuptake inhibitors, non-selective serotonin re-uptake inhibitors (NSSRIs), acetylcholinesterase inhibitors (such as tetrahydroaminoacridine, Donepezil (Aricept™), Rivastigmine, or Galantamine (Reminyl™)), or modafinil. The combination may serve to increase efficacy (e.g., by including in the combination a compound potentiating the potency or effectiveness of a compound according to the invention), decrease one or more side effects, or decrease the required dose of the compound according to the invention.

More particularly, compounds of the invention in combination with modafinil are useful for the treatment of narcolepsy, excessive daytime sleepiness (EDS), Alzheimer's disease, depression, attention-deficit disorders, MS-related fatigue, post-anesthesia grogginess, cognitive impairment, schizophrenia, spasticity associated with cerebral palsy, age-related memory decline, idiopathic somnolence, or jet-lag. Preferably, the combination method employs doses of modafinil in the range of about 20 to 300 mg per dose.

The compounds of the invention are used, alone or in combination with one or more other active ingredients, to formulate pharmaceutical compositions of the invention. A pharmaceutical composition of the invention comprises: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a compound of the invention and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the compounds of the invention may be prepared using suitable pharmaceutical excipients and compounding techniques now or later known or available to those skilled in the art. The compositions may be administered in the inventive methods by oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil, sesame oil, or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compounds of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Reactions may be performed between the melting point and the reflux temperature of the solvent, and preferably between 0° C. and the reflux temperature of the solvent. Unless otherwise specified, the variables are as defined above in reference to Formula (I).

| Table of Acronyms and Abbreviations | |
|---|---|
| Term | Acronym or Abbreviation |
| tert-Butoxycarbonyl | Boc |
| 1,8-Diazabicyclo[5.4.0]undec-7-ene | DBU |
| 1,2-Dichloroethane | DCE |
| Dichloromethane | DCM |
| Diethyl azodicarboxylate | DEAD |
| Diisopropyl azodicarboxylate | DIAD |
| Ethylene glycol dimethyl ether | DME |
| N,N-Dimethylformamide | DMF |
| Diethyl ether | Et$_2$O |
| Ethyl acetate | EtOAc |
| Ethanol | EtOH |

-continued

| Table of Acronyms and Abbreviations | |
|---|---|
| Term | Acronym or Abbreviation |
| Methanol | MeOH |
| Tetrahydrofuran | THF |
| Trifluoroacetic acid | TFA |

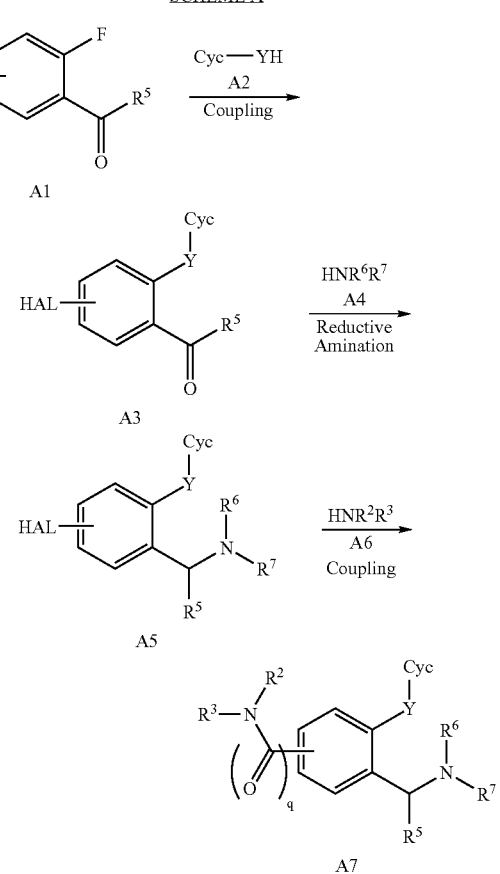

Referring to Scheme A, fluorobenzenes A1, where HAL is Br or Cl, are commercially available or are prepared according to methods known to one skilled in the art. Aromatic substitution of compounds A1 with reagents Cyc-YH, where Y is —O— or —S—, in the presence of a suitable base such as K$_2$CO$_3$, Na$_2$CO$_3$, or Cs$_2$CO$_3$, in a solvent such as DMF, DME, or toluene, or a mixture thereof, at temperatures between room temperature and the reflux temperature of the solvent, provides ethers and thioethers A3. Ethers and thioethers A3 are reacted with amines A4 to form benzyl amines A5 under reductive amination conditions known to one skilled in the art. Preferred conditions include a reducing agent such as NaBH$_4$, NaCNBH$_3$, or NaBH(OAc)$_3$, in a solvent such as MeOH, EtOH, or DCE, and with optional additives such as acetic acid or a Lewis acid. Where a primary amine H$_2$NR$^7$ is used for the reductive amination, the resulting benzyl amine may be protected in a subsequent step with a suitable nitrogen protecting group, such as a Boc or other suitable carbamoyl group, under conditions known to one skilled in the art. Coupling with amines A6 is accomplished using two methods. First, aryl amination with amines A6, in the presence of a palladium catalyst such as (PPh$_3$)$_2$PdCl$_2$ or Pd$_2$(dba)$_3$, a phosphine ligand such as 2-dicyclohexylphosphino-2',4',6'-triisopropylbiphenyl (XPHOS), and a base such as tBuONa, in a solvent such as DMF, DME, or toluene, at temperatures between room temperature and the reflux temperature of the solvent, provides anilines A7 (where q is 0). Aminocarbonylation of aryl bromides A5 with amines A6 to give amides A7 (where q is 1) may be performed in the presence of a suitable catalyst, such as Hermann's catalyst (trans-di-μ-acetatobis[2-(di-o-tolylphosphino)benzyl]-dipalladium), coupling aids such as tri-t-butylphosphonium tetrafluoroborate, a CO equivalent such as Mo(CO)$_6$, a suitable base such as DBU, in a solvent such as THF or toluene, at temperatures between room temperature and 150° C. in a microwave reactor. If a nitrogen protecting group is used, removal is accomplished under conditions known in the art, such as acidic or hydrogenation conditions, following the coupling step. Where the synthesis provides compounds where Y is —S—, oxidation to the corresponding sulfoxides and sulfones (Y is —SO— or —SO$_2$—) may be performed under conditions known in the art.

where where Y is —O— or —S—. All such ethers and thioethers A5 may be processed into compounds of Formula (I) as described in Scheme A.

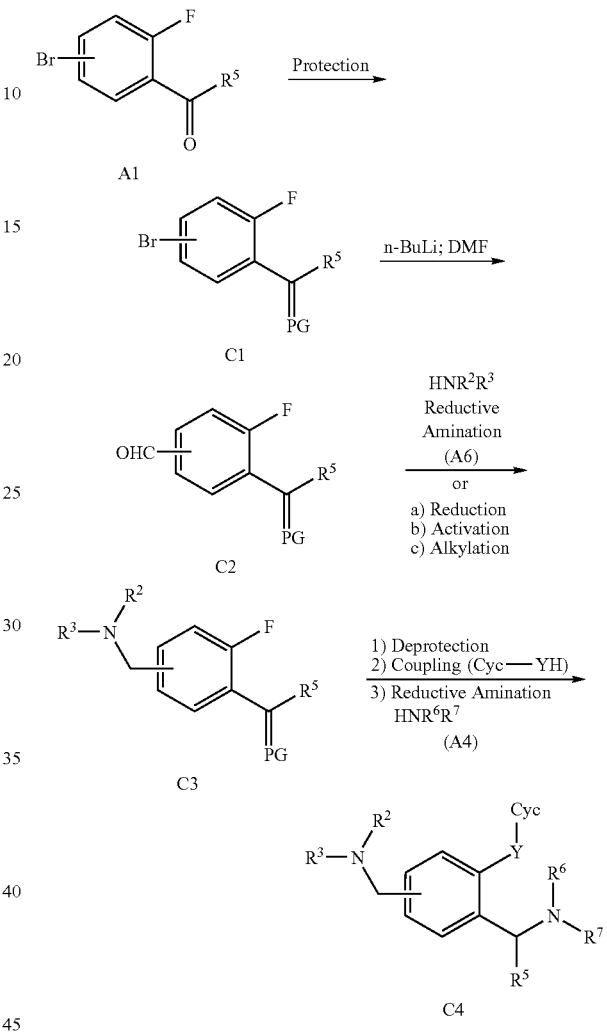

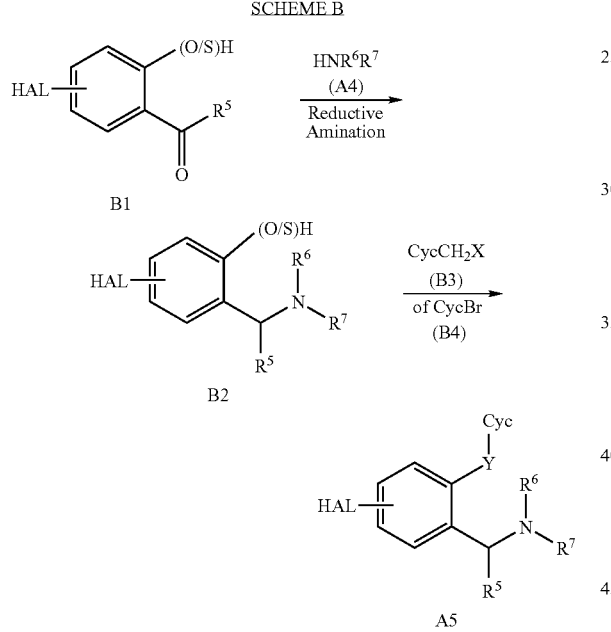

Referring to Scheme B, phenols or thiophenols B1 may be converted to amines B2 by reductive amination methods as described in Scheme A. Alkylation of phenols and thiols B2 with CycCH$_2$X (where X is a suitable leaving group, such as Br, Cl, OTs, or the like), in the presence of a suitable base such as K$_2$CO$_3$, Na$_2$CO$_3$, NaH, or the like, in a solvent such as CH$_3$CN or THF, provides ethers and thioethers A5, where Y is —O— or —S—. In another embodiment, phenols or thiophenols B2 may be reacted under Mitsunobu conditions with CycCH$_2$X, where X is OH or SH, in the presence of PPh$_3$ and DEAD or DIAD, in a solvent such as CH$_3$CN or THF, to form ethers and thioethers A5, where Y is —OCH$_2$—. Aromatic substitution with activated CycBr reagents (where Cyc is a suitable heteroaryl group) may be accomplished in the presence of a suitable base such as K$_2$CO$_3$, Na$_2$CO$_3$, or Cs$_2$CO$_3$, in the presence of dehydryating agents such as molecular sieves or Ca$_2$O or a mixture thereof, and salicylaldoxime, in a solvent such as DMF, DME, or toluene, or a mixture thereof, at temperatures between room temperature and the reflux temperature of the solvent, to form ethers or thioethers A5

Compounds of Formula (I) may also be prepared according to Scheme C. The carbonyl functionality of aryl bromides A1 is protected with a suitable protecting group, such as an acetal or ketal, using methods known in the art. Aldehydes are preferably protected by treatment with ethylene glycol and a catalyst such as p-toluenesulfonic acid, in a solvent such as benzene or toluene, preferably at reflux temperature. Removal of water is accomplished with molecular sieves or a Dean-Stark trap. The resulting bromides C1 are converted to benzaldehydes C2 by halogen-metal exchange with an organolithium reagent such as n-BuLi, in a solvent such as THF or Et$_2$O, and trapping of the resultant lithium anion with DMF. Reductive amination with amines A6 using methods as described in Scheme A provides benzyl amines C3. Aldehydes C2 may alternatively be reduced to the corresponding benzyl alcohols, activated (e.g., as a benzyl chloride, bromide, or tosylate), and displaced with suitable reagents A6 to provide benzyl amines C3. The carbonyl group may be deprotected, such as with 6 N HCl, and subsequent coupling with Cyc-YH and reductive amination as in Scheme A gives rise to compounds C4. One skilled in the art will recognize that this Scheme may also be accomplished with phenols and thiols rather than fluorobenzenes A1 to access compounds where Y is —OCH$_2$— and where Cyc is a suitable heteroaryl group.

Those skilled in the art will recognize that several of the chemical transformations described above may be performed in a different order than that depicted in the above Schemes. In addition, one skilled in the art will recognize that compounds of formulae A7 and C4 are compounds of Formula (I).

Additional applicable methodologies are described in U.S. Pat. Publ. US 2006/0194837 A1, U.S. Pat. Publ. US 2006/0293316 A1, and U.S. Pat. Publ. US 2006/0287292 A1.

Compounds of Formula (I) may be converted to their corresponding salts using methods known to those skilled in the art. For example, amines of Formula (I) may be treated with trifluoroacetic acid, HCl, or citric acid in a solvent such as Et$_2$O, DCM, THF, or MeOH to provide the corresponding salt forms.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following examples are provided to further illustrate the invention and various preferred embodiments.

EXAMPLES

Chemistry:

Where solutions or mixtures are "concentrated", they are typically concentrated under reduced pressure using a rotary evaporator.

Normal phase flash column chromatography (FCC) was typically performed with RediSep® silica gel columns using 2 M NH$_3$ in MeOH/DCM as eluent, unless otherwise indicated.

Preparative Reversed-Phase high performance liquid chromatography (HPLC) was typically performed using a Gilson® instrument with a YMC-Pack ODS-A, 5 μm, 75×30 mm column, a flow rate of 25 mL/min, detection at 220 and 254 nm, with a 15% to 99% acetonitrile/water/0.05% TFA gradient.

Analytical Reversed-Phase HPLC was typically performed using 1) a Hewlett Packard Series 1100 instrument with an Agilent ZORBAX® Bonus RP, 5 μm, 4.6×250 mm column, a flow rate of 1 mL/min, detection at 220 and 254 nm, with a 1% to 99% acetonitrile/water/0.05% TFA gradient; or 2) a Hewlett Packard HPLC instrument with an Agilent ZORBAX® Eclipse XDB-C8, 5 μm, 4.6×150 mm column, a flow rate of 1 mL/min, detection at 220 and 254 nm, with a 1% to 99% acetonitrile/water/0.05% TFA gradient.

Where trifluoroacetic acid salts were obtained, they were obtained from preparative reversed-phase HPLC or from deprotection of a Boc group with TFA in a final step. Where hydrochloride salts were obtained, they were obtained by treatment of a solution of the corresponding free base in DCM with an excess of 2.5 M HCl in MeOH, and concentration of the reaction solution.

In obtaining the characterization data described in the examples below, the following analytical protocols were followed as indicated.

Mass spectra were obtained on an Agilent series 1100 MSD using electrospray ionization (ESI) in either positive or negative modes as indicated. Calculated mass corresponds to the exact mass.

NMR spectra were obtained on either a Bruker model DPX400 (400 MHz), DPX500 (500 MHz), DRX600 (600 MHz) spectrometer. The format of the $^1$H NMR data below is: chemical shift in ppm down field of the tetramethylsilane reference (multiplicity, coupling constant J in Hz, integration).

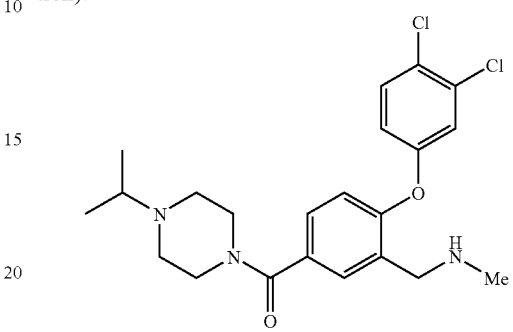

Example 1

[4-(3,4-Dichloro-phenoxy)-3-methylaminomethyl-phenyl]-(4-isopropyl-piperazin-1-yl)-methanone Step A: 5-Bromo-2-(3,4-dichloro-phenoxy)-benzaldehyde. To a solution of 5-bromo-2-fluoro-benzaldehyde (5.13 g, 25.4 mmol) in DMF (25 mL) were added K$_2$CO$_3$ (7.15 g, 51.8 mmol) and 3,4-dichloro-phenol (4.67 g, 28.8 mmol). The mixture was heated at 90° C. for 24 h and then was allowed to cool to room temperature (rt). Water was added and the mixture was extracted with Et$_2$O. The combined organic layers were dried (MgSO$_4$) and concentrated. The residue was diluted with DCM and hexanes and the resulting solids were collected by vacuum filtration to provide the desired product (4.74 g, 54%). $^1$H NMR (CDCl$_3$): 10.36 (s, 1H), 8.06 (d, J=2.5, 1H), 7.67 (dd, J=8.8, 2.6, 1H), 7.46 (d, J=8.8, 1H), 7.17 (d, J=2.8, 1H), 6.92 (dd, J=8.8, 2.8, 1H), 6.84 (d, J=8.8, 1H).

Step B: [5-Bromo-2-(3,4-dichloro-phenoxy)-benzyl]-methyl-amine. To a mixture of 5-bromo-2-(3,4-dichloro-phenoxy)-benzaldehyde (4.74 g, 13.8 mmol) in MeOH (250 mL) was added MeNH$_2$ (40% aq.; 20 mL, 260 mmol), and the resulting mixture was stirred at rt until homogeneous. The mixture was cooled to 0° C. and treated with NaBH$_4$ (1.05 g, 27.8 mmol) portionwise. After 24 h, the mixture was concentrated and the residue was diluted with 1 N NaOH and extracted with DCM. The combined organic layers were dried (Na$_2$SO$_4$) and concentrated. The crude product was purified by FCC to provide the desired product (4.80 g, 97%). MS (ESI): mass calcd. for C$_{14}$H$_{12}$BrCl$_2$NO, 358.95; m/z found, 360.1 [M+H]$^+$. $^1$H NMR (CDCl$_3$): 7.61 (d, J=2.5, 1H), 7.40-7.37 (m, 2H), 7.03 (d, J=2.8, 1H), 6.82-6.79 (m, 2H), 3.72 (s, 2H), 2.44 (s, 3H), 1.30-1.21 (m, 1H).

Step C: [5-Bromo-2-(3,4-dichloro-phenoxy)-benzyl]-methyl-carbamic acid tert-butyl ester. To a solution of [5-bromo-2-(3,4-dichloro-phenoxy)-benzyl]-methyl-amine (4.61 g, 12.8 mmol) in DCM (250 mL) were added Et$_3$N (3.6 mL, 25.8 mmol) and di-tert-butyl dicarbonate (3.44 g, 15.8 mmol). After 1 h, the mixture was diluted with 1 N NaOH and extracted with DCM. The combined organic layers were dried (Na$_2$SO$_4$) and concentrated. The crude material was carried forward without purification (6.35 g, >100%). $^1$H NMR (CDCl$_3$): 7.47-7.31 (m, 3H), 7.03 (d, J=2.8, 1H), 6.80-6.74 (m, 2H), 4.46-4.32 (m, 2H), 2.93-2.78 (m, 3H), 1.45 (br s, 9H).

Step D. [2-(3,4-Dichloro-phenoxy)-5-(4-isopropyl-piperazine-1-carbonyl)-benzyl]-methyl-carbamic acid tert-butyl ester. To a solution of [5-bromo-2-(3,4-dichloro-phenoxy)-benzyl]-carbamic acid tert-butyl ester (327.0 mg, 0.71 mmol) in THF (2 mL) were added DBU (0.30 mL, 2.0 mmol), 1-isopropyl piperazine (0.30 mL, 2.5 mmol), Hermann's catalyst (31.9 mg, 0.034 mmol), tri-t-butylphosphium tetrafluoroborate (26.4 mg, 0.091 mmol), and $Mo(CO)_6$ (211.0 mg, 0.80 mmol). After 6 min in a microwave reactor at 125° C., the mixture was cooled to rt and concentrated. Purification by FCC gave the desired product (212.5 mg, 56%).

Step E. To a solution of [2-(3,4-dichloro-phenoxy)-5-(4-isopropyl-piperazine-1-carbonyl)-benzyl]-methyl-carbamic acid tert-butyl ester (212.5 mg, 0.40 mmol) in DCM (2 mL) was added TFA (1 mL). After 30 min, the mixture was concentrated and the residue was purified by FCC to give the desired product (119.3 mg, 69%). MS (ESI): mass calcd. for $C_{22}H_{27}Cl_2N_3O_2$, 435.15; m/z found, 436.3 $[M+H]^+$. $^1H$ NMR ($CDCl_3$): 7.50 (d, J=2.0, 1H), 7.38 (d, J=8.8, 1H), 7.30 (dd, J=8.3, 2.1, 1H), 7.06 (d, J=2.8, 1H), 6.88 (d, J=8.3, 1H), 6.82 (dd, J=8.8, 2.8, 1H), 3.81-3.69 (m, 4H), 3.53-3.37 (m, 2H), 2.78-2.68 (m, 1H), 2.64-2.43 (m, 4H), 2.43 (s, 3H), 1.93 (br s, 1H), 1.04 (d, J=6.5, 6H).

The compounds in Examples 2-27 were prepared by a sequence similar to that described in Example 1.

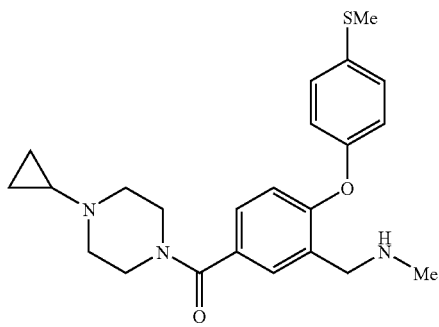

Example 2

(4-Cyclopropyl-piperazin-1-yl)-[3-methylaminomethyl-4-(4-methylsulfanyl-phenoxy)-phenyl]-methanone MS (ESI): mass calcd. for $C_{23}H_{29}N_3O_2S$, 411.20; m/z found, 412.3 $[M+H]^+$. $^1H$ NMR ($CDCl_3$): 7.49 (d, J=2.1, 1H), 7.30-7.26 (m, 3H), 6.94 (d, J=8.7, 2H), 6.85 (d, J=8.3, 1H), 3.83 (s, 2H), 3.80-3.68 (m, 2H), 3.51-3.38 (m, 2H), 2.72-2.54 (m, 4H), 2.50 (s, 3H), 2.47 (s, 3H), 2.04 (s, 2H), 1.68-1.64 (m, 1H), 1.63-1.55 (m, 3H).

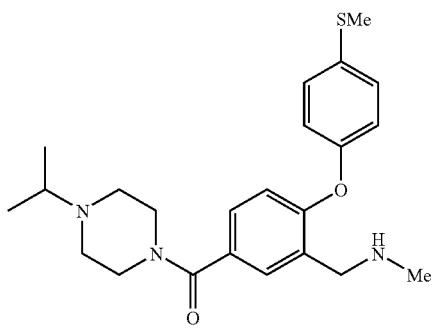

Example 3

(4-Isopropyl-piperazin-1-yl)-[3-methylaminomethyl-4-(4-methylsulfanyl-phenoxy)-phenyl]-methanone MS (ESI): mass calcd. for $C_{23}H_{31}N_3O_2S$, 413.21; m/z found, 414.4 $[M+H]^+$. $^1H$ NMR ($CDCl_3$): 7.47 (d, J=2.1, 1H), 7.30-7.24 (m, 3H), 6.93 (d, J=8.8, 2H), 6.83 (d, J=8.3, 1H), 3.81 (s, 2H), 3.81-3.70 (m, 2H), 3.56-3.40 (m, 2H), 2.77-2.68 (m, 1H), 2.63-2.44 (m, 4H), 2.48 (s, 3H), 2.45 (s, 3H), 1.56 (br s, 1H), 1.05 (d, J=6.5, 6H).

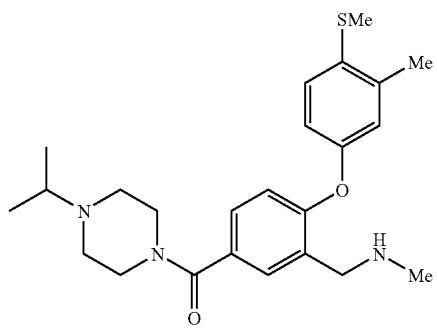

Example 4

(4-Isopropyl-piperazin-1-yl)-[3-methylaminomethyl-4-(3-methyl-4-methylsulfanyl-phenoxy)-phenyl]-methanone $^1H$ NMR ($CDCl_3$): 7.47 (d, J=2.0, 1H), 7.26 (dd, J=8.3, 2.1, 1H), 7.17 (d, J=9.3, 1H), 6.84-6.80 (m, 3H), 3.83 (s, 2H), 3.82-3.70 (m, 2H), 3.56-3.41 (m, 2H), 2.77-2.70 (m, 1H), 2.64-2.47 (m, 4H), 2.46 (s, 3H), 2.45 (s, 3H), 2.34 (s, 3H), 2.04 (br s, 1H), 1.05 (d, J=6.5, 6H).

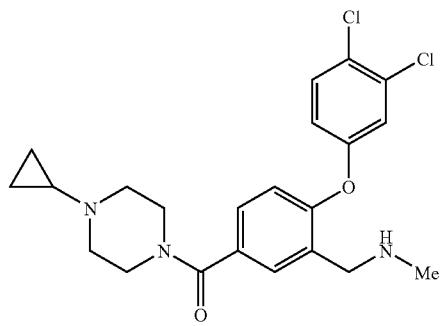

Example 5

(4-Cyclopropyl-piperazin-1-yl)-[4-(3,4-dichloro-phenoxy)-3-methylaminomethyl-phenyl]-methanone MS (ESI): mass calcd. for $C_{22}H_{25}Cl_2N_3O_2$, 433.13; m/z found, 434.2 $[M+H]^+$. $^1H$ NMR ($CDCl_3$): 7.51 (d, J=2.0, 1H), 7.38 (d, J=8.8, 1H), 7.30 (dd, J=8.3, 2.1, 1H), 7.06 (d, J=2.8, 1H), 6.88 (d, J=8.3, 1H), 6.83 (dd, J=8.8, 2.8, 1H), 3.79-3.63 (m, 4H), 3.50-3.31 (m, 2H), 2.75-2.50 (m, 4H), 2.44 (s, 3H), 1.99 (br s, 1H), 1.67-1.60 (m, 1H), 0.50-0.38 (m, 4H).

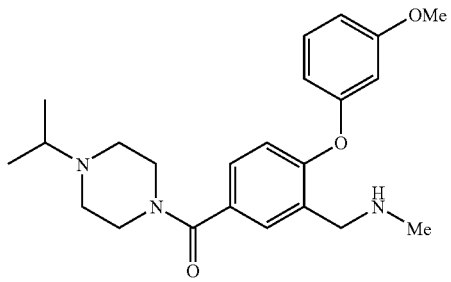

Example 6

(4-Isopropyl-piperazin-1-yl)-[4-(3-methoxy-phenoxy)-3-methylaminomethyl-phenyl]-methanone $^1$H NMR (CDCl$_3$): 7.47 (d, J=2.1, 1H), 7.29-7.21 (m, 2H), 6.89 (d, J=8.3, 1H), 6.70-6.66 (m, 1H), 6.57-6.53 (m, 2H), 3.83 (s, 2H), 3.79 (s, 3H), 3.55-3.44 (m, 1H), 2.77-2.69 (m, 1H), 2.64-2.47 (m, 3H), 2.46 (s, 3H), 1.75-1.63 (m, 5H), 1.05 (d, J=6.5, 6H).

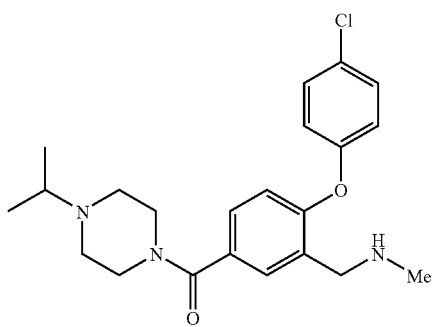

Example 7

[4-(4-Chloro-phenoxy)-3-methylaminomethyl-phenyl]-(4-isopropyl-piperazin-1-yl)-methanone $^1$H NMR (CDCl$_3$): 7.51 (d, J=2.1, 1H), 7.32 (d, J=8.9, 2H), 7.30-7.26 (m, 1H), 6.93 (d, J=8.9, 2H), 6.86 (d, J=8.3, 1H), 3.83 (s, 2H), 3.83-3.68 (m, 2H), 3.59-3.40 (m, 2H), 2.78-2.72 (m, 1H), 2.66-2.47 (m, 4H), 2.47 (s, 3H), 1.75 (br s, 1H), 1.07 (d, J=6.5, 6H).

Example 8

[4-(4-Chloro-phenoxy)-3-cyclopropylaminomethyl-phenyl]-(4-isopropyl-piperazin-1-yl)-methanone MS (ESI): mass calcd. for C$_{24}$H$_{30}$ClN$_3$O$_2$, 427.20; m/z found, 428.3 [M+H]$^+$. $^1$H NMR (CDCl$_3$): 7.48 (d, J=2.0, 1H), 7.33-7.24 (m, 3H), 6.92 (d, J=9.3, 2H), 6.84 (d, J=8.3, 1H), 3.89 (s, 2H), 3.83-3.42 (m, 4H), 2.78-2.69 (m, 1H), 2.63-2.43 (m, 4H), 2.15-2.09 (m, 1H), 1.05 (d, J=6.5, 6H), 0.45-0.34 (m, 4H).

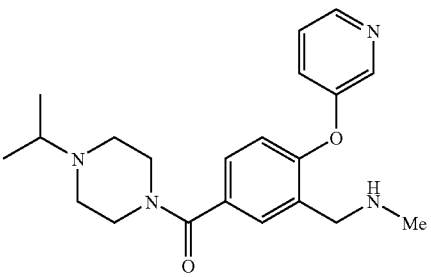

Example 9

(4-Isopropyl-piperazin-1-yl)-[3-methylaminomethyl-4-(pyridin-3-yloxy)-phenyl]-methanone MS (ESI): mass calcd. for C$_{21}$H$_{28}$N$_4$O$_2$, 368.22; m/z found, 369.4 [M+H]$^+$. $^1$H NMR (MeOD): 8.90-8.86 (m, 1H), 8.74 (d, J=5.3, 1H), 8.39-8.35 (m, 1H), 8.12-8.07 (m, 1H), 7.84 (d, J=1.9, 1H), 7.67 (dd, J=8.5, 2.0, 1H), 7.23 (d, J=8.5, 1H), 4.98-4.58 (m, 1H), 4.42 (s, 2H), 4.27-3.96 (m, 1H), 3.74-3.96 (m, 1H), 3.74-3.35 (m, 5H), 3.30-3.22 (m, 2H), 2.84 (s, 3H), 1.41 (d, J=6.7, 6H).

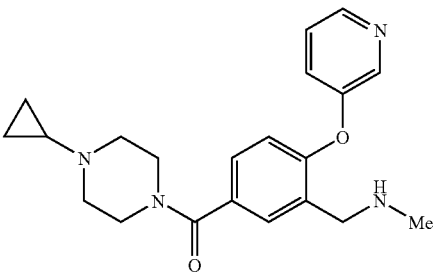

Example 10

(4-Cyclopropyl-piperazin-1-yl)-[3-methylaminomethyl-4-(pyridin-3-yloxy)-phenyl]-methanone MS (ESI): mass calcd. for C$_{21}$H$_{26}$N$_4$O$_2$, 366.21; m/z found, 367.4 [M+H]$^+$. $^1$H NMR (MeOD): 8.83 (s, 1H), 8.71 (d, J=5.1, 1H), 8.30-8.26 (m, 1H), 8.04-8.00 (m, 1H), 7.82 (d, J=2.1, 1H), 7.60 (dd, J=8.5, 2.1, 1H), 7.20 (d, J=8.5, 1H), 4.42 (s, 2H), 4.18-3.65 (m, 4H), 2.99-2.88 (m, 1H), 2.84 (s, 3H), 1.43 (d, J=12.7, 3H), 1.15-1.11 (m, 2H), 1.02-0.97 (m, 2H).

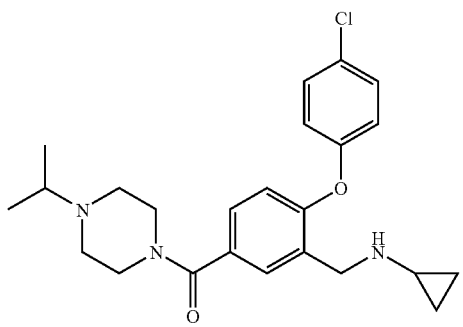

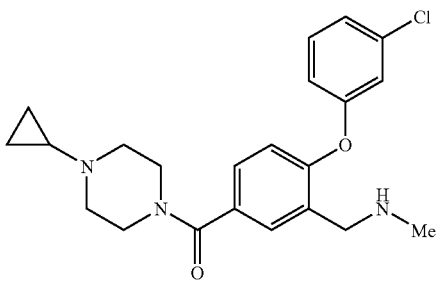

Example 11

[4-(3-Chloro-phenoxy)-3-methylaminomethyl-phenyl]-(4-cyclopropyl-piperazin-1-yl)-methanone MS (ESI): mass calcd. for $C_{22}H_{26}ClN_3O_2$, 399.17; m/z found, 400.3 [M+H]+. $^1$H NMR (CDCl$_3$): 7.68 (d, J=2.0, 1H), 7.40-7.34 (m, 2H), 7.26-7.23 (m, 1H), 7.08 (t, J=2.1, 1H), 6.96 (ddd, J=8.2, 2.3, 0.92, 1H), 6.82 (d, J=8.5, 1H), 4.32-4.27 (m, 2H), 4.18-2.98 (m, 7H), 2.79 (s, 3H), 2.57-2.49 (m, 1H), 1.27-1.19 (m, 3H), 0.93-0.82 (m, 2H).

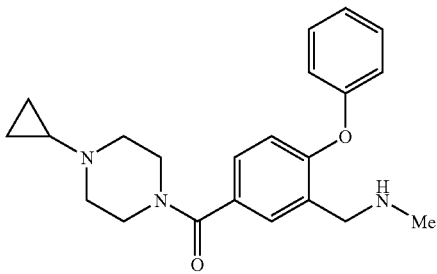

Example 12

(4-Cyclopropyl-piperazin-1-yl)-(3-methylaminomethyl-4-phenoxy-phenyl)-methanone

MS (ESI): mass calcd. for $C_{22}H_{27}N_3O_2$, 365.21; m/z found, 366.3 [M+H]+. $^1$H NMR (CDCl$_3$): 7.48 (d, J=2.1, 1H), 7.38-7.33 (m, 2H), 7.28-7.25 (m, 1H), 7.16-7.11 (m, 1H), 7.01-6.97 (m, 2H), 6.85 (d, J=8.3, 1H), 3.83 (s, 2H), 3.81-3.66 (m, 2H), 3.52-3.38 (m, 2H), 2.74-2.52 (m, 4H), 2.45 (s, 3H), 1.68-1.62 (m, 1H), 0.51-0.46 (m, 2H), 0.46-0.40 (m, 2H).

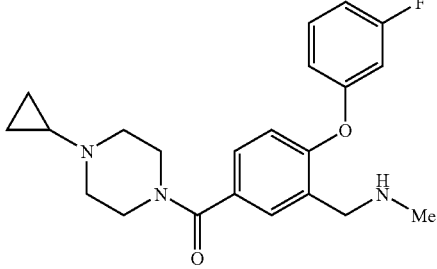

Example 13

(4-Cyclopropyl-piperazin-1-yl)-[4-(3-fluoro-phenoxy)-3-methylaminomethyl-phenyl]-methanone MS (ESI): mass calcd. for $C_{22}H_{26}FN_3O_2$, 383.20; m/z found, 384.40 [M+H]+. $^1$H NMR (CDCl$_3$): 7.54 (d, J=2.2, 1H), 7.33-7.27 (m, 2H), 6.91 (d, J=8.4, 1H), 6.87-6.81 (m, 1H), 6.80-6.76 (m, 1H), 6.72 (tt, J=10.0, 2.4, 1H), 3.86 (br s, 2H), 3.81-3.64 (m, 2H), 3.55-3.32 (m, 2H), 2.75-2.50 (m, 4H), 2.48 (s, 3H), 1.70-1.59 (m, 1H), 0.52-0.38 (m, 4H).

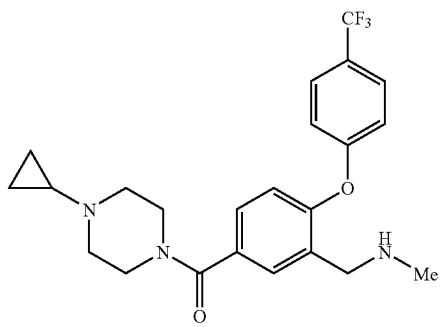

Example 14

(4-Cyclopropyl-piperazin-1-yl)-[3-methylaminomethyl-4-(4-trifluoromethyl-phenoxy)-phenyl]-methanone MS (ESI): mass calcd. for $C_{23}H_{26}F_3N_3O_2$, 433.20; m/z found, 434.4 [M+H]+. $^1$H NMR (CDCl$_3$): 7.64-7.56 (m, 2H), 7.56-7.52 (m, 1H), 7.32 (dd, J=8.2, 2.2, 1H), 7.06-7.01 (m, 2H), 6.94 (d, J=8.2, 1H), 3.83-3.63 (m, 4H), 3.54-3.33 (m, 2H), 2.78-2.50 (m, 4H), 2.44 (s, 3H), 1.78-1.56 (m, 1H), 0.54-0.38 (m, 4H).

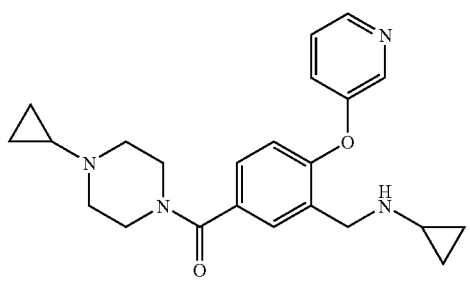

Example 15

[3-Cyclopropylaminomethyl-4-(pyridin-3-yloxy)-phenyl]-(4-cyclopropyl-piperazin-1-yl)-methanone MS (ESI): mass calcd. for $C_{23}H_{28}N_4O_2$, 392.22; m/z found, 393.4 [M+H]+. $^1$H NMR (MeOD): 8.82 (d, J=2.5, 1H), 8.68 (d, J=5.4, 1H), 8.30 (dd, J=8.7, 1.6, 1H), 8.05-8.01 (m, 1H), 7.80 (d, J=1.9, 1H), 7.62 (dd, J=8.5, 2.0, 1H), 7.18 (d, J=8.5, 1H), 4.48 (s, 2H), 4.00-3.31 (m, 6H), 2.89-2.80 (m, 2H), 1.38 (d, J=12.8, 2H), 1.10-1.05 (m, 2H), 0.96-0.86 (m, 6H).

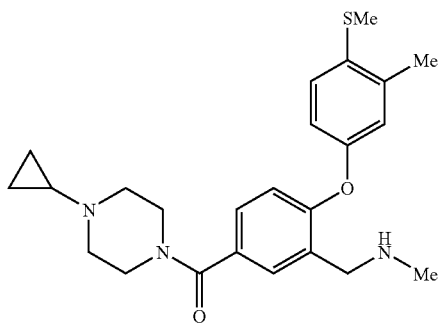

Example 16

(4-Cyclopropyl-piperazin-1-yl)-[3-methylaminomethyl-4-(3-methyl-4-methylsulfanyl-phenoxy)-phenyl]-methanone MS (ESI): mass calcd. for $C_{24}H_{31}N_3O_2S$, 425.21; m/z found, 426.4 [M+H]$^+$. $^1$H NMR (CDCl$_3$): 7.47 (d, J=2.1, 1H), 7.27-7.24 (m, 2H), 7.19-7.16 (m, 1H), 6.84-6.81 (m, 3H), 3.83 (s, 2H), 3.80-3.86 (m, 2H), 3.53-3.33 (m, 2H), 2.74-2.51 (m, 4H), 2.47-2.46 (m, 3H), 2.45 (s, 3H), 2.34 (s, 3H), 1.89-1.80 (m, 3H), 1.68-1.61 (m, 1H).

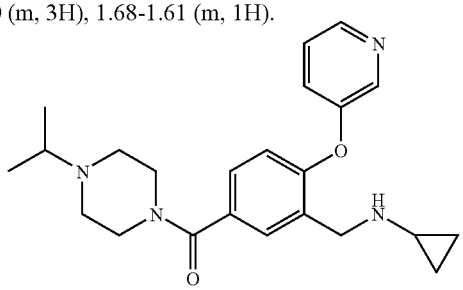

Example 17

[3-Cyclopropylaminomethyl-4-(pyridin-3-yloxy)-phenyl]-(4-isopropyl-piperazin-1-yl)-methanone MS (ESI): mass calcd. for $C_{23}H_{30}N_4O_2$, 394.24; m/z found, 395.4 [M+H]$^+$. $^1$H NMR (CDCl$_3$): 8.83 (br s, 1H), 8.70 (br s, 1H), 8.27-8.24 (m, 1H), 8.03-7.98 (m, 1H), 7.85-7.83 (m, 1H), 7.67 (dd, J=8.5, 2.0, 1H), 7.20 (d, J=8.5, 1H), 4.91-4.65 (m, 1H), 4.53 (s, 2H), 4.24-3.95 (m, 1H), 3.70-3.38 (m, 5H), 3.28-3.19 (m, 2H), 2.91-2.85 (m, 1H), 1.42 (d, J=6.6, 6H), 1.00-0.90 (m, 4H).

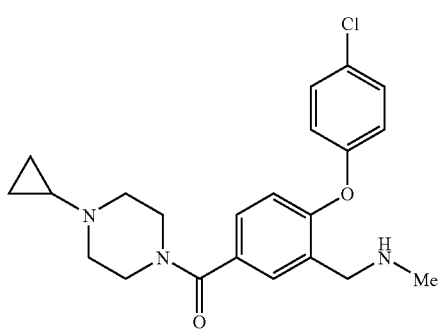

Example 18

[4-(4-Chloro-phenoxy)-3-methylaminomethyl-phenyl]-(4-cyclopropyl-piperazin-1-yl)-methanone MS (ESI): mass calcd. for $C_{22}H_{26}ClN_3O_2$, 399.17; m/z found, 400.3 [M+H]$^+$. $^1$H NMR (CDCl$_3$): 7.48 (d, J=2.1, 1H), 7.32-7.26 (m, 3H), 6.94-6.90 (m, 2H), 6.85 (d, J=8.3, 1H), 3.80 (s, 2H), 3.78-3.66 (m, 2H), 3.53-3.37 (m, 2H), 2.76-2.51 (m, 4H), 2.45 (s, 3H), 1.78-1.69 (m, 1H), 1.68-1.62 (m, 1H), 0.52-0.40 (m, 4H).

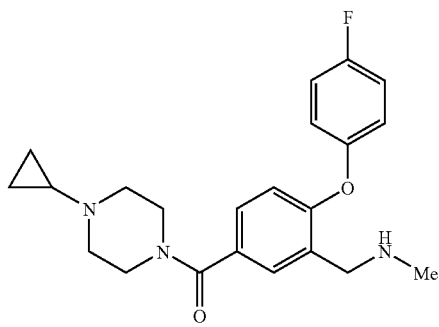

Example 19

(4-Cyclopropyl-piperazin-1-yl)-[4-(4-fluoro-phenoxy)-3-methylaminomethyl-phenyl]-methanone MS (ESI): mass calcd. for $C_{22}H_{26}FN_3O_2$, 383.20; m/z found, 384.4 [M+H]$^+$. $^1$H NMR (CDCl$_3$): 7.47 (d, J=2.0, 1H), 7.25 (dd, J=8.4, 2.1, 1H), 7.08-7.02 (m, 2H), 6.99-6.94 (m, 2H), 6.78 (d, J=8.4, 1H), 3.83 (s, 2H), 3.80-3.65 (m, 2H), 3.54-3.36 (m, 2H), 2.72-2.52 (m, 4H), 2.46 (s, 3H), 1.76-1.69 (m, 1H), 1.67-1.61 (m, 1H), 0.51-0.39 (m, 4H).

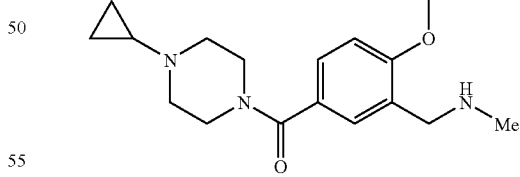

Example 20

(4-Cyclopropyl-piperazin-1-yl)-[3-methylaminomethyl-4-(6-methyl-pyridin-3-yloxy)-phenyl]-methanone MS (ESI): mass calcd. for $C_{22}H_{28}N_4O_2$, 380.22; m/z found, 381.4 [M+H]$^+$. $^1$H NMR (CDCl$_3$): 8.29 (d, J=2.8, 1H), 7.51 (d, J=2.1, 1H), 7.27 (dd, J=8.3, 2.2, 1H), 7.21 (dd, J=8.5, 2.8, 1H), 7.15 (d, J=8.4, 1H), 6.80 (d, J=8.3, 1H), 3.87 (s, 2H), 3.80-3.63 (m, 2H), 3.52-3.33 (m, 2H), 2.73-2.57 (m, 3H), 2.56 (s, 3H), 2.48 (s, 3H), 2.31-2.20 (m, 1H), 1.68-1.62 (m, 1H), 0.51-0.40 (m, 4H).

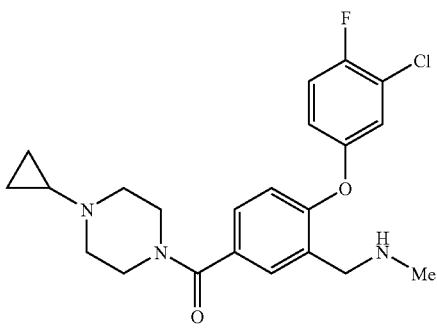

Example 21

[4-(3-Chloro-4-fluoro-phenoxy)-3-methylaminomethyl-phenyl]-(4-cyclopropyl-piperazin-1-yl)-methanone MS (ESI): mass calcd. for $C_{22}H_{25}ClFN_3O_2$, 417.16; m/z found, 418.3 [M+H]$^+$. $^1$H NMR (CDCl$_3$): 7.51 (d, J=2.1, 1H), 7.29 (dd, J=8.3, 2.2, 1H), 7.12 (t, J=8.6, 1H), 7.07-7.05 (m, 1H), 6.91-6.86 (m, 1H), 6.83 (d, J=8.3, 1H), 3.85 (s, 2H), 3.83-3.66 (m, 2H), 3.54-3.35 (m, 2H), 2.75-2.56 (m, 4H), 2.48 (s, 3H), 2.06-1.90 (m, 1H), 1.69-1.62 (m, 1H), 0.52-0.40 (m, 4H).

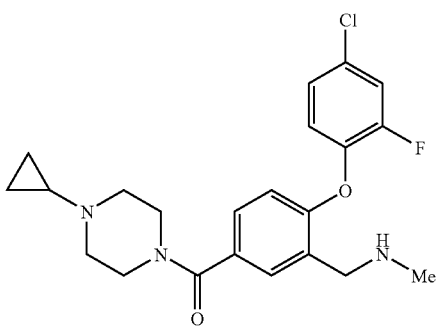

Example 22

[4-(4-Chloro-2-fluoro-phenoxy)-3-methylaminomethyl-phenyl]-(4-cyclopropyl-piperazin-1-yl)-methanone MS (ESI): mass calcd. for $C_{22}H_{25}ClFN_3O_2$, 417.16; m/z found, 418.3 [M+H]$^+$. $^1$H NMR (CDCl$_3$): 7.49 (d, J=2.0, 1H), 7.28-7.21 (m, 2H), 7.15-7.10 (m, 1H), 7.02 (t, J=8.6, 1H), 6.72 (d, J=8.3, 1H), 3.91 (s, 2H), 3.80-3.63 (m, 2H), 3.54-3.34 (m, 2H), 2.74-2.52 (m, 4H), 2.48 (s, 3H), 2.14-1.96 (m, 1H), 1.67-1.61 (m, 1H), 0.51-0.40 (m, 4H).

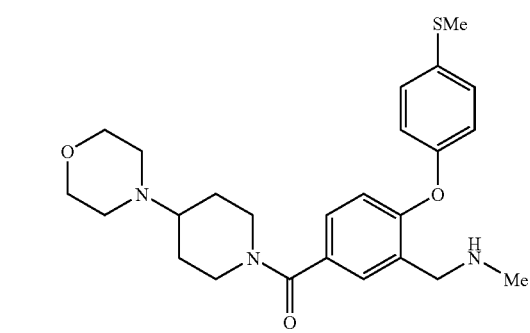

Example 23

[3-Methylaminomethyl-4-(4-methylsulfanyl-phenoxy)-phenyl]-(4-morpholin-4-yl-piperidin-1-yl)-methanone MS (ESI): mass calcd. for $C_{25}H_{33}N_3O_3S$, 455.22; m/z found, 456.4 [M+H]$^+$. $^1$H NMR (CDCl$_3$): 7.41 (d, J=1.9, 1H), 7.22-7.16 (m, 3H), 6.87 (d, J=8.7, 2H), 6.75 (d, J=8.4, 1H), 4.73-4.46 (m, 1H), 3.79 (s, 2H), 3.67-3.60 (m, 4H), 3.12-2.66 (m, 4H), 2.50-2.44 (m, 4H), 2.42-2.33 (m, 7H), 1.98-1.65 (m, 2H), 1.52-1.26 (m, 2H).

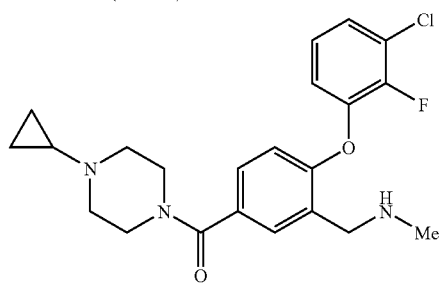

Example 24

[4-(3-Chloro-2-fluoro-phenoxy)-3-methylaminomethyl-phenyl]-(4-cyclopropyl-piperazin-1-yl)-methanone MS (ESI): mass calcd. for $C_{22}H_{25}ClFN_3O_2$, 417.16; m/z found, 418.3 [M+H]$^+$. $^1$H NMR (CDCl$_3$): 7.49 (d, J=2.1, 1H), 7.26 (dd, J=8.3, 2,2, 1H), 7.24-7.19 (m, 1H), 7.06 (td, J=8.2, 1.8, 1H), 6.96-6.91 (m, 1H), 6.76 (d, J=8.3, 1H), 3.88 (s, 2H), 3.82-3.65 (m, 2H), 3.53-3.33 (m, 2H), 2.73-2.50 (m, 4H), 2.47 (s, 3H), 1.72 (br s, 1H), 1.68-1.61 (m, 1H), 0.51-0.40 (m, 4H).

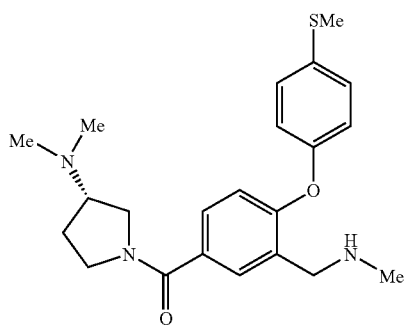

Example 25

(S)-(3-Dimethylamino-pyrrolidin-1-yl)-[3-methylaminomethyl-4-(4-methylsulfanyl-phenoxy)-phenyl]-methanone MS (ESI): mass calcd. for $C_{22}H_{29}N_3O_2S$, 399.20; m/z found, 400.3 [M+H]$^+$. $^1$H NMR (CDCl$_3$): 7.60 (s, 1H), 7.37 (dd, J=8.4, 2.1, 1H), 7.27 (d, J=7.2, 2H), 6.94 (t, J=7.7, 2H), 6.82 (d, J=8.4, 1H), 3.94-3.77 (m, 3H), 3.67-3.48 (m, 2H), 3.44-3.31 (m, 1H), 2.79-2.63 (m, 1H), 2.48 (s, 3H), 2.44 (s, 3H), 2.32-2.25 (m, 4H), 2.24-2.04 (m, 4H), 1.89-1.76 (m, 1H).

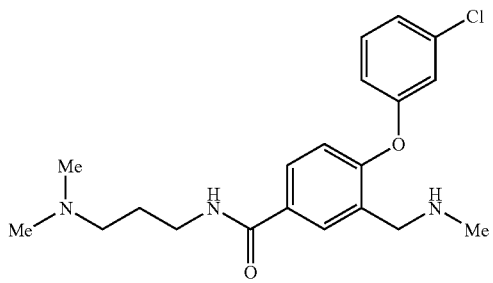

Example 26

4-(3-Chloro-phenoxy)-N-(2-dimethylamino-ethyl)-3-methylaminomethyl-benzamide

MS (ESI): mass calcd. for $C_{19}H_{24}ClN_3O_2$, 361.16; m/z found, 362.7 [M+H]$^+$. $^1$H NMR (CDCl$_3$): 7.89 (d, J=2.2, 1H), 7.71 (dd, J=8.5, 2.3, 1H), 7.28-7.24 (m, 1H), 7.12-7.09 (m, 1H), 6.97 (t, J=2.2, 1H), 6.91-6.85 (m, 2H), 3.82 (s, 2H), 3.56-3.51 (m, 2H), 2.56 (t, J=5.9, 2H), 2.46 (s, 3H), 2.30 (s, 6H).

Example 27

4-(3-Chloro-phenoxy)-N-(3-dimethylamino-propyl)-3-methylaminomethyl-benzamide

MS (ESI): mass calcd. for $C_{20}H_{26}ClN_3O_2$, 375.17; m/z found, 376.7 [M+H]$^+$. $^1$H NMR (CDCl$_3$): 8.50-8.44 (m, 1H), 7.86 (d, J=2.2, 1H), 7.67 (dd, J=8.5, 2.3, 1H), 7.28-7.24 (m, 1H), 7.12-7.08 (m, 1H), 6.97 (d, J=2.2, 1H), 6.90-6.84 (m, 2H), 3.81 (s, 2H), 3.59-3.54 (m, 2H), 2.52 (t, J=5.8, 2H), 2.43 (s, 3H), 2.31 (s, 6H), 1.80-1.74 (m, 2H).

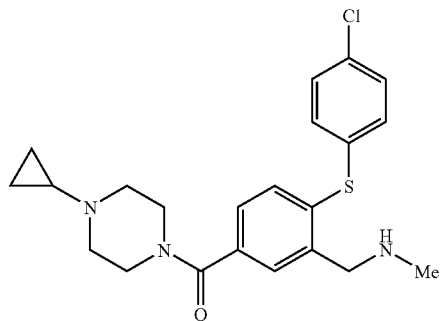

Example 28

[4-(4-Chloro-phenylsulfanyl)-3-methylaminomethyl-phenyl]-(4-cyclopropyl-piperazin-1-yl)-methanone The title compound was prepared in an similar manner as Example 1, using [5-bromo-2-(4-chloro-phenylsulfanyl)-benzyl]-methyl-carbamic acid tert-butyl ester. MS (ESI): mass calcd. for $C_{22}H_{26}ClN_3OS$, 415.15; m/z found, 416.3 [M+H]$^+$. $^1$H NMR (CDCl$_3$): 7.47-7.45 (m, 1H), 7.32-7.28 (m, 2H), 7.26-7.22 (m, 2H), 7.21-7.16 (m, 2H), 3.87 (s, 2H), 3.79-3.67 (m, 2H), 3.45-3.33 (m, 2H), 2.73-2.62 (m, 2H), 2.59-2.50 (m, 2H), 2.46 (s, 3H), 1.67-1.60 (m, 2H), 0.56-0.40 (m, 4H).

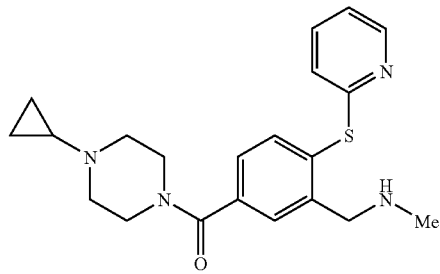

Example 29

(4-Cyclopropyl-piperazin-1-yl)-[3-methylaminomethyl-4-(pyridin-2-ylsulfanyl)-phenyl]-methanone The title compound was prepared by a sequence similar to that described in Example 28. MS (ESI): mass calculated for $C_{21}H_{26}N_4OS$, 382.18; m/z found, 383.7 [M+H]$^+$. $^1$H NMR (CDCl$_3$): 8.44-8.41 (m, 1H), 7.61 (d, J=7.9, 1H), 7.59-7.58 (m, 1H), 7.49 (td, J=7.6, 1.9, 1H), 7.32 (dd, J=7.9, 1.9, 1H), 7.06-7.02 (m, 1H), 6.91-6.88 (m, 1H), 3.90 (s, 2H), 3.80-3.70 (m, 2H), 3.46-3.35 (m, 2H), 2.75-2.63 (m, 2H), 2.61-2.53 (m, 2H), 2.41 (s, 3H), 1.68-1.62 (m, 1H), 0.50-0.40 (m, 4H).

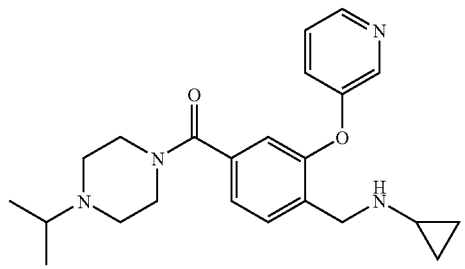

Example 30

[4-Cyclopropylaminomethyl-3-(pyridin-3-yloxy)-phenyl]-(4-isopropyl-piperazin-1-yl)-methanone Step A: 4-Bromo-2-(pyridin-3-yloxy)-benzaldehyde. The title compound was prepared in a similar manner as in Example 1, Step A (2.85 g, 71%). MS (ESI): mass calcd. for $C_{12}H_8BrNO_2$, 276.97; m/z found, 278.0, 280.0 [M+H]$^+$. $^1$H NMR (CDCl$_3$): 10.47 (s, 1H), 8.53 (dd, J=4.5, 1.3, 1H), 8.51 (d, J=2.7, 1H), 7.83 (d, J=8.4, 1H), 7.45-7.42 (m, 1H), 7.42-7.38 (m, 2H), 7.02-7.01 (m, 1H).

Step B: [4-Bromo-2-(pyridin-3-yloxy)-benzyl]-cyclopropyl-amine. To a mixture of 4-bromo-2-(pyridin-3-yloxy)-benzaldehyde (2.0 g, 7.19 mmol) in DCE (75 mL) were added cyclopropylamine (0.50 mL, 7.2 mmol), acetic acid (2.16 mL, 36.0 mmol), and NaBH(OAc)$_3$ (95%; 3.62 g, 18.0 mmol) portionwise. After 18 h, the mixture was diluted with 50 mL DCM and washed with 1 M NaOH (2×25 mL). The organic layer was dried (Na$_2$SO$_4$) and concentrated. FCC purification (EtOAc/DCM) gave the desired product (1.74 g, 76%). MS (ESI): mass calcd. for $C_{15}H_{15}BrN_2O$, 318.04; m/z found, 319.1, 321.1 [M+H]$^+$. $^1$H NMR (CDCl$_3$): 8.42-8.39 (m, 2H), 7.31-7.26 (m, 4H), 7.00-6.99 (m, 1H), 3.84 (s, 2H), 2.11-2.07 (m, 1H), 0.43-0.40 (m, 2H), 0.36-0.33 (m, 2H).

Step C: [4-Bromo-2-(pyridin-3-yloxy)-benzyl]-cyclopropyl-carbamic acid tert-butyl ester. The title compound was prepared in a similar manner as in Example 1, Step C. The crude material was carried forward without purification. MS (ESI): mass calcd. for $C_{20}H_{23}BrN_2O_3$, 418.09; m/z found, 419.1, 421.1 [M+H]$^+$.

Step D: Cyclopropyl-[4-(4-isopropyl-piperazine-1-carbonyl)-2-(pyridin-3-yloxy)-benzyl]-carbamic acid tert-butyl ester. The title compound was prepared in a similar manner as in Example 1, Step D. FCC purification (EtOAc/MeOH/DCM) gave the desired product. MS (ESI): mass calcd. for $C_{28}H_{38}N_4O_4$, 494.29; m/z found, 495.3 [M+H]$^+$. $^1$H NMR (CDCl$_3$): 8.41-8.40 (m, 1H), 8.40-8.38 (m, 1H), 7.31-7.23 (m, 3H), 7.20-7.17 (m, 1H), 6.91-6.89 (m, 1H), 4.53 (s, 2H), 3.76-3.70 (m, 2H), 3.43-3.36 (m, 2H), 2.75-2.68 (m, 1H), 2.59-2.48 (m, 3H), 2.45-2.38 (m, 2H), 1.44 (s, 9H), 1.03 (d, J=6.5, 6H), 0.72-0.60 (m, 4H).

Step E. The title compound was prepared in a similar manner as in Example 1, Step E (66.4 mg, 51%). MS (ESI): mass calcd. for $C_{23}H_{30}N_4O_2$, 394.24; m/z found, 395.3 [M+H]$^+$. $^1$H NMR (CDCl$_3$): 8.42-8.40 (m, 1H), 8.39 (t, J=3.1, 1H), 7.46 (d, J=7.7, 1H), 7.29-7.27 (m, 2H), 7.18 (dd, J=7.7, 1.5, 1H), 6.91 (d, J=1.4, 1H), 3.90 (s, 2H), 3.73 (br s, 2H), 3.39 (br s, 2H), 2.74-2.68 (m, 1H), 2.59-2.55 (m, 2H), 2.45-2.37 (m, 2H), 2.14-2.10 (m, 1H), 1.03 (d, J=6.5, 6H), 0.44-0.40 (m, 2H), 0.38-0.34 (m, 2H).

The compounds in Examples 31-32 were prepared by a sequence similar to that described in Example 30.

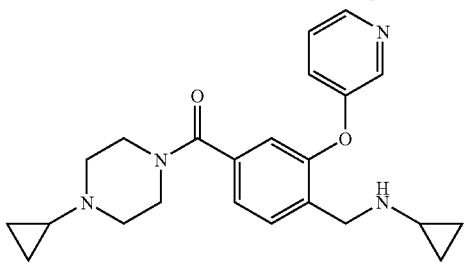

Example 31

[4-Cyclopropylaminomethyl-3-(pyridin-3-yloxy)-phenyl]-(4-cyclopropyl-piperazin-1-yl)-methanone MS (ESI): mass calcd. for $C_{23}H_{28}N_4O_2$, 392.22; m/z found, 393.2 [M+H]$^+$. $^1$H NMR (CDCl$_3$): 8.42-8.41 (m, 1H), 8.40-8.38 (m, 1H), 7.47 (d, J=7.7, 1H), 7.29-7.27 (m, 2H), 7.19-7.17 (m, 1H), 6.92-6.91 (m, 1H), 3.91 (s, 2H), 3.69 (br s, 2H), 3.34 (br s, 2H), 2.65 (br s, 2H), 2.50 (br s, 2H), 2.15-2.11 (m, 1H), 1.64-1.59 (m, 1H), 0.49-0.36 (m, 8H).

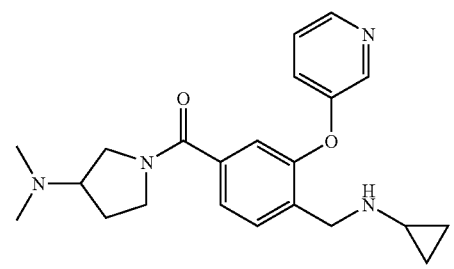

Example 32

[4-Cyclopropylaminomethyl-3-(pyridin-3-yloxy)-phenyl]-(3-dimethylamino-pyrrolidin-1-yl)-methanone MS (ESI): mass calcd. for $C_{22}H_{28}N_4O_2$, 380.22; m/z found, 381.2 [M+H]$^+$. $^1$H NMR (CDCl$_3$, mixture of rotamers): 8.41-8.37 (m, 2H), 7.46 (dd, J=7.8, 2.4, 1H), 7.31-7.27 (m, 3H), 7.03-7.01 (m, 1H), 3.92-3.74 (m, 3H), 3.60-3.20 (m, 3H), 2.74-2.60 (m, 1H), 2.28 (s, 3H), 2.20 (s, 3H), 2.18-1.90 (m, 3H), 1.84-1.75 (m, 1H), 0.45-0.34 (m, 4H).

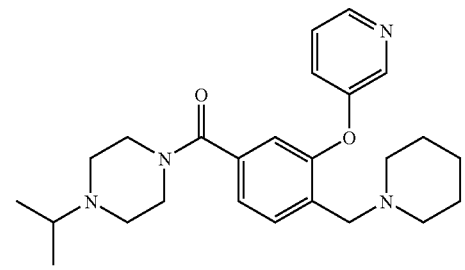

Example 33

(4-Isopropyl-piperazin-1-yl)-[4-piperidin-1-ylmethyl-3-(pyridin-3-yloxy)-phenyl]-methanone Step A: 3-(5-Bromo-2-piperidin-1-ylmethyl-phenoxy)-pyridine. The title compound was prepared in a similar manner as in Example 30, Step B (0.91 g, 85%). MS (ESI): mass calcd. for $C_{17}H_{19}BrN_2O$, 346.07; m/z found, 347.1, 349.1 [M+H]$^+$. $^1$H NMR (CDCl$_3$): 8.39-8.36 (m, 2H), 7.42 (d, J=8.2, 1H), 7.32 (dd, J=8.2, 1.9, 1H), 7.30-7.26 (m, 1H), 7.23-7.20 (m, 1H), 7.06 (d, J=1.9, 1H), 3.46 (s, 2H), 2.38 (br s, 4H), 1.55-1.48 (m, 4H), 1.44-1.37 (m, 2H).

Step B. The title compound was prepared in a similar manner as in Example 1, Step D. MS (ESI): mass calcd. for $C_{25}H_{34}N_4O_2$, 422.27; m/z found, 423.3 [M+H]$^+$. $^1$H NMR (CDCl$_3$): 8.36-8.32 (m, 2H), 7.56 (d, J=7.8, 1H), 7.25-7.17 (m, 3H), 6.94-6.92 (m, 1H), 3.73 (br s, 2H), 3.49 (s, 2H), 3.40 (br s, 2H), 2.73-2.66 (m, 1H), 2.61-2.34 (m, 8H), 1.52-1.46 (m, 4H), 1.42-1.35 (m, 2H), 1.02 (d, J=6.5, 6H).

The compounds in Examples 34-35 were prepared by a sequence similar to that described in Example 33.

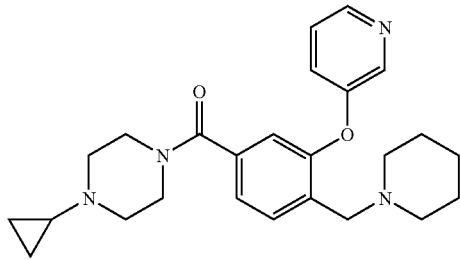

Example 34

(4-Cyclopropyl-piperazin-1-yl)-[4-piperidin-1-ylmethyl-3-(pyridin-3-yloxy)-phenyl]-methanone MS (ESI): mass calcd. for $C_{25}H_{32}N_4O_2$, 420.25; m/z found, 421.3 [M+H]$^+$. $^1$H NMR (CDCl$_3$): 8.36 (d, J=2.8, 1H), 8.34 (dd, J=4.6, 1.3, 1H), 7.57 (d, J=7.8, 1H), 7.26-7.18 (m, 3H), 6.94 (d, J=1.4, 1H), 3.70 (br s, 2H), 3.50 (s, 2H), 3.36 (br s, 2H), 2.66 (br s, 2H), 2.52 (br s, 2H), 2.42-2.33 (m, 4H), 1.65-1.60 (m, 1H), 1.53-1.48 (m, 4H), 1.43-1.36 (m, 2H), 0.49-0.40 (m, 4H).

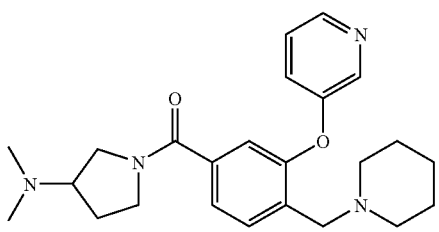

Example 35

(3-Dimethylamino-pyrrolidin-1-yl)-[4-piperidin-1-ylmethyl-3-(pyridin-3-yloxy)-phenyl]-methanone MS (ESI): mass calcd. for $C_{24}H_{32}N_4O_2$, 408.25; m/z found, 409.3 [M+H]$^+$. $^1$H NMR (CDCl$_3$, mixture of rotamers): 8.35-8.32 (m, 2H), 7.57-7.54 (m, 1H), 7.33-7.30 (m, 1H), 7.24-7.16 (m, 2H), 7.04 (dd, J=5.6, 1.2, 1H), 3.90-3.74 (m, 1H), 3.59-3.51 (m, 1.5H), 3.50 (s, 1H), 3.48 (s, 1H), 3.46-3.34 (m, 1H), 3.24 (t, J=9.5, 0.5H), 2.73-2.60 (m, 1H), 2.45-2.30 (m, 4H), 2.27 (s, 3H), 2.19 (s, 3H), 2.08-2.01 (m, 1H), 1.83-1.75 (m, 1H), 1.52-1.45 (m, 4H), 1.41-1.34 (m, 2H).

The compounds in Examples 36-39 were prepared by a sequence similar to that described in Example 30.

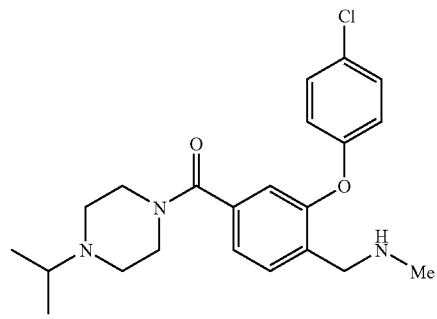

Example 36

[3-(4-Chloro-phenoxy)-4-methylaminomethyl-phenyl]-(4-isopropyl-piperazin-1-yl)-methanone MS (ESI): mass calcd. for $C_{22}H_{28}ClN_3O_2$, 401.19; m/z found, 402.8 [M+H]$^+$. $^1$H NMR (CDCl$_3$): 7.44 (d, J=7.7, 1H), 7.29 (d, J=8.9, 2H), 7.15 (dd, J=7.7, 1.5, 1H), 6.91 (d, J=8.9, 2H), 6.87 (d, J=1.4, 1H), 3.79 (s, 2H), 3.76-3.67 (m, 2H), 3.42-3.32 (m, 2H), 2.73-2.67 (m, 1H), 2.58-2.50 (m, 2H), 2.44 (s, 3H), 2.42-2.34 (m, 2H), 1.02 (d, J=6.5, 6H).

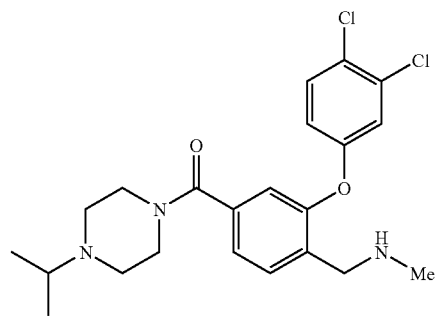

Example 37

[3-(3,4-Dichloro-phenoxy)-4-methylaminomethyl-phenyl]-(4-isopropyl-piperazin-1-yl)-methanone MS (ESI): mass calcd. for $C_{22}H_{27}Cl_2N_3O_2$, 435.15; m/z found, 436.7 [M+H]$^+$. $^1$H NMR (CDCl$_3$): 7.46 (d, J=7.8, 1H), 7.37 (d, J=8.8, 1H), 7.19 (dd, J=7.7, 1.5, 1H), 7.05 (d, J=2.8, 1H), 6.90 (d, J=1.5, 1H), 6.81 (dd, J=8.8, 2.8, 1H), 3.77-3.66 (m, 4H), 3.44-3.33 (m, 2H), 2.74-2.66 (m, 1H), 2.58-2.50 (m, 2H), 2.45-2.35 (m, 5H), 1.02 (d, J=6.6, 6H).

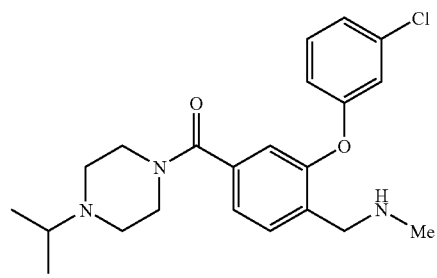

Example 38

[3-(3-Chloro-phenoxy)-4-methylaminomethyl-phenyl]-(4-isopropyl-piperazin-1-yl)-methanone MS (ESI): mass calcd. for C$_{22}$H$_{28}$ClN$_3$O$_2$, 401.19; m/z found, 402.8 [M+H]$^+$. $^1$H NMR (CDCl$_3$): 7.47 (d, J=7.7, 1H), 7.27 (t, J=8.1, 1H), 7.19 (dd, J=7.7, 1.5, 1H), 7.11-7.07 (m, 1H), 6.97 (t, J=2.2, 1H), 6.91 (d, J=1.5, 1H), 6.86 (ddd, J=8.3, 2.3, 0.82, 1H), 3.81 (s, 2H), 3.77-3.67 (m, 2H), 3.45-3.33 (m, 2H), 2.76-2.67 (m, 1H), 2.60-2.50 (m, 2H), 2.47-2.36 (m, 5H), 1.03 (d, J=6.5, 6H).

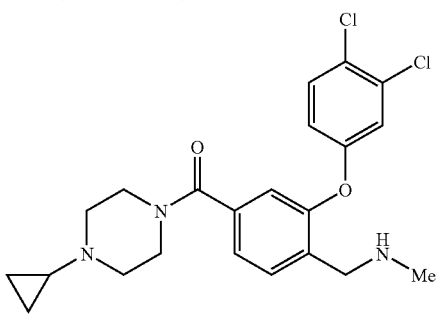

Example 39

(4-Cyclopropyl-piperazin-1-yl)-[3-(3,4-dichloro-phenoxy)-4-methylaminomethyl-phenyl]-methanone MS (ESI): mass calcd. for C$_{22}$H$_{25}$Cl$_2$N$_3$O$_2$, 433.13; m/z found, 434.7 [M+H]$^+$. $^1$H NMR (CDCl$_3$): 7.48 (d, J=7.7, 1H), 7.39 (d, J=8.8, 1H), 7.20 (dd, J=7.7, 1.5, 1H), 7.08 (d, J=2.8, 1H), 6.92 (d, J=1.5, 1H), 6.83 (dd, J=8.8, 2.8, 1H), 3.80 (s, 2H), 3.76=3.63 (m, 2H), 3.42-3.27 (m, 2H), 2.71-2.60 (m, 2H), 2.58-2.47 (m, 2H), 2.46 (s, 3H), 1.66-1.59 (m, 1H), 0.51-0.38 (m, 4H).

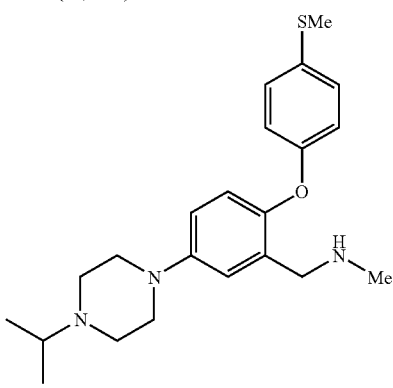

Example 40

[5-(4-Isopropyl-piperazin-1-yl)-2-(4-methylsulfanyl-phenoxy)-benzyl]-methyl-amine Step A: [5-(4-Isopropyl-piperazin-1-yl)-2-(4-methylsulfanyl-phenoxy)-benzyl]-methyl-carbamic acid tert-butyl ester. A mixture of [5-bromo-2-(4-methylsulfanyl-phenoxy)-benzyl]-methyl-carbamic acid tert-butyl ester (300 mg, 0.684 mmol) {prepared in an analogous fashion to Example 1, Steps A-C}, isopropyl piperazine (132 mg, 1.02 mmol), XPHOS (39 mg, 0.082 mmol), Pd$_2$(dba)$_3$ (62.6 mg, 0.0684 mmol), and t-BuONa (98.0 mg, 1.02 mmol) in toluene was heated in a sealed tube overnight at 120° C. After cooling to rt, the mixture was filtered through diatomaceous earth and the filtrate was concentrated. Purification by FCC gave the desired product (180 mg, 54%). MS (ESI): mass calcd. for C$_{27}$H$_{39}$N$_3$O$_3$S, 485.27; m/z found, 486.4 [M+H]$^+$. $^1$H NMR (CDCl$_3$): 7.22 (d, J=8.5, 2H), 6.86-6.83 (m, 1H), 6.83-6.80 (m, 4H), 4.42-4.35 (m, 2H), 3.19-3.16 (m, 4H), 2.87-2.83 (m, 2H), 2.80-2.75 (m, 1H), 2.75-2.71 (m, 1H), 2.71-2.67 (m, 4H), 2.44 (s, 3H), 1.48-1.40 (m, 9H), 1.10 (d, J=6.5, 6H).

Step B. The title compound was prepared in an analogous fashion to Example 1, Step E. MS (ESI): mass calcd. for C$_{22}$H$_{31}$N$_3$OS, 385.22; m/z found, 386.4 [M+H]$^+$. $^1$H NMR (CDCl$_3$): 7.22 (d, J=8.9, 2H), 6.99 (d, J=2.7, 1H), 6.86-6.80 (m, 4H), 3.69 (s, 2H), 3.22-3.17 (m, 4H), 2.72-2.67 (m, 4H), 2.45 (s, 3H), 2.40 (s, 3H), 2.08-1.97 (br s, 1H), 1.10 (d, J=6.5, 6H).

The compounds in Examples 41-58 were prepared by a sequence similar to that described in Example 40.

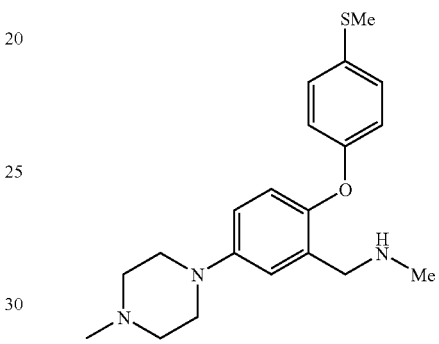

Example 41

Methyl-[5-(4-methyl-piperazin-1-yl)-2-(4-methylsulfanyl-phenoxy)-benzyl]-amine

MS (ESI): mass calcd. for C$_{20}$H$_{27}$N$_3$OS, 357.19; m/z found, 358.3 [M+H]$^+$. $^1$H NMR (CDCl$_3$): 7.22 (d, J=8.9, 2H), 7.01 (d, J=2.5, 1H), 6.85-6.81 (m, 4H), 3.78 (s, 2H), 3.20-3.16 (m, 4H), 2.59-2.56 (m, 4H), 2.45 (s, 3H), 2.44 (s, 3H), 2.35 (s, 3H).

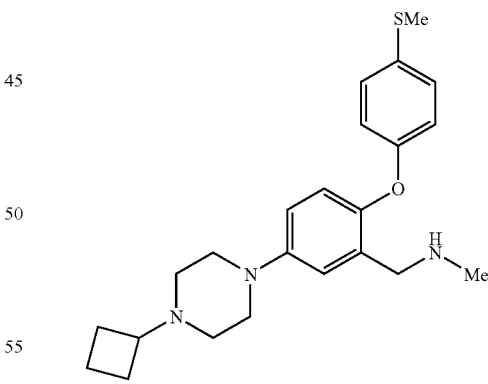

Example 42

[5-(4-Cyclobutyl-piperazin-1-yl)-2-(4-methylsulfanyl-phenoxy)-benzyl]-methyl-amine MS (ESI): mass calcd. for C$_{23}$H$_{31}$N$_3$OS, 397.22; m/z found, 398.4 [M+H]$^+$. $^1$H NMR (CDCl$_3$): 7.21 (d, J=8.8, 2H), 6.97 (d, J=2.8, 1H), 6.84-6.76 (m, 4H), 3.68 (s, 2H), 3.20-3.16 (m, 4H), 2.82-2.74 (m, 1H), 2.50-2.46 (m, 4H), 2.43 (s, 3H), 2.39 (s, 3H), 2.09-2.02 (m, 2H), 1.96-1.86 (m, 2H), 1.78-1.66 (m, 2H).

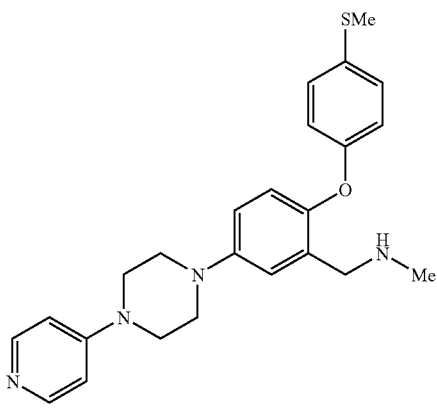

Example 43

Methyl-[2-(4-methylsulfanyl-phenoxy)-5-(4-pyridin-4-yl-piperazin-1-yl)-benzyl]-amine MS (ESI): mass calcd. for $C_{24}H_{28}N_4OS$, 420.20; m/z found, 421.3 [M+H]$^+$. $^1$H NMR (CDCl$_3$): 8.42-8.21 (m, 2H), 7.24 (d, J=8.8, 2H), 7.09-7.05 (m, 1H), 6.92-6.82 (m, 4H), 6.78-6.66 (m, 2H), 3.80-3.67 (m, 2H), 3.54-3.48 (m, 4H), 3.34-3.28 (m, 4H), 2.50-2.38 (m, 5H), 2.28-2.14 (m, 2H).

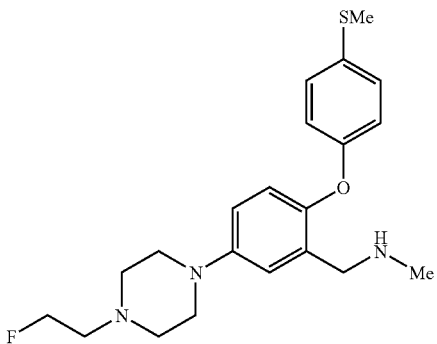

Example 44

[5-[4-(2-Fluoro-ethyl)-piperazin-1-yl]-2-(4-methyl-sulfanyl-phenoxy)-benzyl]-methyl-amine MS (ESI): mass calcd. for $C_{21}H_{28}FN_3OS$, 389.19; m/z found, 390.3 [M+H]$^+$. $^1$H NMR (CDCl$_3$): 7.22 (d, J=8.9, 2H), 6.99 (d, J=2.8, 1H), 6.86-6.78 (m, 4H), 4.67 (t, J=4.7, 1H), 4.57 (t, J=4.7, 1H), 3.68 (s, 2H), 3.24-3.18 (m, 4H), 2.80 (t, J=4.8, 1H), 2.75-2.69 (m, 5H), 2.45 (s, 3H), 2.40 (s, 3H), 2.01 (br s, 1H).

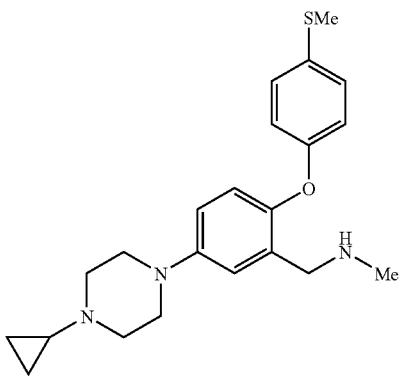

Example 45

[5-(4-Cyclopropyl-piperazin-1-yl)-2-(4-methylsulfa-nyl-phenoxy)-benzyl]-methyl-amine MS (ESI): mass calcd. for $C_{22}H_{29}N_3OS$, 383.20; m/z found, 384.3 [M+H]$^+$. $^1$H NMR (CDCl$_3$): 7.21 (d, J=8.8, 2H), 7.02 (d, J=2.5, 1H), 6.85 (d, J=8.8, 2H), 6.80-6.78 (m, 2H), 3.93 (s, 2H), 3.11-3.08 (m, 4H), 2.75-2.72 (m, 4H), 2.49 (s, 3H), 2.44 (s, 3H), 1.67-1.62 (m, 1H), 0.50-0.41 (m, 4H).

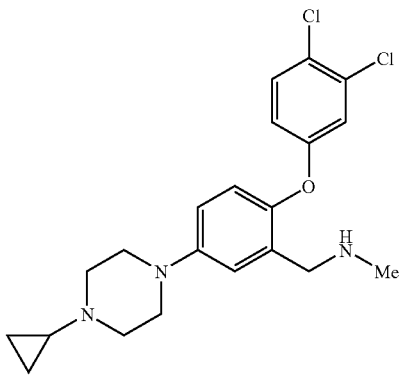

Example 46

[5-(4-Cyclopropyl-piperazin-1-yl)-2-(3,4-dichloro-phenoxy)-benzyl]-methyl-amine

MS (ESI): mass calcd. for $C_{21}H_{25}Cl_2N_3O$, 405.14; m/z found, 406.7 [M+H]$^+$. $^1$H NMR (CDCl$_3$): 7.36 (d, J=8.8, 1H), 7.08 (d, J=2.7, 1H), 7.01 (d, J=2.8, 1H), 6.88-6.80 (m, 3H), 4.00 (s, 2H), 3.18-3.11 (m, 4H), 2.82-2.77 (m, 4H), 2.55 (s, 3H), 1.76-1.68 (m, 1H), 0.55-0.51 (m, 4H).

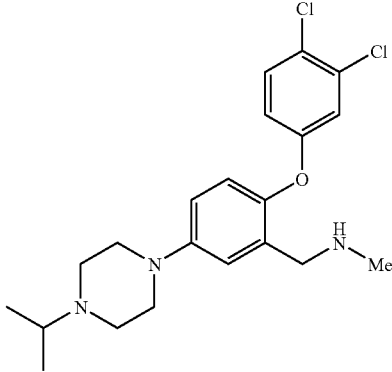

Example 47

[2-(3,4-Dichloro-phenoxy)-5-(4-isopropyl-piperazin-1-yl)-benzyl]-methyl-amine

MS (ESI): mass calcd. for $C_{21}H_{27}Cl_2N_3O$, 407.15; m/z found, 408.2 [M+H]$^+$. $^1$H NMR (CDCl$_3$): 7.32 (d, J=8.9, 1H), 7.01 (d, J=2.7, 1H), 6.96 (d, J=2.8, 1H), 6.87-6.80 (m, 2H), 6.75 (dd, J=8.9, 2.8, 1H), 3.68 (s, 2H), 3.24-3.20 (m, 4H), 2.80-2.73 (m, 1H), 2.73-2.70 (m, 4H), 2.42 (s, 3H), 1.11 (d, J=6.5, 6H).

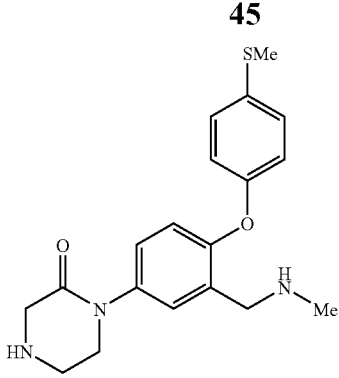

Example 48

1-[3-Methylaminomethyl-4-(4-methylsulfanyl-phenoxy)-phenyl]-piperazin-2-one

MS (ESI): mass calcd. for $C_{19}H_{23}N_3O_2S$, 357.15; m/z found, 358.4 [M+H]+. $^1$H NMR (CDCl$_3$): 7.42-7.38 (m, 1H), 7.28-7.24 (m, 2H), 7.134 (dd, J=8.6, 2.6, 1H), 6.96-6.92 (m, 2H), 6.85-6.82 (m, 1H), 3.91-3.79 (m, 2H), 3.72-3.64 (m, 4H), 3.24-3.18 (m, 2H), 2.47 (s, 6H).

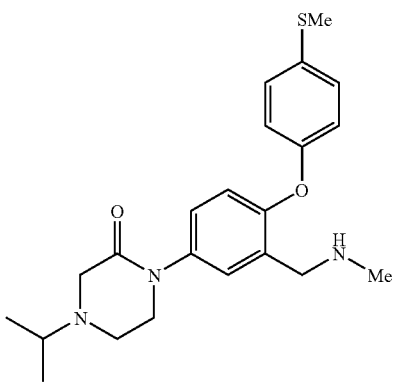

Example 49

4-Isopropyl-1-[3-methylaminomethyl-4-(4-methylsulfanyl-phenoxy)-phenyl]-piperazin-2-one MS (ESI): mass calcd. for $C_{22}H_{29}N_3O_2S$, 399.20; m/z found, 400.2 [M+H]+. $^1$H NMR (CDCl$_3$): 7.36 (d, J=2.6, 1H), 7.24 (d, J=8.8, 2H), 7.13 (dd, J=8.6, 2.6, 1H), 6.92 (d, J=8.8, 2H), 6.81 (d, J=8.7, 1H), 3.84 (s, 2H), 3.67-3.63 (m, 2H), 3.63-3.58 (m, 1H), 3.36 (s, 2H), 2.84-2.80 (m, 2H), 2.80-2.73 (m, 1H), 2.46 (s, 6H), 1.09 (d, J=6.5, 6H).

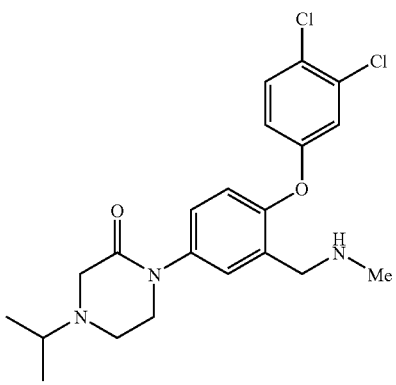

Example 50

1-[4-(3,4-Dichloro-phenoxy)-3-methylaminomethyl-phenyl]-4-isopropyl-piperazin-2-one MS (ESI): mass calcd. for $C_{21}H_{25}Cl_2N_3O_2$, 421.13; m/z found, 422.3 [M+H]+. $^1$H NMR (CDCl$_3$): 7.41 (d, J=2.6, 1H), 7.37 (d, J=8.8, 1H), 7.20 (dd, J=8.6, 2.6, 1H), 7.09 (d, J=2.8, 1H), 6.90 (d, J=8.6, 1H), 6.84 (dd, J=8.8, 2.8, 1H), 3.75 (s, 2H), 3.71-3.68 (m, 2H), 3.40 (s, 2H), 2.87-2.84 (m, 2H), 2.82-2.75 (m, 1H), 2.45 (s, 3H), 1.11 (d, J=6.5, 6H).

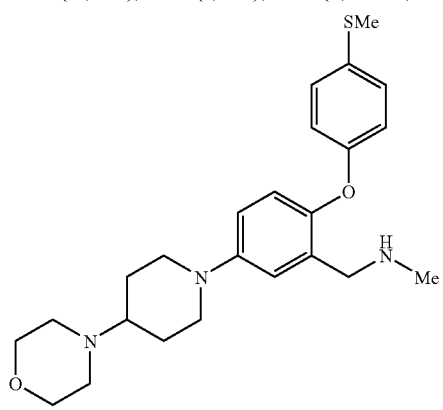

Example 51

Methyl-[2-(4-methylsulfanyl-phenoxy)-5-(4-morpholin-4-yl-piperidin-1-yl)-benzyl]-amine MS (ESI): mass calcd. for $C_{24}H_{33}N_3O_2S$, 427.23; m/z found, 428.4 [M+H]+. $^1$H NMR (CDCl$_3$): 7.23 (d, J=8.8, 2H), 7.02 (d, J=2.3, 1H), 6.84 (d, J=8.8, 2H), 6.83-6.81 (m, 2H), 3.80 (s, 2H), 3.76-3.72 (m, 4H), 3.70-3.65 (m, 2H), 2.70 (td, J=12.1, 2.1, 2H), 2.60-2.56 (m, 4H), 2.46 (s, 6H), 2.33-2.26 (m, 1H), 1.97-1.91 (m, 2H), 1.69-1.58 (m, 2H).

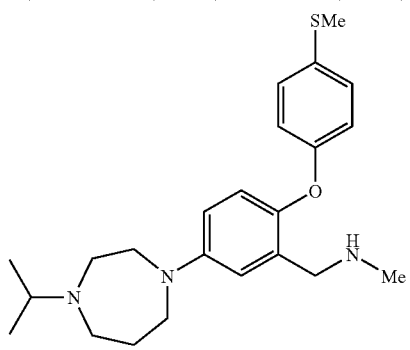

Example 52

[5-(4-Isopropyl-[1,4]diazepan-1-yl)-2-(4-methylsulfanyl-phenoxy)-benzyl]-methyl-amine MS (ESI): mass calcd. for $C_{23}H_{33}N_3OS$, 399.23; m/z found, 400.4 [M+H]+. $^1$H NMR (MeOD): 7.37 (s, 1H), 7.32 (d, J=8.6, 2H), 7.17-7.12 (m, 1H), 7.00 (d, J=8.7, 2H), 6.92 (d, J=9.0, 1H), 4.25 (s, 2H), 4.02-3.96 (m, 2H), 3.78-3.65 (m, 4H), 3.64-3.52 (m, 2H), 3.36-3.32 (m, 1H), 2.77 (s, 3H), 2.47 (s, 3H), 2.46-2.38 (m, 2H), 1.43 (d, J=6.5, 6H).

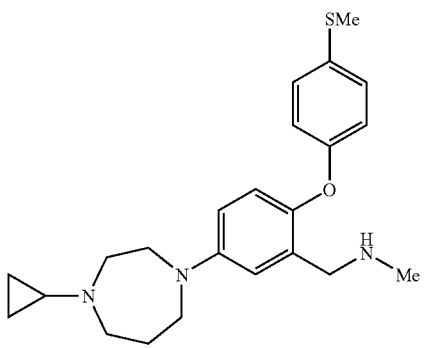

Example 53

[5-(4-Cyclopropyl-[1,4]diazepan-1-yl)-2-(4-methyl-sulfanyl-phenoxy)-benzyl]-methyl-amine MS (ESI): mass calcd. for $C_{23}H_{31}N_3O_s$, 397.22; m/z found, 398.3 [M+H]$^+$. $^1$H NMR (CDCl$_3$): 7.23 (d, J=8.8, 2H), 6.90 (d, J=2.9, 1H), 6.85 (d, J=8.8, 2H), 6.82 (d, J=9.0, 1H), 6.62 (dd, J=9.0, 3.0, 1H), 4.06 (s, 2H), 3.65-3.60 (m, 2H), 3.42 (t, J=6.2, 2H), 3.36-3.27 (m, 2H), 3.23-3.14 (m, 2H), 2.62 (s, 3H), 2.46 (s, 3H), 2.30-2.23 (m, 1H), 2.22-2.14 (m, 2H), 1.03-0.93 (m, 2H), 0.74-0.68 (m, 2H).

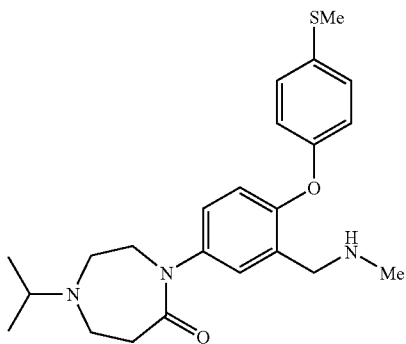

Example 54

1-Isopropyl-4-[3-methylaminomethyl-4-(4-methyl-sulfanyl-phenoxy)-phenyl]-[1,4]diazepan-5-one MS (ESI): mass calcd. for $C_{23}H_{31}N_3O_2S$, 413.21; m/z found, 414.4 [M+H]$^+$. $^1$H NMR (CDCl$_3$): 7.35-7.30 (m, 1H), 7.28-7.24 (m, 2H), 7.08-7.03 (m, 1H), 7.00-6.96 (m, 1H), 6.94-6.91 (m, 1H), 6.85 (t, J=8.2, 1H), 3.84-3.80 (m, 2H), 3.78 (d, J=4.0, 2H), 2.99-2.91 (m, 1H), 2.85-2.76 (m, 6H), 2.45 (s, 3H), 2.00-1.90 (m, 3H), 1.06 (d, J=6.6, 6H).

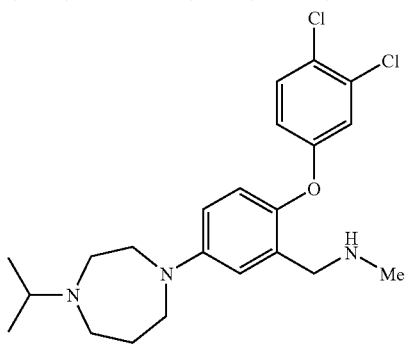

Example 55

[2-(3,4-Dichloro-phenoxy)-5-(4-isopropyl-[1,4]diaz-epan-1-yl)-benzyl]-methyl-amine MS (ESI): mass calcd. for $C_{22}H_{29}Cl_2N_3O$, 421.17; m/z found, 422.2 [M+H]$^+$. $^1$H NMR (CDCl$_3$): 7.30 (d, J=8.9, 1H), 6.95 (d, J=2.8, 1H), 6.82 (d, J=8.9, 1H), 6.74 (dd, J=8.9, 2.9, 1H), 6.73-6.71 (m, 1H), 6.58 (dd, J=8.9, 3.1, 1H), 3.62 (s, 2H), 3.58-3.54 (m, 2H), 3.52 (t, J=6.2, 2H), 3.03-2.95 (m, 1H), 2.83-2.80 (m, 2H), 2.66-2.62 (m, 2H), 2.41 (s, 3H), 2.00-1.94 (m, 2H), 1.04 (d, J=6.6, 6H).

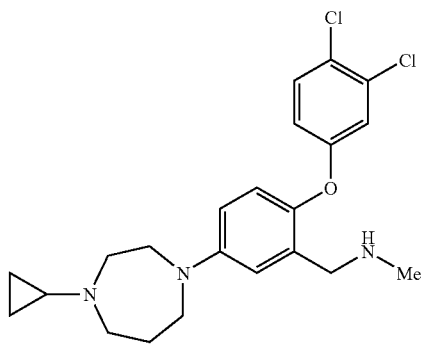

Example 56

[5-(4-Cyclopropyl-[1,4]diazepan-1-yl)-2-(3,4-dichloro-phenoxy)-benzyl]-methyl-amine MS (ESI): mass calcd. for $C_{22}H_{27}Cl_2N_3O$, 419.15; m/z found, 420.8 [M+H]$^+$. $^1$H NMR (CDCl$_3$): 7.30 (d, J=8.9, 1H), 6.95 (d, J=2.8, 1H), 6.83 (d, J=8.9, 1H), 6.74 (dd, J=8.9, 2.8, 1H), 6.72 (d, J=3.1, 1H), 6.78 (dd, J=8.9, 1H), 3.61 (s, 2H), 3.54-3.47 (m, 4H), 2.96-2.92 (m, 2H), 2.82-2.78 (m, 2H), 241 (s, 3H), 1.98-1.92 (m, 2H), 1.87-1.82 (m, 2H), 0.49-0.44 (m, 2H), 0.43-0.38 (m, 2H).

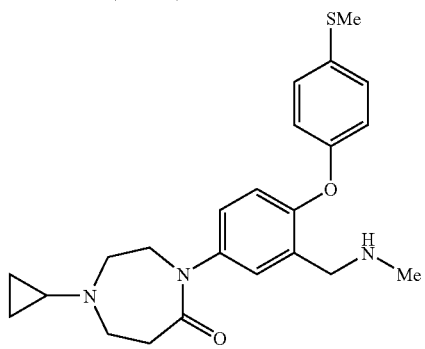

Example 57

1-Cyclopropyl-4-[3-methylaminomethyl-4-(4-methylsulfanyl-phenoxy)-phenyl]-[1,4]diazepan-5-one MS (ESI): mass calcd. for $C_{23}H_{29}N_3O_2S$, 411.20; m/z found, 412.8 [M+H]$^+$. $^1$H NMR (CDCl$_3$): 7.27-7.24 (m, 3H), 7.05 (dd, J=8.6, 2.6, 1H), 6.92 (d, J=8.8, 2H), 6.83 (d, J=8.6, 1H), 3.79-3.75 (m, 4H), 2.94-2.90 (m, 4H), 2.81-2.77 (m, 2H), 2.48 (s, 3H), 2.46 (s, 3H), 1.80-1.76 (m, 1H), 0.56-0.51 (m, 2H), 0.47-0.43 (m, 2H).

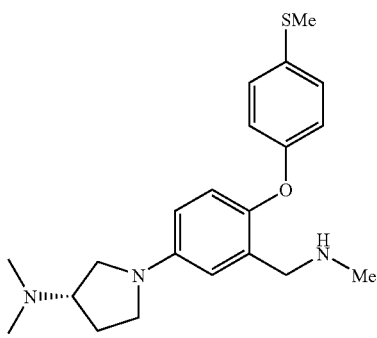

Example 58

(S)-Dimethyl-{1-[3-methylaminomethyl-4-(4-methylsulfanyl-phenoxy)-phenyl]-pyrrolidin-3-yl}-amine MS (ESI): mass calcd. for $C_{21}H_{29}N_3OS$, 371.20; m/z found, 372.7 [M+H]+. $^1$H NMR (CDCl$_3$): 7.21 (d, J=8.9, 2H), 6.86 (d, J=8.7, 1H), 6.81 (d, J=8.8, 2H), 6.57 (d, J=2.9, 1H), 6.43 (dd, J=8.8, 3.0, 1H), 3.66 (s, 2H), 3.53-3.48 (m, 1H), 3.45 (td, J=9.0, 2.1, 1H), 3.37-3.30 (m, 1H), 3.17 (t, J=8.4, 1H), 2.88-2.80 (m, 1H), 2.45 (s, 3H), 2.40 (s, 3H), 2.32 (s, 6H), 2.25-2.19 (m, 1H), 1.97-1.88 (m, 1H).

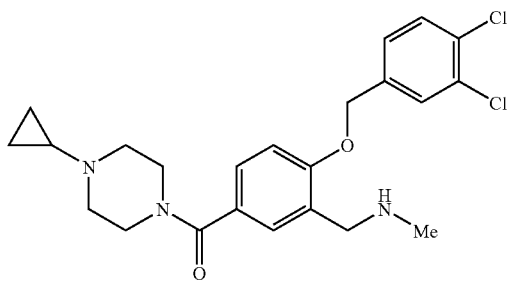

Example 59

(4-Cyclopropyl-piperazin-1-yl)-[4-(3,4-dichloro-benzyloxy)-3-methylaminomethyl-phenyl]-methanone Step A: [5-Bromo-2-(3,4-dichloro-benzyloxy)-benzyl]-methyl-carbamic acid tert-butyl ester. A mixture of (5-bromo-2-hydroxy-benzyl)-methyl-carbamic acid tert-butyl ester (1.0 g, 3.2 mmol), K$_2$CO$_3$ (655 mg, 4.74 mmol), and 4-bromomethyl-1,2-dichloro-benzene (1.14 g, 4.74 mmol) in CH$_3$CN (6.3 mL) was heated at 90° C. overnight. The mixture was then cooled to rt, diluted with EtOAc and water, and extracted with EtOAc (3×). The combined organic layers were washed with brine, dried (Na$_2$SO$_4$), and concentrated. Purification by FCC (EtOAc/hexanes) gave the desired product (1.49 g, 99%). $^1$H NMR (CDCl$_3$, mixture of rotamers): 7.49 (d, J=1.9, 1H), 7.46 (d, J=7.8, 1H), 7.31 (dd, J=8.7, 2.0, 1H), 7.28-7.22 (m, 2H), 6.73 (d, J=8.6, 1H), 5.00 (s, 2H), 4.52-4.38 (m, 2H), 2.90-2.80 (m, 3H), 1.52-1.39 (m, 9H).

Step B. The title compound was prepared in an analogous fashion to Example 1, Steps D-E. MS (ESI): mass calcd. for $C_{23}H_{27}Cl_2N_3O_2$, 447.15; m/z found, 448.3 [M+H]+. $^1$H NMR (CDCl$_3$): 7.51 (d, J=1.8, 1H), 7.45 (d, J=8.2, 1H), 7.36 (d, J=2.0, 1H), 7.29 (dd, J=8.3, 2.1, 1H), 7.24 (dd, J=8.3, 1.9, 1H), 6.85 (d, J=8.4, 1H), 5.06 (s, 2H), 3.81 (s, 2H), 3.75-3.32 (m, 4H), 2.72-2.48 (m, 4H), 2.44 (s, 3H), 2.21 (br s, 1H), 1.64-1.58 (m, 1H), 0.47-0.43 (m, 2H), 0.42-0.39 (m, 2H).

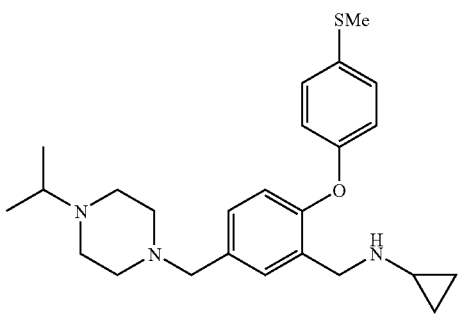

Example 60

Cyclopropyl-[5-(4-isopropyl-piperazin-1-ylmethyl)-2-(4-methylsulfanyl-phenoxy)-benzyl]-amine Step A: 2-(5-Bromo-2-fluoro-phenyl)-[1,3]dioxolane. A mixture of 5-bromo-2-fluoro-benzaldehyde (24.92 g, 123.2 mmol), ethylene glycol (21.0 mL, 369.6 mmol), toluene (650 mL), and TsOH (2.49 g, 12.4 mmol) were heated at reflux under a N$_2$ atmosphere in a flask fitted with a Dean Stark trap and condenser. After 18 h, the mixture was cooled to rt, washed with a satd. aq. NaHCO$_3$ and brine, dried (MgSO$_4$), and concentrated. Purification by FCC (EtOAc/hexanes) gave the desired product (28.74 g, 95%) as an oil. $^1$H NMR (CDCl$_3$): 7.68-7.63 (m, 1H), 7.45-7.39 (m, 1H), 6.98-6.91 (m, 1H), 6.05-6.00 (m, 1H), 4.12 (br s, 2H), 4.02 (br s, 2H).

Step B: 3-[1,3]-Dioxolan-2-yl-4-fluoro-benzaldehyde. To a −78° C. solution of 2-(5-bromo-2-fluoro-phenyl)-[1,3]dioxolane (1.024 g, 4.047 mmol) in THF (40 mL) was added 2.5 M n-BuLi (1.80 mL, 4.45 mmol). After 20 min, the reaction was quenched with DMF (1.60 mL). After stirring for 1 h, the mixture was diluted with DCM, washed with a satd. aq. NaHCO$_3$, dried (MgSO$_4$), and concentrated. Purification by FCC (EtOAc/hexanes) gave the desired product (406.5 mg, 87%) as a white solid. $^1$H NMR (acetone-d$_6$): 10.05 (s, 1H), 8.17-8.09 (m, 1H), 8.06-7.97 (m, 1H), 7.43-7.33 (m, 1H), 6.10-6.04 (m, 1H), 4.19-4.11 (m, 2H), 4.08-4.00 (m, 2H).

Step C: 1-(3-[1,3]Dioxolan-2-yl-4-fluoro-benzyl)-4-isopropyl-piperazine. The title compound was prepared in an analogous fashion to Example 1, Step B, using NaBH(OAc)$_3$ instead of NaBH$_4$ (770.8 mg, 85%). MS (ESI): mass calcd. for $C_{17}H_{25}FN_2O_2$, 308.19; m/z found, 309.4 [M+H]+. $^1$H NMR (CDCl$_3$): 7.45 (dd, J=6.9, 1H), 7.34-7.30 (m, 1H), 7.03-6.98 (m, 1H), 6.06 (s, 1H), 4.18-4.15 (m, 2H), 4.06-4.03 (m, 2H), 3.47 (s, 2H), 2.68-2.38 (m, 9H), 1.04 (d, J=6.5, 6H).

Step D: 2-Fluoro-5-(4-isopropyl-piperazin-1-ylmethyl)-benzaldehyde. A mixture of 1-(3-[1,3] dioxolan-2-yl-4-fluoro-benzyl)-4-isopropyl-piperazine (695.2 mg, 2.25 mmol) and 6 N HCl (25 mL) was stirred at rt for 50 min, then was diluted with DCM (250 mL), and quenched slowly with 1 N NaOH. The organic layer was separated, dried (Na$_2$SO$_4$), and concentrated to give the desired product (573.5 mg, 96%). MS (ESI): mass calcd. for $C_{15}H_{21}FN_2O$, 264.16; m/z found, 265.3 [M+H]+. $^1$H NMR (MeOD): 10.29 (s, 1H), 7.82-7.81 (m, 1H), 7.68-7.66 (m, 1H), 7.58-7.56 (m, 1H), 7.31-7.28 (m, 1H), 7.26-7.04 (m, 1H), 7.03-7.01 (t, J=8.4, 1H), 3.55 (s, 1H), 3.50 (s, 1H), 2.64-2.40 (br m, 9H), 1.07-1.06 (m, 6H).

Step E: 5-(4-Isopropyl-piperazin-1-ylmethyl)-2-(4-methylsulfanyl-phenoxy)-benzaldehyde. A mixture of 2-fluoro-5-(4-isopropyl-piperazin-1-ylmethyl)-benzaldehyde (513.7 mg, 1.943 mmol), 4-methylsulfanyl-phenol (326.8 mg, 2.138 mmol), and K$_2$CO$_3$ (845.2 mg, 5.829 mmol) in DMF (9.0 mL)

was heated at 90° C. for 3 days. After cooling to rt, the mixture was diluted with Et$_2$O, washed with 1 N NaOH and brine, dried (Na$_2$SO$_4$), and concentrated. Purification by FCC followed by reverse phase chromatography gave the desired product (804.5 mg, >100%). MS (ESI): mass calcd. for C$_{22}$H$_{28}$N$_2$O$_2$S, 384.19; m/z found, 385.3 [M+H]$^+$.

Step F. The title compound was prepared in an analogous fashion to Example 1, Step B, using NaB(OAc)$_3$H, to give the desired product. MS (ESI): mass calcd. for C$_{25}$H$_{35}$N$_3$OS, 425.25; m/z found, 426.4 [M+H]$^+$. $^1$H NMR (MeOD): 7.42-7.40 (m, 1H), 7.29 (d, J=8.8, 2H), 7.23 (dd, J=8.3, 2.1, 1H), 6.92 (d, J=8.8, 2H), 6.84 (d, J=8.3, 1H), 4.88 (s, 2H), 3.83 (s, 2H), 3.53 (s, 2H), 2.68-2.49 (m, 8H), 2.46 (s, 3H), 2.15-2.09 (m, 1H), 1.08 (d, J=6.5, 6H), 0.46-0.42 (m, 2H), 0.38-0.34 (m, 2H).

The compounds in Examples 61-65 were prepared by a sequence similar to that described in Example 60.

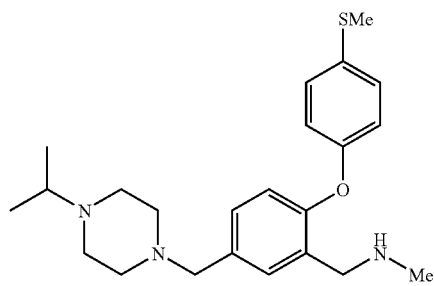

Example 61

[5-(4-Isopropyl-piperazin-1-ylmethyl)-2-(4-methyl-sulfanyl-phenoxy)-benzyl]-methyl-amine MS (ESI): mass calcd. for C$_{23}$H$_{33}$N$_3$OS, 399.23; m/z found, 400.40 [M+H]$^+$. $^1$H NMR (MeOD): 7.40-7.38 (m, 1H), 7.30-7.28 (m, 2H), 7.24-7.22 (m, 1H), 6.93-6.91 (m, 2H), 6.82 (d, J=8.0, 1H), 3.73 (s, 2H), 3.53 (s, 2H), 2.66-2.50 (m, 9H), 2.45 (s, 3H), 2.36 (s, 3H), 1.08 (d, J=6.5, 6H).

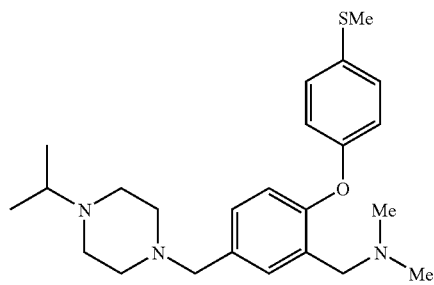

Example 62

[5-(4-Isopropyl-piperazin-1-ylmethyl)-2-(4-methyl-sulfanyl-phenoxy)-benzyl]-dimethyl-amine $^1$H NMR (MeOD): 7.41 (d, J=2.0, 1H), 7.29-7.26 (m, 2H), 7.26-7.24 (m, 1H), 6.90-6.88 (m, 2H), 6.83 (d, J=8.5, 1H), 3.54 (s, 4H), 2.74-2.48 (br m, 9H), 2.45 (s, 3H), 2.27 (s, 6H), 1.08 (d, J=6.5, 6H).

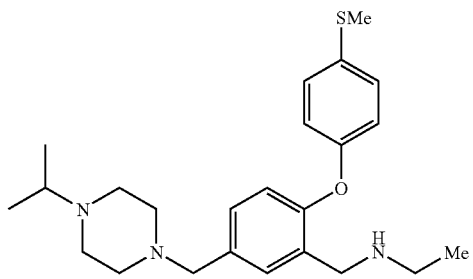

Example 63

Ethyl-[5-(4-isopropyl-piperazin-1-ylmethyl)-2-(4-methylsulfanyl-phenoxy)-benzyl]-amine MS (ESI): mass calcd. for C$_{24}$H$_{35}$N$_3$OS, 413.25; m/z found, 414.4 [M+H]$^+$. $^1$H NMR (MeOD): 7.42-7.39 (m, 1H), 7.30 (d, J=8.8, 2H), 7.24 (dd, J=8.3, 2.1, 1H), 6.92 (d, J=8.8, 2H), 6.84 (d, J=8.3, 1H), 4.91 (s, 3H), 3.78 (s, 2H), 3.54 (s, 2H), 2.68-2.48 (m, 9H), 2.46 (s, 3H), 1.12-1.06 (m, 9H).

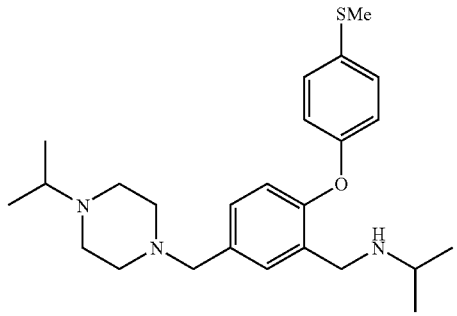

Example 64

Isopropyl-[5-(4-isopropyl-piperazin-1-ylmethyl)-2-(4-methylsulfanyl-phenoxy)-benzyl]-amine MS (ESI): mass calcd. for C$_{25}$H$_{37}$N$_3$OS, 427.27; m/z found, 428.4 [M+H]$^+$. $^1$H NMR (MeOD): 7.44 (d, J=2.0, 1H), 7.29 (d, J=8.7, 2H), 7.23 (dd, J=8.3, 2.1, 1H), 6.91 (d, J=8.9, 2H), 6.84 (d, J=8.3, 1H), 4.90 (s, 3H), 3.77 (s, 2H), 3.53 (s, 2H), 2.80-2.73 (m, 1H), 2.72-2.47 (m, 7H), 2.45 (s, 3H), 1.08 (d, J=6.5, 6H), 1.05 (d, J=6.3, 6H).

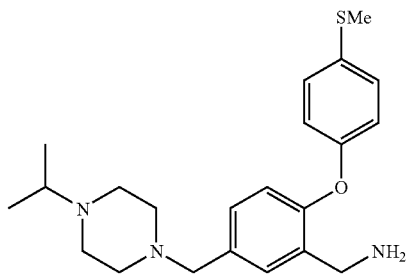

Example 65

5-(4-Isopropyl-piperazin-1-ylmethyl)-2-(4-methyl-sulfanyl-phenoxy)-benzylamine

MS (ESI): mass calcd. for C$_{22}$H$_{31}$N$_3$OS, 385.22; m/z found, 386.4 [M+H]$^+$. $^1$H NMR (MeOD): 7.43-7.39 (m, 1H), 7.27 (d, J=8.8, 2H), 7.20 (dd, J=8.3, 2.0, 1H), 6.91 (d, J=8.8, 2H), 6.80 (d, J=8.2, 1H), 4.95-4.86 (m, 2H), 3.80 (s, 2H), 3.52 (s, 2H), 2.74-2.47 (m, 7H), 2.45 (s, 3H), 1.08 (d, J=6.5, 6H).

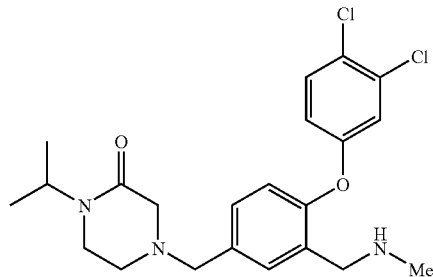

Example 66

4-[4-(3,4-Dichloro-phenoxy)-3-methylaminomethyl-benzyl]-1-isopropyl-piperazin-2-one Step A: [2-(3,4-Dichloro-phenoxy)-5-formyl-benzyl]-methyl-carbamic acid tert-butyl ester. The title compound was prepared from [5-bromo-2-(3,4-dichloro-phenoxy) benzyl] methyl carbamic acid tert-butyl ester (Example 1, Steps A-C) in analogous fashion to Example 60, Step B.

Step B: [2-(3,4-Dichloro-phenoxy)-5-(3-oxo-piperazin-1-ylmethyl)-benzyl]-methyl-carbamic acid tert-butyl ester. The title compound was prepared in analogous fashion to Example 60, Step C.

Step C: [2-(3,4-Dichloro-phenoxy)-5-(4-isopropyl-3-oxo-piperazin-1-ylmethyl)-benzyl]-methyl-carbamic acid tert-butyl ester. To a solution of [2-(3,4-dichloro-phenoxy)-5-(3-oxo-piperazin-1-ylmethyl)-benzyl]-methyl-carbamic acid tert-butyl ester 79 mg, 0.16 mmol) in DMF (3.2 mL) at 0° C. was added NaH (90%, 7.6 mg). After 30 min, 2-bromopropane (15 µL, 0.16 mmol) was added and the reaction was allowed to come to rt and stir overnight. The mixture was quenched with satd. aq. NaHCO$_3$ and extracted with DCM. The combined organic layers were dried (Na$_2$SO$_4$) and concentrated. The crude product was purified by FCC to provide the title compound (35 mg, 41%). MS (ESI): mass calcd. for C$_{27}$H$_{35}$Cl$_2$N$_3$O$_4$, 535.20; m/z found, 536.2 [M+H].

Step D. The title compound was prepared in an analogous fashion to Example 1, Step E. MS (ESI): mass calcd. for C$_{22}$H$_{27}$Cl$_2$N$_3$O$_2$, 435.15; m/z found, 436.1 [M+H]$^+$.

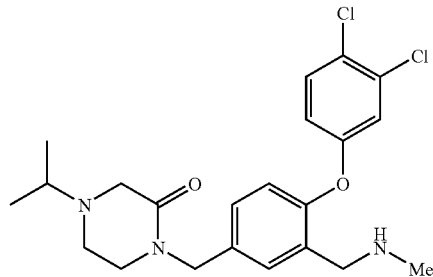

Example 67

1-[4-(3,4-Dichloro-phenoxy)-3-methylaminomethyl-benzyl]-4-isopropyl-piperazin-2-one Step A: [2-(3,4-Dichloro-phenoxy)-5-hydroxymethyl-benzyl]-methyl-carbamic acid tert-butyl ester. To a solution of [2-(3,4-dichloro-phenoxy)-5-formyl-benzyl]-methyl-carbamic acid tert-butyl ester (816 mg, 1.98 mmol) in MeOH (40 mL), was added NaBH$_4$ (75 mg, 1.98 mmol). After 24 h, the mixture was treated with 1 N NaOH, was stirred an additional 1 h, and then partially concentrated. The resulting aqueous mixture was extracted with DCM and the combined organic layers were dried (Na$_2$SO$_4$) and concentrated. The crude material was carried forward without further purification (784 mg, 96%). MS (ESI): mass calcd. for C$_{20}$H$_{23}$Cl$_2$NO$_4$, 411.10; m/z found, 434.7 [M+Na]$^+$.

Step B: [5-Chloromethyl-2-(3,4-dichloro-phenoxy)-benzyl]-methyl-carbamic acid tert-butyl ester. To a solution of 2-(3,4-dichloro-phenoxy)-5-hydroxymethyl-benzyl]-methyl-carbamic acid tert-butyl ester (248 mg, 0.61 mmol) in DCM was added K$_2$CO$_3$ (250 mg, 1.80 mmol). The mixture was cooled to 0° C. and SOCl$_2$ (85 µL, 1.2 mmol) was added. After 2 h, the solids were filtered off and the filtrate was concentrated. Purification by FCC gave the desired product (241 mg, 93%). MS (ESI): mass calcd. for C$_{20}$H$_{22}$Cl$_3$NO$_3$, 429.07; m/z found, 330.6[M+H-Boc]$^+$.

Step C: [2-(3,4-Dichloro-phenoxy)-5-(4-isopropyl-2-oxo-piperazin-1-ylmethyl)-benzyl]-methyl-carbamic acid tert-butyl ester. To a solution of 4-isopropyl-piperazin-2-one (32 mg, 0.22 mmol) in DMF (2.2 mL) at 0° C. was added NaH (90%, 11 mg). After 30 min, a solution of [5-chloromethyl-2-(3,4-dichloro-phenoxy)-benzyl]-methyl-carbamic acid tert-butyl ester (96 mg, 0.22 mmol) in DMF (2.2 mL) was added and the reaction was allowed to come to rt and stir overnight. The mixture was quenched with satd. aq. NaHCO$_3$ and extracted with DCM. The combined organic layers were dried (Na$_2$SO$_4$) and concentrated. The crude product was purified by FCC to provide the desired product (94 mg, 79%). MS (ESI): mass calcd. for C$_{27}$H$_{35}$Cl$_2$N$_3$O$_4$, 535.20; m/z found, 536.2 [M+H].

Step D. The title compound was prepared in an analogous fashion to Example 1, Step E. MS (ESI): mass calcd. for C$_{22}$H$_{27}$Cl$_2$N$_3$O$_2$, 435.15; m/z found, 436.1 [M+H].

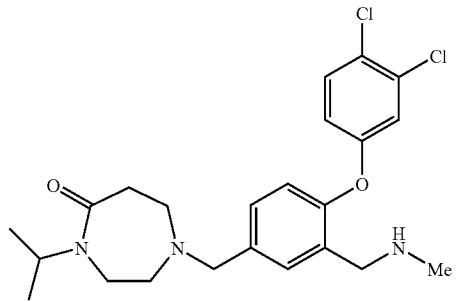

Example 68

1-[4-(3,4-Dichloro-phenoxy)-3-methylaminomethyl-benzyl]-4-isopropyl-[1,4]diazepan-5-one MS (ESI): mass calcd. for C$_{23}$H$_{29}$Cl$_2$N$_3$O$_2$, 449.16; m/z found, 450.1 [M+H]$^+$.

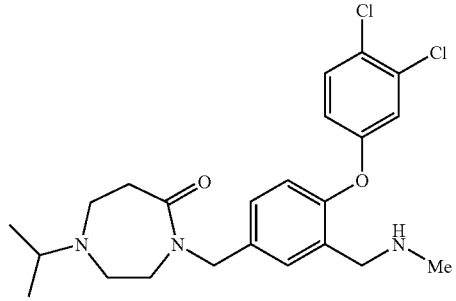

Example 69

4-[4-(3,4-Dichloro-phenoxy)-3-methylaminomethyl-benzyl]-1-isopropyl-[1,4]diazepan-5-one MS (ESI): mass calcd. for $C_{23}H_{29}Cl_2N_3O_2$, 449.16; m/z found, 450.2 [M+H]$^+$.

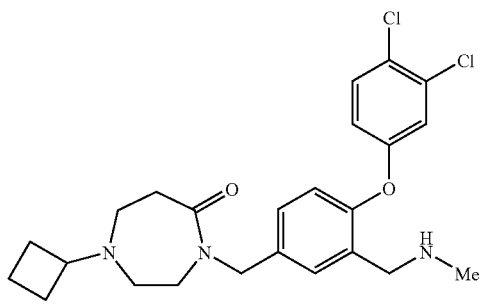

Example 70

1-Cyclobutyl-4-[4-(3,4-dichloro-phenoxy)-3-methylaminomethyl-benzyl]-[1,4]diazepan-5-one MS (ESI): mass calcd. for $C_{24}H_{29}Cl_2N_3O_2$, 461.16; m/z found, 462.1 [M+H]$^+$.

The compounds in Examples 71-88 were prepared using methods analogous to those described in the preceding examples.

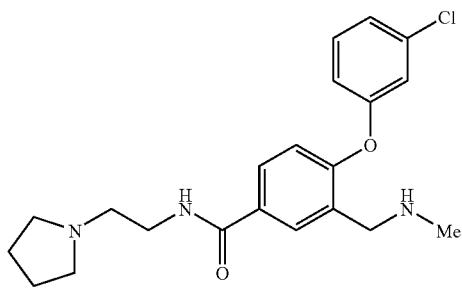

Example 71

4-(3-Chloro-phenoxy)-3-methylaminomethyl-N-(2-pyrrolidin-1-yl-ethyl)-benzamide

MS (ESI): m/z found, 388.7 [M+H]$^+$.

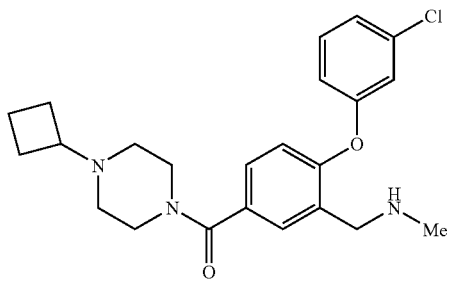

Example 72

[4-(3-Chloro-phenoxy)-3-methylaminomethyl-phenyl]-(4-cyclobutyl-piperazin-1-yl)-methanone MS (ESI): m/z found, 414.8 [M+H]$^+$.

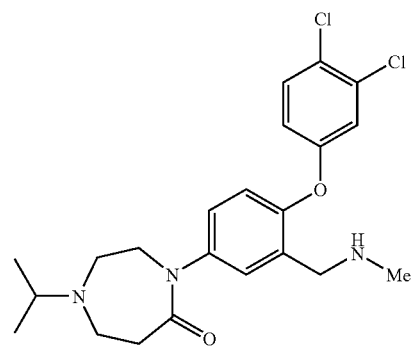

Example 73

4-[4-(3,4-Dichloro-phenoxy)-3-methylaminomethyl-phenyl]-1-isopropyl-[1,4]diazepan-5-one MS (ESI): m/z found, 436.8 [M+H]$^+$.

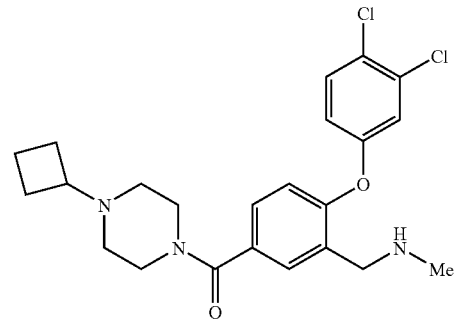

Example 74

(4-Cyclobutyl-piperazin-1-yl)-[4-(3,4-dichloro-phenoxy)-3-methylaminomethyl-phenyl]-methanone MS (ESI): m/z found, 448.2 [M+H]$^+$.

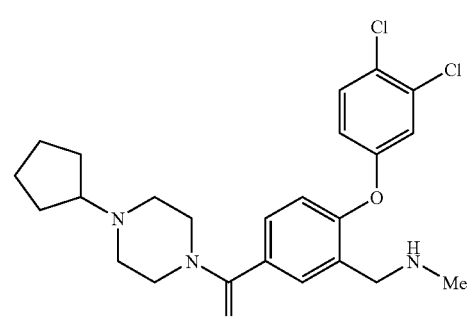

Example 75

(4-Cyclopentyl-piperazin-1-yl)-[4-(3,4-dichloro-phenoxy)-3-methylaminomethyl-phenyl]-methanone MS (ESI): m/z found, 462.3 [M+H]$^+$.

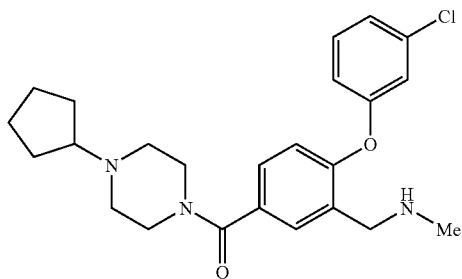

Example 76

[4-(3-Chloro-phenoxy)-3-methylaminomethyl-phenyl]-(4-cyclopentyl-piperazin-1-yl)-methanone MS (ESI): m/z found, 428.4 [M+H]$^+$.

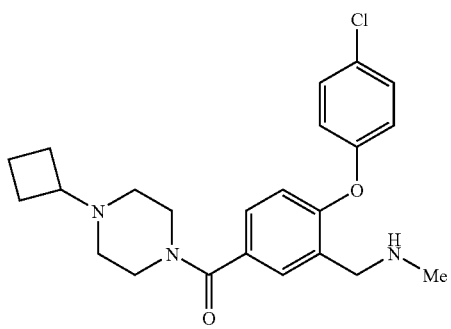

Example 77

[4-(4-Chloro-phenoxy)-3-methylaminomethyl-phenyl]-(4-cyclobutyl-piperazin-1-yl)-methanone MS (ESI): m/z found, 414.3 [M+H]$^+$.

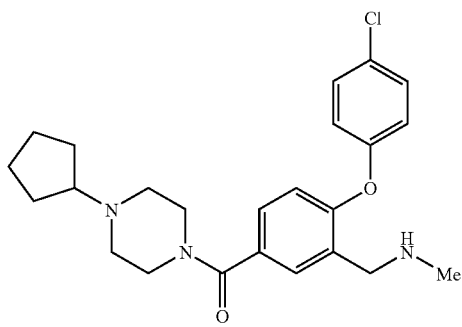

Example 78

[4-(4-Chloro-phenoxy)-3-methylaminomethyl-phenyl]-(4-cyclopentyl-piperazin-1-yl)-methanone MS (ESI): m/z found, 428.4 [M+H]$^+$.

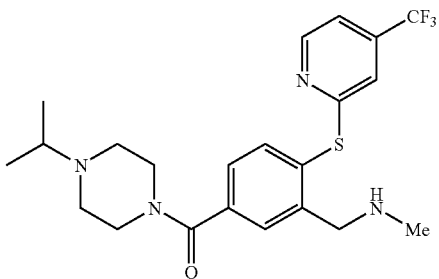

Example 79

(4-Isopropyl-piperazin-1-yl)-[3-methylaminomethyl-4-(4-trifluoromethyl-pyridin-2-ylsulfanyl)-phenyl]-methanone

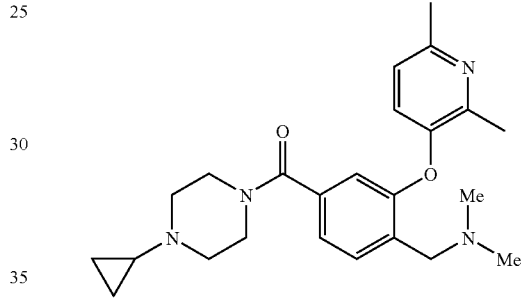

Example 80

(4-Cyclopropyl-piperazin-1-yl)-[4-dimethylaminomethyl-3-(2,6-dimethyl-pyridin-3-yloxy)-phenyl]-methanone MS (ESI): m/z found, 409.3 [M+H]$^+$.

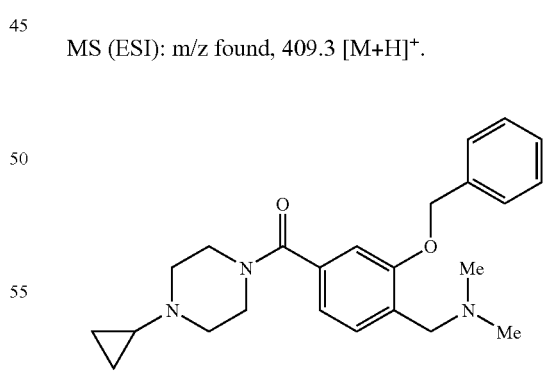

Example 81

(3-Benzyloxy-4-dimethylaminomethyl-phenyl)-(4-cyclopropyl-piperazin-1-yl)-methanone MS (ESI): m/z found, 394.3 [M+H]$^+$.

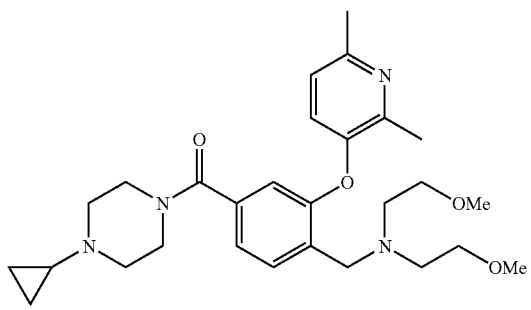

Example 82

[4-{[Bis-(2-methoxy-ethyl)-amino]-methyl}-3-(2,6-dimethyl-pyridin-3-yloxy)-phenyl]-(4-cyclopropyl-piperazin-1-yl)-methanone MS (ESI): m/z found, 497.3 [M+H]$^+$.

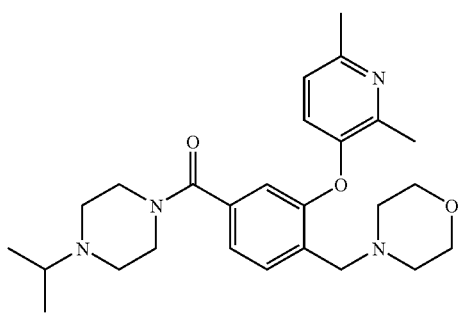

Example 83

[3-(2,6-Dimethyl-pyridin-3-yloxy)-4-morpholin-4-ylmethyl-phenyl]-(4-isopropyl-piperazin-1-yl)-methanone MS (ESI): m/z found, 453.3 [M+H]$^+$.

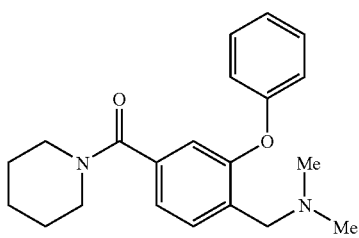

Example 84

(4-Dimethylaminomethyl-3-phenoxy-phenyl)-piperidin-1-yl-methanone

MS (ESI): m/z found, 339.2 [M+H]$^+$.

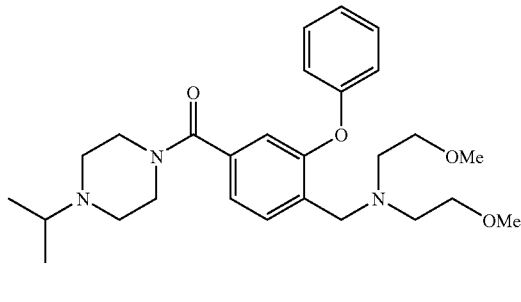

Example 85

(4-{[Bis-(2-methoxy-ethyl)-amino]-methyl}-3-phenoxy-phenyl)-(4-isopropyl-piperazin-1-yl)-methanone MS (ESI): m/z found, 470.3 [M+H]$^+$.

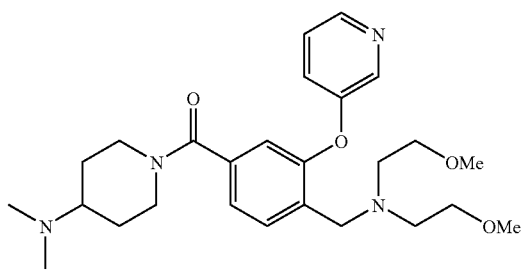

Example 86

[4-{[Bis-(2-methoxy-ethyl)-amino]-methyl}-3-(pyridin-3-yloxy)-phenyl]-(4-dimethylamino-piperidin-1-yl)-methanone MS (ESI): m/z found, 471.3 [M+H]$^+$.

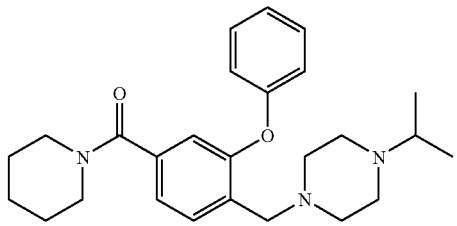

Example 87

[4-(4-Isopropyl-piperazin-1-ylmethyl)-3-phenoxy-phenyl]-piperidin-1-yl-methanone MS (ESI): m/z found, 422.3 [M+H]$^+$.

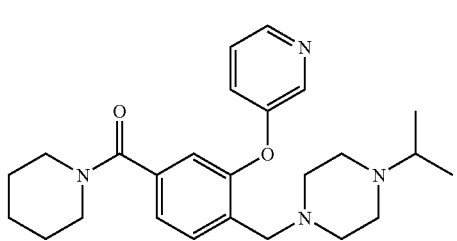

Example 88

[4-(4-Isopropyl-piperazin-1-ylmethyl)-3-(pyridin-3-yloxy)-phenyl]-piperidin-1-yl-methanone MS (ESI): m/z found, 423.3 [M+H]$^+$.

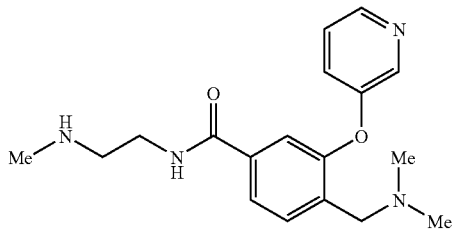

Example 89

4-Dimethylaminomethyl-N-(2-methylamino-ethyl)-3-(pyridin-3-yloxy)-benzamide

To a solution of {2-[4-dimethylaminomethyl-3-(pyridin-3-yloxy)-benzoylamino]-ethyl}-methyl-carbamic acid tert-butylester (250 mg, 0.58 mmol) in CH$_2$Cl$_2$ (3 mL) was added trifluoroacetic acid (1 mL). The reaction was allowed to stir at rt for 16 h and then concentrated under reduced pressure. The residue was dissolved in CH$_2$Cl$_2$ (50 mL), washed with 1 M NaOH (15 mL), dried (Na$_2$SO$_4$), and concentrated under reduced pressure. FCC purification (MeOH/CH$_2$Cl$_2$) provided the desired product (0.13 g, 68%) as a yellow oil. MS (ESI): m/z found, 329.2 [M+H]$^+$.

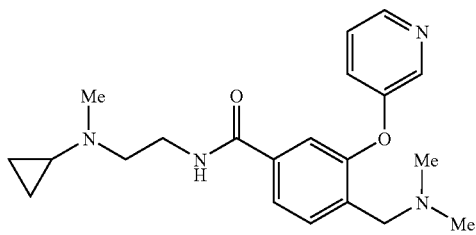

Example 90

N-[2-(Cyclopropyl-methyl-amino)-ethyl]-4-dimethylaminomethyl-3-(pyridin-3-yloxy)-benzamide To a solution of 4-dimethylaminomethyl-N-(2-methylamino-ethyl)-3-(pyridin-3-yloxy)-benzamide (0.090 g, 0.274 mmol) in a 1:1 mixture of THF:MeOH (4 mL) was added [(1-ethoxycyclopropyl)-oxy]trimethylsilane (0.28 mL, 1.37 mmol), AcOH (0.08 mL, 1.37 mmol), and NaCNBH$_3$ (0.088 g, 1.37 mmol). The reaction mixture was heated to 50° C. for 24 h, cooled to rt and concentrated under reduced pressure. The residue was dissolved in CH$_2$Cl$_2$ (15 mL), washed with sat. NaHCO$_3$ (5 mL), dried (Na$_2$SO$_4$), and concentrated. HPLC purification under basic conditions yielded the desired product (0.036 g, 38%). MS (ESI): m/z found, 369.2 [M+H]$^+$.

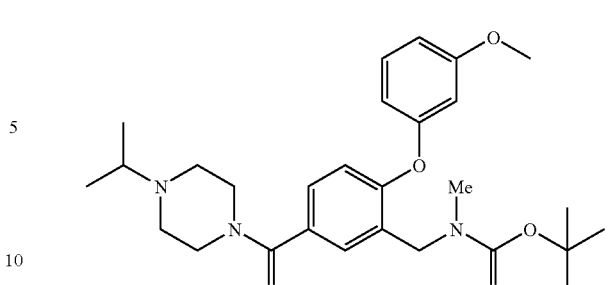

Example 91

[5-(4-Isopropyl-piperazine-1-carbonyl)-2-(3-methoxy-phenoxy)-benzyl]-methyl-carbamic acid tert-butyl ester The title compound was prepared using methods analogous to those described in the preceding examples.

Biological Methods:

Compounds were tested as the free base, hydrochloride salt, TFA salt, or citric acid salt forms.

H$_3$ Receptor Binding

Binding of compounds to the cloned human and rat H$_3$ receptors, stably expressed in SK-N-MC cells, was performed as described by Barbier, A. J. et al. (Br. J. Pharmacol. 2004, 143(5), 649-661). Data for compounds tested in this assay are presented in Table 1.

Rat Brain SERT

A rat brain without cerebellum (Zivic Laboratories, Inc.—Pittsburgh, Pa.) was homogenized in a 52.6 mM Tris pH 8/126.4 mM NaCl/5.26 mM KCl mixture and centrifuged at 1,000 rpm for 5 min. The supernatant was removed and re-centrifuged at 15,000 rpm for 30 min. Pellets were re-homogenized in a 52.6 mM Tris pH8/126.4 mM NaCl/5.26 mM KCl mixture. Membranes were incubated with 0.6 nM [$^3$H]-Citalopram plus/minus test compounds for 60 min at 25° C. and harvested by rapid filtration over GF/C glass fiber filters (pretreated with 0.3% polyethylenimine) followed by four washes with ice-cold buffer. Nonspecific binding was defined in the presence of 100 μM fluoxetine. IC$_{50}$ values were determined by a single site curve-fitting program (GraphPad, San Diego, Calif.) and converted to K$_i$ values based on a [$^3$H]-Citalopram K$_d$ of 0.6 nM and a ligand concentration of 0.6 nM. Data for compounds tested in this assay are presented in Table 1. NT=not tested.

TABLE 1

| Ex. | Human H$_3$ K$_i$ (nM) | Rat SERT K$_i$ (nM) |
| --- | --- | --- |
| 1 | 2.4 | 4.9 |
| 2 | 29 | 4.0 |
| 3 | 2.2 | 1.8 |
| 4 | 4.3 | 5.8 |
| 5 | 23 | 9.3 |
| 6 | 1.1 | 18 |
| 7 | 1.1 | 8.2 |
| 8 | 0.8 | 90 |
| 9 | 1 | 160 |
| 10 | 33 | 260 |
| 11 | 14 | 113 |
| 12 | 8 | 230 |
| 13 | 15 | 102 |
| 14 | 37 | 16 |
| 15 | 22 | 2000 |
| 16 | 21 | 4.2 |

TABLE 1-continued

| Ex. | Human H$_3$ K$_i$ (nM) | Rat SERT K$_i$ (nM) |
|---|---|---|
| 17 | 1.5 | 1500 |
| 18 | 11 | 9.7 |
| 19 | 14 | 40 |
| 20 | 59 | 190 |
| 21 | 32 | 19 |
| 22 | 18 | 21 |
| 23 | 50 | 3 |
| 24 | 31 | 130 |
| 25 | 7 | 0.9 |
| 26 | 100 | 3 |
| 27 | 48 | 0.8 |
| 28 | 150 | NT |
| 29 | 170 | 10000 |
| 30 | 3 | 4000 |
| 31 | 10 | 1000 |
| 32 | 26 | 6000 |
| 33 | 2 | 10000 |
| 34 | 3 | 10000 |
| 35 | 7 | 10000 |
| 36 | 4 | 28 |
| 37 | 1 | 2 |
| 38 | 4 | 130 |
| 39 | 15 | 17 |
| 40 | 7 | 0.1 |
| 41 | 210 | 0.4 |
| 42 | 6 | 0.3 |
| 43 | 110 | 0.7 |
| 44 | 160 | 0.5 |
| 45 | 76 | 1 |
| 46 | 49 | 4 |
| 47 | 20 | 2 |
| 48 | 5500 | 0.4 |
| 49 | 400 | 2 |
| 50 | 150 | 7 |
| 51 | 28 | 2 |
| 52 | 8 | 1 |
| 53 | 28 | 6 |
| 54 | 3 | 0.5 |
| 55 | 27 | 10 |
| 56 | 25 | 16 |
| 57 | 37 | 4 |
| 58 | 300 | 6 |
| 59 | 70 | 4 |
| 60 | 2 | 3 |
| 61 | 2 | 0.8 |
| 62 | 21 | 1 |
| 63 | 0.9 | 6 |
| 64 | 0.5 | 7 |
| 65 | 4 | 18 |
| 66 | 2500 | 6 |
| 67 | 6 | 4 |
| 68 | 6300 | 7 |
| 69 | 110 | 4 |
| 70 | 19 | 5 |
| 71 | 6 | 2 |
| 72 | 4 | 65 |
| 73 | 7.7 | 12 |
| 74 | 4 | 9 |
| 75 | 20 | 11 |
| 76 | 2 | 28 |
| 77 | 2.4 | 10 |
| 78 | 3.4 | 8.1 |
| 79 | 28 | 3150 |
| 80 | 140 | 500 |
| 81 | 67 | 8000 |
| 82 | 200 | NT |
| 83 | 21 | NT |
| 84 | 4500 | NT |
| 85 | 12 | NT |
| 86 | 200 | NT |
| 87 | 280 | NT |
| 88 | 220 | NT |
| 89 | 1900 | NT |
| 90 | 45 | NT |
| 91 | 58 | NT |

Human SERT

Homogenized HEK293 (Human Embryonic Kidney) membranes expressing the human SERT were incubated with $^3$H-citalopram (SERT) at rt for 1 h in 50 mM Tris, 120 mM NaCl, 5 mM KCl (pH 7.4). Nonspecific binding was determined in the presence of 10 μM fluoxetine for the SERT. The membranes were washed and the radioactivity was counted as above. Calculations for K$_i$ at the SERT were based on a K$_d$ value for $^3$H-citalopram and a ligand concentration of 3.1 nM. Data for compounds tested in this assay are presented in Table 2.

TABLE 2

| Ex. | Human SERT K$_i$ (nM) |
|---|---|
| 1 | 6.3 |
| 2 | 5.0 |
| 3 | 5.9 |
| 4 | 8.1 |
| 5 | 6.8 |
| 6 | 28 |
| 7 | 24 |
| 9 | 420 |
| 11 | 155 |
| 12 | 380 |
| 13 | 363 |
| 14 | 37 |
| 16 | 11 |
| 17 | 2000 |
| 18 | 23 |
| 73 | 16 |
| 75 | 15 |
| 77 | 39 |
| 78 | 24 |

Cyclic AMP Accumulation

Sublines of SK-N-MC cells were created that expressed a reporter construct and the human H$_3$ receptor. The reporter gene (β-galactosidase) is under the control of multiple cyclic AMP responsive elements. In 96-well plates, histamine was added directly to the cell media followed 5 min later by an addition of forskolin (5 μM final concentration). When appropriate, antagonists were added 10 min prior to agonist addition. After a 6-h incubation at 37° C., the media was aspirated and the cells washed with 200 μL of phosphate-buffered saline followed by a second aspiration. Cells were lysed with 25 μL 0.1× assay buffer (10 mM Na-phosphate, pH 8, 0.2 mM MgSO$_4$, 0.01 mM MnCl$_2$) and incubated at rt for 10 min. Cells were then incubated for 10 min with 100 μL of 1× assay buffer containing 0.5% Triton and 40 mM, βmercaptoethanol. Color was developed using 25 μL of 1 mg/mL substrate solution (chlorophenolred β-D galactopyranoside; Roche Molecular Biochemicals, Indianapolis, Ind.). Color was quantitated on a microplate reader at absorbance 570 nM. The pA$_2$ values were calculated by Schild regression analysis of the pEC$_{50}$ values and are presented for compounds tested in Table 3.

TABLE 3

| Ex. | pA$_2$ |
|---|---|
| 1 | 8.14 |
| 3 | 8.57 |
| 4 | 8.12 |
| 5 | 8.11 |
| 6 | 8.61 |
| 7 | 8.64 |
| 30 | 9.1 |

TABLE 3-continued

| Ex. | pA$_2$ |
|---|---|
| 31 | 8.8 |
| 33 | 9.5 |
| 34 | 8.9 |
| 35 | 8.6 |
| 36 | 8.2 |
| 54 | 8.7 |
| 73 | 8.35 |

What is claimed is:

1. A compound of Formula (I):

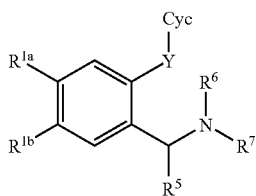

wherein
one of $R^{1a}$ and $R^{1b}$ is

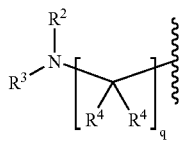

and the other is —H;

$R^2$ and $R^3$ taken together with the nitrogen to which they are attached form a piperazine group unsubstituted or substituted on a carbon ring member with one, two, or three $R^d$ moieties and substituted on a nitrogen ring member with an $R^e$ moiety;

where each $R^d$ moiety is independently selected from the group consisting of: —$C_{1-6}$alkyl; —$C_{1-4}$alkyl-OH; halo; —OH; —$OC_{1-6}$alkyl; ipso-substituted —$OC_{2-3}$alkylO—; —CN; —NO$_2$; —N($R^g$)$R^h$; —C(O)N($R^g$)$R^h$; —N($R^g$)SO$_2C_{1-6}$alkyl; —C(O)$C_{1-6}$alkyl; —S(O)$_{0-2}$—$C_{1-6}$alkyl; —SO$_2$N($R^g$)$R^h$; —SCF$_3$; —CF$_3$; —OCF$_3$; —CO$_2$H; and —CO$_2C_{1-6}$alkyl;

where $R^g$ and $R^h$ are each independently —H or —$C_{1-6}$alkyl, or $R^g$ and $R^h$ taken together with their nitrogen of attachment form a monocyclic heterocycloalkyl group; and where $R^e$ is selected from the group consisting of: —H; a —$C_{1-6}$alkyl or —C(O)$C_{1-6}$alkyl group unsubstituted or substituted with halo, —CN, —OH, —$OC_{1-4}$ alkyl, or —CF$_3$; —C(O)CF$_3$; —S(O)$_{0-2}$—$C_{1-6}$alkyl; —CO$_2C_{1-6}$alkyl; and a phenyl, monocyclic carbon-linked heteroaryl, monocyclic cycloalkyl, or monocyclic carbon-linked heterocycloalkyl group, each unsubstituted or substituted with —$C_{1-4}$alkyl, halo, —CN, —OH, —$OC_{1-4}$alkyl, or —CF$_3$;

q is 0 or 1;

each $R^4$ is independently —H or methyl, or both $R^4$ substituents taken together form a carbonyl;

Y is —O—, —OCH$_2$—, —S—, —SO—, or —SO$_2$—;

$R^5$ is —H or —$C_{1-6}$alkyl;

$R^6$ is —H; or —$C_{1-6}$alkyl, —$C_{3-6}$alkenyl, —$C_{3-6}$alkynyl, monocyclic cycloalkyl, or —$C_{1-6}$alkyl-(monocyclic cycloalkyl), each unsubstituted or substituted with —$C_{1-4}$alkyl, —OH, —$OC_{1-4}$alkyl, halo, —NH$_2$, —NH(C$_{1-4}$alkyl), —N(C$_{1-4}$alkyl)$_2$, —CN, —CO$_2$H, or —CO$_2C_{1-4}$alkyl;

$R^7$ is —H; or —$C_{1-6}$alkyl, —$C_{3-6}$alkenyl, —$C_{3-6}$alkynyl, monocyclic cycloalkyl, or —$C_{1-6}$alkyl-(monocyclic cycloalkyl), each unsubstituted or substituted with —$C_{1-4}$alkyl, —OH, —$OC_{1-4}$alkyl, halo, —NH$_2$, —NH(C$_{1-4}$alkyl), —N(C$_{1-4}$alkyl)$_2$, —CN, —CO$_2$H, or —CO$_2C_{1-4}$alkyl;

or $R^6$ and $R^7$ taken together with their nitrogen of attachment form a saturated monocyclic heterocycloalkyl group unsubstituted or substituted with —$C_{1-4}$alkyl, —$OC_{1-4}$alkyl, or halo; and Cyc is a phenyl or monocyclic carbon-linked heteroaryl group, unsubstituted or substituted with one, two, or three $R^k$ moieties;

where each $R^k$ moiety is independently selected from the group consisting of: —$C_{1-6}$alkyl, —CHF$_2$, —CF$_3$, —$C_{2-6}$alkenyl, —$C_{2-6}$alkynyl, —OH, —$OC_{1-6}$alkyl, —OCHF$_2$, —OCF$_3$, —$OC_{3-6}$alkenyl, —$OC_{3-6}$alkynyl, —CN, —NO$_2$, —N($R^l$)$R^m$, —N($R^l$)C(O)$R^m$, —N($R^l$)SO$_2C_{1-6}$alkyl, —C(O)$C_{1-6}$alkyl, —S(O)$_{0-2}$—$C_{1-6}$alkyl, —C(O)N($R^l$)$R^m$, —SO$_2$N($R^l$)$R^m$, —SCF$_3$, halo, —CO$_2$H, and —CO$_2C_{1-6}$alkyl; or two $R^k$ moieties on adjacent carbon atoms of attachment together are —$OC_{1-4}$alkyleneO— to form a cyclic ring which is unsubstituted or substituted with one or two fluoro substituents;

where $R^l$ and $R^m$ are each independently —H or —$C_{1-6}$alkyl;

or a pharmaceutically acceptable salt thereof.

2. A compound as defined in claim 1, wherein $R^{1b}$ is

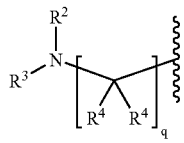

3. A compound as defined in claim 1, wherein $R^2$ and $R^3$ taken together with the nitrogen to which they are attached form piperazinyl, 4-methyl-piperazin-1-yl, 4-ethyl-piperazin-1-yl, 4-(2-fluoroethyl)-piperazin-1-yl, 4-isopropyl-piperazin-1-yl, 4-cyclopropyl-piperazin-1-yl, 4-cyclobutyl-piperazin-1-yl, 4-cyclopentyl-piperazin-1-yl, 4-(2-hydroxyethyl)piperazin-1-yl, 4-(2-methoxyethyl)-piperazin-1-yl, 4-(tert-butoxycarbonyl)piperazin-1-yl, 4-phenylpiperazin-1-yl, 4-(2-hydroxyphenyl)piperazinyl, 4-(4-trifluoromethyl-phenyl)-piperazin-1-yl, 4-thiazol-2-yl-piperazin-1-yl, 4-(2-thiophenyl)piperazinyl, 4-pyridin-4-yl-piperazin-1-yl, 4-acetylpiperazin-1-yl, 4-isobutyryl-piperazin-1-yl, 4-piperazin-2-onyl, 1-isopropyl-4-piperazin-2-onyl, 4-isopropyl-1-piperazin-2-onyl, or 1-cyclopropyl-4-piperazin-2-onyl.

4. A compound as defined in claim 1, wherein $R^2$ and $R^3$ taken together with the nitrogen to which they are attached form piperazinyl, 4-methyl-piperazin-1-yl, 4-isopropyl-piperazin-1-yl, 4-(2-fluoroethyl)-piperazin-1-yl, 4-cyclopropyl-piperazin-1-yl, 4-cyclobutyl-piperazin-1-yl, 4-cyclopentyl-piperazin-1-yl, 4-pyridin-4-yl-piperazin-1-yl, 4-piperazin-2-onyl, or 1-isopropyl-4-piperazin-2-onyl.

5. A compound as defined in claim 1, wherein each $R^d$ moiety is independently selected from the group consisting of: methyl, ethyl, isopropyl, hydroxyethyl, fluoro, methoxy, dimethylamino, piperidinyl, morpholinyl, acetyl, trifluoromethyl, —CO$_2$H, and —CO$_2$-methyl.

6. A compound as defined in claim 1, wherein $R^g$ and $R^h$ are each independently —H, methyl, ethyl, or isopropyl, or $R^g$ and $R^h$ taken together with their nitrogen of attachment form pyrrolidinyl, piperidinyl, morpolinyl, or thiomorpholinyl.

7. A compound as defined in claim 1, wherein $R^e$ is selected from the group consisting of: —H, methyl, ethyl, isopropyl, 2-fluoroethyl, hydroxyethyl, methoxypropyl, acetyl, tert-butoxycarbonyl, phenyl, 4-pyridyl, cyclopropyl, cyclobutyl, cyclopentyl, and piperidinyl.

8. A compound as defined in claim 1, wherein $R^e$ is selected from the group consisting of: —H, isopropyl, and cyclopropyl.

9. A compound as defined in claim 1, wherein q is 1 and both $R^4$ substituents taken together form a carbonyl.

10. A compound as defined in claim 1, wherein q is 0.

11. A compound as defined in claim 1, wherein q is 1 and each $R^4$ is —H.

12. A compound as defined in claim 1, wherein Y is —O— or —S—.

13. A compound as defined in claim 1, wherein Cyc is a phenyl or pyridyl group unsubstituted or substituted with one, two, or three $R^k$ moieties.

14. A compound as defined in claim 1, wherein Cyc is a thiophenyl, oxazolyl, thiazolyl, pyrazolyl, pyridinyl, or pyrazinyl group unsubstituted or substituted with one, two, or three $R^k$ moieties.

15. A compound as defined in claim 1, wherein Cyc is phenyl, 2-hydroxyphenyl, 3-hydroxyphenyl, 4-hydroxyphenyl, 4-hydroxy-2-methylphenyl, 4-hydroxy-3-fluorophenyl, 3,4-dihydroxyphenyl, 2-methoxyphenyl, 3-methoxyphenyl, 4-methoxyphenyl, 4-ethoxyphenyl, 2,4-dimethoxyphenyl, 2,5-dimethoxyphenyl, 3,4-dimethoxyphenyl, 3,5-dimethoxyphenyl, 3,4,5-trimethoxyphenyl, 2-methylphenyl, 3-methylphenyl, 4-methylphenyl, 4-ethylphenyl, 3-ethynylphenyl, 4-ethynylphenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 3-iodophenyl, 4-iodophenyl, 2,3-difluorophenyl, 2,4-difluorophenyl, 3,4-difluorophenyl, 2,3-dichlorophenyl, 2,4-dichlorophenyl, 2,5-dichlorophenyl, 3,4-dichlorophenyl, 3,5-dichlorophenyl, 2-fluoro-3-chlorophenyl, 2-fluoro-4-chlorophenyl, 2-chloro-4-fluorophenyl, 3-fluoro-4-chlorophenyl, 3-chloro-4-fluorophenyl, 4-fluoro-3-methylphenyl, 3-chloro-4-methoxyphenyl, 2-fluoro-4-methoxyphenyl, 3-fluoro-4-methoxyphenyl, 3-chloro-4-difluoromethoxyphenyl, 4-chloro-3-trifluoromethylphenyl, 2-trifluoromethylphenyl, 3-trifluoromethylphenyl, 4-trifluoromethylphenyl, 3-trifluoromethoxyphenyl, 4-trifluoromethoxyphenyl, 4-difluoromethoxyphenyl, 2-cyanophenyl, 3-cyanophenyl, 4-cyanophenyl, 3-acetylphenyl, 4-acetylphenyl, 3-nitrophenyl, 4-nitrophenyl, 4-aminophenyl, 4-dimethylaminophenyl, 4-carbamoylphenyl, 4-methanesulfanylphenyl, 4-methanesulfinylphenyl, 4-methanesulfonylphenyl, 4-trifluoromethanesulfanylphenyl, 3-methyl-4-methylsulfanylphenyl, benzo[1,3]dioxol-4-yl, benzo[1,3]dioxol-5-yl, thiophen-2-yl, thiophen-3-yl, oxazol-5-yl, thiazol-5-yl, thiazol-2-yl, 2H-pyrazol-3-yl, 2-pyridinyl, 3-pyridinyl, 4-pyridinyl, 4-trifluoromethyl-pyridin-2-yl, 2,6-dimethyl-pyridin-3-yl, 6-methyl-pyridin-3-yl, 2-chloro-5-pyridinyl, 2-dimethylamino-5-pyridinyl, 6-methoxy-pyridin-3-yl, 6-methylsulfanyl-pyridin-3-yl, 2-hydroxy-5-pyridinyl, 6-bromo-pyridin-3-yl, or pyrazin-2-yl.

16. A compound as defined in claim 1, wherein Cyc is phenyl, 3-methoxyphenyl, 3-fluorophenyl, 4-fluorophenyl, 3-chlorophenyl, 4-chlorophenyl, 3,4-dichlorophenyl, 3-chloro-2-fluorophenyl, 4-chloro-2-fluorophenyl, 3-chloro-4-fluorophenyl, 4-trifluoromethylphenyl, 4-methanesulfanylphenyl, 3-methyl-4-methanesulfanylphenyl, 2-pyridinyl, 3-pyridinyl, or 6-methyl-3-pyridinyl.

17. A compound as defined in claim 1, wherein each $R^k$ moiety is independently selected from the group consisting of: methyl, methoxy, fluoro, chloro, trifluoromethyl, methanesulfanyl, trifluoromethanesulfanyl, cyano, and trifluoromethoxy.

18. A compound as defined in claim 1, wherein $R^l$ and $R^m$ are each independently —H or methyl.

19. A compound as defined in claim 1, wherein $R^5$ is —H or methyl.

20. A compound as defined in claim 1, wherein $R^5$ is —H.

21. A compound as defined in claim 1, wherein $R^6$ is —H, methyl, ethyl, isopropyl, sec-butyl, cyclopropyl, cyclobutyl, or cyclopentyl, each unsubstituted or substituted as previously described.

22. A compound as defined in claim 1, wherein $R^6$ is —H or methyl.

23. A compound as defined in claim 1, wherein $R^7$ is —H, methyl, ethyl, propyl, isopropyl, sec-butyl, cyclopropyl, cyclobutyl, cyclopentyl, cyclohexyl, cyclopropylmethyl, cyclobutylmethyl, or cyclopentylmethyl, each unsubstituted or substituted as previously described.

24. A compound as defined in claim 1, wherein $R^7$ is methyl, ethyl, isopropyl, sec-butyl, cyclopropyl, cyclobutyl, or cyclopentyl.

25. A compound as defined in claim 1, wherein $R^7$ is methyl, ethyl, isopropyl, or cyclopropyl.

26. A compound as defined in claim 1, wherein $R^6$ and $R^7$ taken together with their nitrogen of attachment form azetidinyl, pyrrolidinyl, piperidinyl, piperazinyl, morpholinyl, thiomorpholinyl, 1,1-dioxo-1$\lambda^6$-thiomorpholin-4-yl, homopiperidinyl, diazepanyl, or homomorpholinyl, each unsubstituted or substituted as previously described.

27. A compound as defined in claim 1, wherein $R^6$ and $R^7$ taken together with their nitrogen of attachment form piperidinyl, pyrrolidinyl, morpholinyl, 4-isopropyl-piperazin-1-yl, or homomorpholinyl.

28. A compound selected from the group consisting of:
[4-(3,4-Dichloro-phenoxy)-3-methylaminomethyl-phenyl]-(4-isopropyl-piperazin-1-yl)-methanone;
(4-Cyclopropyl-piperazin-1-yl)-[3-methylaminomethyl-4-(4-methylsulfanyl-phenoxy)-phenyl]-methanone;
(4-Isopropyl-piperazin-1-yl)-[3-methylaminomethyl-4-(4-methylsulfanyl-phenoxy)-phenyl]-methanone;
(4-Isopropyl-piperazin-1-yl)-[3-methylaminomethyl-4-(3-methyl-4-methylsulfanyl-phenoxy)-phenyl]-methanone;
(4-Cyclopropyl-piperazin-1-yl)-[4-(3,4-dichloro-phenoxy)-3-methylaminomethyl-phenyl]-methanone;
(4-Isopropyl-piperazin-1-yl)-[4-(3-methoxy-phenoxy)-3-methylaminomethyl-phenyl]-methanone;
[4-(4-Chloro-phenoxy)-3-methylaminomethyl-phenyl]-(4-isopropyl-piperazin-1-yl)-methanone;
[4-(4-Chloro-phenoxy)-3-cyclopropylaminomethyl-phenyl]-(4-isopropyl-piperazin-1-yl)-methanone;
(4-Isopropyl-piperazin-1-yl)-[3-methylaminomethyl-4-(pyridin-3-yloxy)-phenyl]-methanone;
(4-Cyclopropyl-piperazin-1-yl)-[3-methylaminomethyl-4-(pyridin-3-yloxy)-phenyl]-methanone;
[4-(3-Chloro-phenoxy)-3-methylaminomethyl-phenyl]-(4-cyclopropyl-piperazin-1-yl)-methanone;

(4-Cyclopropyl-piperazin-1-yl)-(3-methylaminomethyl-4-phenoxy-phenyl)-methanone;
(4-Cyclopropyl-piperazin-1-yl)-[4-(3-fluoro-phenoxy)-3-methylaminomethyl-phenyl]-methanone;
(4-Cyclopropyl-piperazin-1-yl)-[3-methylaminomethyl-4-(4-trifluoromethyl-phenoxy)-phenyl]-methanone;
[3-Cyclopropylaminomethyl-4-(pyridin-3-yloxy)-phenyl]-(4-cyclopropyl-piperazin-1-yl)-methanone;
(4-Cyclopropyl-piperazin-1-yl)-[3-methylaminomethyl-4-(3-methyl-4-methylsulfanyl-phenoxy)-phenyl]-methanone;
[3-Cyclopropylaminomethyl-4-(pyridin-3-yloxy)-phenyl]-(4-isopropyl-piperazin-1-yl)-methanone;
[4-(4-Chloro-phenoxy)-3-methylaminomethyl-phenyl]-(4-cyclopropyl-piperazin-1-yl)-methanone;
(4-Cyclopropyl-piperazin-1-yl)-[4-(4-fluoro-phenoxy)-3-methylaminomethyl-phenyl]-methanone;
(4-Cyclopropyl-piperazin-1-yl)-[3-methylaminomethyl-4-(6-methyl-pyridin-3-yloxy)-phenyl]-methanone;
[4-(3-Chloro-4-fluoro-phenoxy)-3-methylaminomethyl-phenyl]-(4-cyclopropyl-piperazin-1-yl)-methanone;
[4-(4-Chloro-2-fluoro-phenoxy)-3-methylaminomethyl-phenyl]-(4-cyclopropyl-piperazin-1-yl)-methanone;
[4-(3-Chloro-2-fluoro-phenoxy)-3-methylaminomethyl-phenyl]-(4-cyclopropyl-piperazin-1-yl)-methanone;
[4-(4-Chloro-phenylsulfanyl)-3-methylaminomethyl-phenyl]-(4-cyclopropyl-piperazin-1-yl)-methanone;
(4-Cyclopropyl-piperazin-1-yl)-[3-methylaminomethyl-4-(pyridin-2-ylsulfanyl)-phenyl]-methanone;
[4-Cyclopropylaminomethyl-3-(pyridin-3-yloxy)-phenyl]-(4-isopropyl-piperazin-1-yl)-methanone;
[4-Cyclopropylaminomethyl-3-(pyridin-3-yloxy)-phenyl]-(4-cyclopropyl-piperazin-1-yl)-methanone;
(4-Isopropyl-piperazin-1-yl)-[4-piperidin-1-ylmethyl-3-(pyridin-3-yloxy)-phenyl]-methanone;
(4-Cyclopropyl-piperazin-1-yl)-[4-piperidin-1-ylmethyl-3-(pyridin-3-yloxy)-phenyl]-methanone;
[3-(4-Chloro-phenoxy)-4-methylaminomethyl-phenyl]-(4-isopropyl-piperazin-1-yl)-methanone;
[3-(3,4-Dichloro-phenoxy)-4-methylaminomethyl-phenyl]-(4-isopropyl-piperazin-1-yl)-methanone;
[3-(3-Chloro-phenoxy)-4-methylaminomethyl-phenyl]-(4-isopropyl-piperazin-1-yl)-methanone;
(4-Cyclopropyl-piperazin-1-yl)-[3-(3,4-dichloro-phenoxy)-4-methylaminomethyl-phenyl]-methanone
[5-(4-Isopropyl-piperazin-1-yl)-2-(4-methylsulfanyl-phenoxy)-benzyl]-methyl-amine;
Methyl-[5-(4-methyl-piperazin-1-yl)-2-(4-methylsulfanyl-phenoxy)-benzyl]-amine;
[5-(4-Cyclobutyl-piperazin-1-yl)-2-(4-methylsulfanyl-phenoxy)-benzyl]-methyl-amine;
Methyl-[2-(4-methylsulfanyl-phenoxy)-5-(4-pyridin-4-yl-piperazin-1-yl)-benzyl]-amine;
[5-[4-(2-Fluoro-ethyl)-piperazin-1-yl]-2-(4-methylsulfanyl-phenoxy)-benzyl]-methyl-amine;
[5-(4-Cyclopropyl-piperazin-1-yl)-2-(4-methylsulfanyl-phenoxy)-benzyl]-methyl-amine
[5-(4-Cyclopropyl-piperazin-1-yl)-2-(3,4-dichloro-phenoxy)-benzyl]-methyl-amine;
[2-(3,4-Dichloro-phenoxy)-5-(4-isopropyl-piperazin-1-yl)-benzyl]-methyl-amine;
1-[3-Methylaminomethyl-4-(4-methylsulfanyl-phenoxy)-phenyl]-piperazin-2-one;
4-Isopropyl-1-[3-methylaminomethyl-4-(4-methylsulfanyl-phenoxy)-phenyl]-piperazin-2-one;
1-[4-(3,4-Dichloro-phenoxy)-3-methylaminomethyl-phenyl]-4-isopropyl-piperazin-2-one;
(4-Cyclopropyl-piperazin-1-yl)-[4-(3,4-dichloro-benzyloxy)-3-methylaminomethyl-phenyl]-methanone;
Cyclopropyl-[5-(4-isopropyl-piperazin-1-ylmethyl)-2-(4-methylsulfanyl-phenoxy)-benzyl]-amine;
[5-(4-Isopropyl-piperazin-1-ylmethyl)-2-(4-methylsulfanyl-phenoxy)-benzyl]-methyl-amine;
[5-(4-Isopropyl-piperazin-1-ylmethyl)-2-(4-methylsulfanyl-phenoxy)-benzyl]-dimethyl-amine;
Ethyl-[5-(4-isopropyl-piperazin-1-ylmethyl)-2-(4-methylsulfanyl-phenoxy)-benzyl]-amine;
Isopropyl-[5-(4-isopropyl-piperazin-1-ylmethyl)-2-(4-methylsulfanyl-phenoxy)-benzyl]-amine;
5-(4-Isopropyl-piperazin-1-ylmethyl)-2-(4-methylsulfanyl-phenoxy)-benzylamine;
4-[4-(3,4-Dichloro-phenoxy)-3-methylaminomethyl-benzyl]-1-isopropyl-piperazin-2-one;
1-[4-(3,4-Dichloro-phenoxy)-3-methylaminomethyl-benzyl]-4-isopropyl-piperazin-2-one;
[4-(3-Chloro-phenoxy)-3-methylaminomethyl-phenyl]-(4-cyclobutyl-piperazin-1-yl)-methanone;
(4-Cyclobutyl-piperazin-1-yl)-[4-(3,4-dichloro-phenoxy)-3-methylaminomethyl-phenyl]-methanone;
(4-Cyclopentyl-piperazin-1-yl)-[4-(3,4-dichloro-phenoxy)-3-methylaminomethyl-phenyl]-methanone;
[4-(3-Chloro-phenoxy)-3-methylaminomethyl-phenyl]-(4-cyclopentyl-piperazin-1-yl)-methanone;
[4-(4-Chloro-phenoxy)-3-methylaminomethyl-phenyl]-(4-cyclobutyl-piperazin-1-yl)-methanone;
[4-(4-Chloro-phenoxy)-3-methylaminomethyl-phenyl]-(4-cyclopentyl-piperazin-1-yl)-methanone;
(4-Isopropyl-piperazin-1-yl)-[3-methylaminomethyl-4-(4-trifluoromethyl-pyridin-2-ylsulfanyl)-phenyl]-methanone;
(4-Cyclopropyl-piperazin-1-yl)-[4-dimethylaminomethyl-3-(2,6-dimethyl-pyridin-3-yloxy)-phenyl]-methanone;
(3-Benzyloxy-4-dimethylaminomethyl-phenyl)-(4-cyclopropyl-piperazin-1-yl)-methanone;
[4-{[Bis-(2-methoxy-ethyl)-amino]-methyl}-3-(2,6-dimethyl-pyridin-3-yloxy)-phenyl]-(4-cyclopropyl-piperazin-1-yl)-methanone;
[3-(2,6-Dimethyl-pyridin-3-yloxy)-4-morpholin-4-ylmethyl-phenyl]-(4-isopropyl-piperazin-1-yl)-methanone;
(4-{[Bis-(2-methoxy-ethyl)-amino]-methyl}-3-phenoxy-phenyl)-(4-isopropyl-piperazin-1-yl)-methanone;
[5-(4-Isopropyl-piperazine-1-carbonyl)-2-(3-methoxy-phenoxy)-benzyl]-methyl-carbamic acid tert-butyl ester;
and pharmaceutically acceptable salts thereof.

29. A compound or pharmaceutically acceptable salt according to claim 1.

30. A pharmaceutical composition comprising: (a) an effective amount of a compound of claim 1 and (b) a pharmaceutically acceptable excipient.

31. A pharmaceutical composition according to claim 30, further comprising topiramate.

* * * * *